US006331537B1

(12) United States Patent
Hamilton et al.

(10) Patent No.: US 6,331,537 B1
(45) Date of Patent: Dec. 18, 2001

(54) CARBOXYLIC ACIDS AND CARBOXYLIC ACID ISOSTERES OF N-HETEROCYCLIC COMPOUNDS

(75) Inventors: Gregory S. Hamilton, Catonsville, MD (US); Mark H. Norman, Thousand Oaks, CA (US); Yong-Qian Wu, Columbia, MD (US)

(73) Assignee: GPI Nil Holdings, Inc., Wilmington, DE (US)

( * ) Notice: Subject to any disclaimer, the term of this patent is extended or adjusted under 35 U.S.C. 154(b) by 0 days.

(21) Appl. No.: 09/453,571

(22) Filed: Dec. 2, 1999

Related U.S. Application Data

(63) Continuation-in-part of application No. 09/204,237, filed on Dec. 3, 1998, now abandoned
(60) Provisional application No. 60/087,788, filed on Jun. 3, 1998.

(51) Int. Cl.7 .......................... A01N 43/46; A61K 31/55; C07D 403/12
(52) U.S. Cl. .......................... 514/215; 548/200; 548/201; 548/123; 548/124; 548/127; 548/128; 548/131; 548/132; 548/134; 548/135; 548/136; 548/143; 548/182; 548/206; 548/215; 548/240; 548/255; 548/262.2; 548/300.1; 548/311.1; 548/356.1; 548/364.1; 548/366.4; 548/540; 548/212; 548/326; 548/360; 548/361; 548/362; 548/363; 548/364; 548/365; 548/369; 548/371; 548/572; 548/374; 548/376; 548/378; 548/380; 548/383; 548/396; 548/401; 548/402; 548/406; 540/596; 540/597; 540/602; 540/603; 546/207; 546/208; 546/209; 546/210
(58) Field of Search ...................................... 548/200, 201, 548/540, 123, 124, 127, 128, 131, 132, 135, 136, 143, 182, 206, 215, 240, 250, 255, 262.2, 300.1, 311.1, 356.1, 364.1, 366.4; 514/360, 361, 362, 363, 364, 365, 369, 371, 372, 374, 376, 378, 380, 383, 396, 401, 402, 406, 326, 212, 215

(56) References Cited

U.S. PATENT DOCUMENTS

| 4,374,829 | 2/1983 | Harris et al. . |
| 4,431,644 | 2/1984 | Smith et al. . |
| 4,472,380 | 9/1984 | Harris et al. . |
| 4,692,458 | 9/1987 | Ryan et al. . |
| 4,734,420 | 3/1988 | Ryan et al. . |
| 4,745,124 | 5/1988 | Ryan et al. . |
| 4,766,110 | * 8/1988 | Ryan et al. ............. 514/19 |
| 4,808,573 | 2/1989 | Gold et al. . |
| 4,818,749 | 4/1989 | Gold et al. . |
| 5,002,962 | 3/1991 | Loscalzo . |
| 5,002,963 | 3/1991 | De Luca et al. . |
| 5,128,483 | 7/1992 | Trybulski et al. . |
| 5,147,877 | 9/1992 | Goulet . |
| 5,166,317 | 11/1992 | Wallace et al. . |
| 5,192,773 | 3/1993 | Armistead et al. . |
| 5,204,338 | 4/1993 | Baader et al. . |
| 5,214,034 | 5/1993 | Nakayama et al. . |
| 5,215,969 | 6/1993 | Springer et al. . |
| 5,232,923 | 8/1993 | Fukazawa et al. . |
| 5,294,603 | 3/1994 | Rinehart . |
| 5,321,009 | 6/1994 | Baeder et al. . |
| 5,330,993 | 7/1994 | Armistead et al. . |
| 5,342,942 | 8/1994 | Jaen et al. . |
| 5,348,944 | 9/1994 | Gold et al. . |
| 5,359,138 | 10/1994 | Takeuchi et al. . |
| 5,447,915 | 9/1995 | Schreiber et al. . |

(List continued on next page.)

FOREIGN PATENT DOCUMENTS

| 3508251 | 11/1986 | (DE) . |
| 4015255 | 11/1991 | (DE) . |
| 4425950 | 1/1996 | (DE) . |
| 012401 | 6/1980 | (EP) . |
| 048159 | 3/1982 | (EP) . |
| 050800 | 5/1982 | (EP) . |
| 073143 | 3/1983 | (EP) . |
| 088350 | 9/1983 | (EP) . |
| 180 544 | 5/1986 | (EP) . |
| 196841 | 10/1986 | (EP) . |
| 3636278 | 10/1986 | (EP) . |
| 333174 | 9/1989 | (EP) . |
| 35200 | 1/1990 | (EP) . |
| 378318 | 7/1990 | (EP) . |
| 405994 | 1/1991 | (EP) . |
| 443983 | 8/1991 | (EP) . |

(List continued on next page.)

OTHER PUBLICATIONS

Likhosherstov et al. "Azacycloalkanes. XX. Derivatives of hexahydroazepine–2–carboxylic acid" Ca 89:24120, 1978.*
Narasaka et al. "Oxidative generation of . . . " CA 120:191500, 1993.*
Wermuth "Molecular variations based on isosteric replacements" CA 126:186, 1996.*
King "Bioisosters, conformational restriction and prodrugs . . . " Med. chem. Principle Practice, pp. 206–209, 1994.*
Wilbraham et al. "Organic and biological chemistry" pp. 387, 1985.*

(List continued on next page.)

Primary Examiner—Ceila Chang
(74) Attorney, Agent, or Firm—Gary M. Nath; Todd L. Juneau; Joshua B. Goldber

(57) ABSTRACT

This invention relates to novel N-heteorocyclic carboxylic acids and carboxylic acid isosteres, their preparation and use for treating neurological disorders including physically damaged nerves and neurodengenerative diseases, for treating alopecia and promoting hair growth, for treating vision disorders and/or improving vision, and for treating memory impairment and/or enhancing memory performance by administering such compounds.

18 Claims, 12 Drawing Sheets

U.S. PATENT DOCUMENTS

| | | |
|---|---|---|
| 5,453,437 | 9/1995 | Schohe et al. . |
| 5,472,687 | 12/1995 | Proctor . |
| 5,504,197 | 4/1996 | Schubert et al. . |
| 5,506,243 | 4/1996 | Ando et al. . |
| 5,516,797 | 5/1996 | Armistead et al. . |
| 5,527,907 | 6/1996 | Or et al. . |
| 5,530,121 | 6/1996 | Kao et al. . |
| 5,536,737 | 7/1996 | Kobayashi et al. . |
| 5,541,189 | 7/1996 | Luly et al. . |
| 5,541,192 | 7/1996 | Skotnicki et al. . |
| 5,543,423 | 8/1996 | Zelle et al. . |
| 5,585,397 | 12/1996 | Tung et al. . |
| 5,599,927 | 2/1997 | Or et al. . |
| 5,604,294 | 2/1997 | Luly et al. . |
| 5,614,547 | 3/1997 | Hamilton et al. . |
| 5,620,971 | 4/1997 | Armistead et al. . |
| 5,629,325 | 5/1997 | Lin et al. . |
| 5,646,167 | 7/1997 | MacPherson et al. . |
| 5,654,332 | 8/1997 | Armistead et al. . |
| 5,665,774 | 9/1997 | Armistead et al. . |
| 5,696,135 | 12/1997 | Steiner et al. . |
| 5,703,088 | 12/1997 | Sharpe et al. . |
| 5,714,510 | 2/1998 | Proctor . |
| 5,717,092 | 2/1998 | Armistead et al. . |
| 5,721,256 | 2/1998 | Hamilton et al. . |
| 5,744,485 | 4/1998 | Zelle et al. . |
| 5,780,484 | 7/1998 | Zelle et al. . |
| 5,786,378 | 7/1998 | Hamilton et al. . |
| 5,795,908 | 8/1998 | Hamilton et al. . |
| 5,798,355 | 8/1999 | Steiner et al. . |
| 5,801,187 | 9/1998 | Li et al. . |
| 5,801,197 | 9/1998 | Steiner et al. . |
| 5,811,434 | 9/1998 | Vertex . |
| 5,840,736 | 11/1998 | Vertex . |
| 5,843,960 | 12/1998 | Steiner et al. . |
| 5,846,979 | 12/1998 | Hamilton et al. . |
| 5,846,981 | 12/1998 | Steiner et al. . |
| 5,859,031 | 1/1999 | Hamilton et al. . |
| 5,874,449 | 2/1999 | Hamilton et al. . |
| 5,898,029 | 4/1999 | Lyons et al. . |

FOREIGN PATENT DOCUMENTS

| | | |
|---|---|---|
| 468339 | 1/1992 | (EP) . |
| 471135 | 2/1992 | (EP) . |
| 476933 | 3/1992 | (EP) . |
| 488 258 | 6/1992 | (EP) . |
| 494005 | 7/1992 | (EP) . |
| 519819 | 12/1992 | (EP) . |
| 610744 | 10/1993 | (EP) . |
| 652229 | 5/1995 | (EP) . |
| 823419 | 2/1998 | (EP) . |
| 2247456 | 3/1992 | (GB) . |
| 05-178824 | 7/1993 | (JP) . |
| 05-194235 | 8/1993 | (JP) . |
| WO 85/04577 | 10/1985 | (WO) . |
| WO 88/00040 | 1/1988 | (WO) . |
| WO 88/09789 | 12/1988 | (WO) . |
| WO 89/06234 | 7/1989 | (WO) . |
| WO 91/04985 | 4/1991 | (WO) . |
| WO 91/13088 | 9/1991 | (WO) . |
| WO 9200278 | 1/1992 | (WO) . |
| WO 92/04370 | 3/1992 | (WO) . |
| WO 92/11245 | 7/1992 | (WO) . |
| WO 92/11850 | 7/1992 | (WO) . |
| WO 92/21313 | 10/1992 | (WO) . |
| WO 92/19593 | 11/1992 | (WO) . |
| WO 92/19745 | 11/1992 | (WO) . |
| WO 93/14762 | 5/1993 | (WO) . |
| WO 93/14072 | 7/1993 | (WO) . |
| WO 93/13066 | 8/1993 | (WO) . |
| WO 93/18736 | 9/1993 | (WO) . |
| WO 94/03476 | 2/1994 | (WO) . |
| WO 94/04129 | 3/1994 | (WO) . |
| WO 94/07858 | 4/1994 | (WO) . |
| WO 94/12474 | 6/1994 | (WO) . |
| WO 94/13629 | 6/1994 | (WO) . |
| WO 94/14428 | 7/1994 | (WO) . |
| WO 94/15900 | 7/1994 | (WO) . |
| WO 95/02684 | 1/1995 | (WO) . |
| WO 95/12398 | 11/1995 | (WO) . |
| WO 95/12572 | 11/1995 | (WO) . |
| WO 95/35308 | 12/1995 | (WO) . |
| WO 95/35367 | 12/1995 | (WO) . |
| WO 96/34303 | 12/1995 | (WO) . |
| WO 96/06846 | 3/1996 | (WO) . |
| WO 96/15101 | 5/1996 | (WO) . |
| WO 96/17816 | 6/1996 | (WO) . |
| WO 96/20725 | 7/1996 | (WO) . |
| WO 96/20949 | 7/1996 | (WO) . |
| WO 96/36630 | 11/1996 | (WO) . |
| WO 96/40140 | 12/1996 | (WO) . |
| WO 96/41609 | 12/1996 | (WO) . |
| WO 9606097 | 12/1996 | (WO) . |
| WO 9640633 | 12/1996 | (WO) . |
| WO 98/13343 | 4/1997 | (WO) . |
| WO 97/23202 | 7/1997 | (WO) . |
| WO 97/23458 | 7/1997 | (WO) . |
| WO 97/31898 | 9/1997 | (WO) . |
| WO 97/36869 | 10/1997 | (WO) . |
| WO 97/38008 | 10/1997 | (WO) . |
| WO 97/20554 | 12/1997 | (WO) . |
| WO 97/48681 | 12/1997 | (WO) . |
| WO 97/49695 | 12/1997 | (WO) . |
| WO 98/08827 | 3/1998 | (WO) . |
| WO 98/20891 | 5/1998 | (WO) . |
| WO 98/20892 | 5/1998 | (WO) . |
| WO 98/20893 | 5/1998 | (WO) . |
| WO 98/22432 | 5/1998 | (WO) . |
| WO 98/24805 | 6/1998 | (WO) . |
| WO 98/29117 | 7/1998 | (WO) . |
| WO 9837885 | 9/1998 | (WO) . |
| WO 99/45006 | 9/1998 | (WO) . |
| WO 9855090 | 12/1998 | (WO) . |
| WO 9855091 | 12/1998 | (WO) . |
| WO 99/10340 | 3/1999 | (WO) . |
| WO 9962881 | 12/1999 | (WO) . |
| PCT/US99/28663 | 11/2000 | (WO) . |
| PCT/US99/28663 | 12/2000 | (WO) . |
| 9207782 | 9/1992 | (ZA) . |

OTHER PUBLICATIONS

Bundgaard "Design of prodrugs" pp. 1, 24–25, 1985.*

Wermuth C.G. (ed.) *The Practice of Medicinal Chemistry*, Academic Press, London and San Diego, 1996, p. 215–221, Spec. 220.

Andrus, Merrit B., "Structure–based design of an acyclic ligand that bridges FKBP 12 and calcineurin," *J. Am. Chem. Soc.*, 1993, 115(2), 10420–21.

Armistead, D.M. et al., "Design, synthesis and structure of non–macrocyclic inhibitors of FKBP12, the major binding protein for the immunosuppressant FK506," *Acta Crystallogr.*, 1995, D51(4), 522–8.

Askin, D. et al., Chemistry of FK–506: benzilic acid rearrangement of the tricarbonyl system, *Tetrahedron Lett.*, 1989, 30(6), 671–74.

Baader, Ekkehard et al., "Inhibition of prolyl 4–hydroxylase by oxalyl amino acid derivatives in vitro, in isolated microsomes and in embryonic chicken tissues," *Biochem. J.*, 1994, 300(2), 525–30.

Baumann, K. et al., "Synthesis and oxidative cleavage of the major equilibrium products of ascomycin and FK506," *Tetrahedron Lett.*, 1995, 26(13), 2231–34.

Bender, D. et al., "Periodate Oxidation of α–Keto γ–Lactams. Enol Oxidation and β–Lactam Formation Mechanism of Periodate Hydroxylation Reactions," *J. Org. Chem.*, 1978, 43, 3354–62.

Birkenshaw, T. et al., "Synthetic FKBP12 Ligands Design and Synthesis of Pyranose Replacements," *Bioorg. Med. Chem. Lett.*, 1994, 4, 2501–06.

Boulmedais, A. et al., "Stereochimie de la reduction electrochimique d'acetoamides optiquement actives Electroreduction de benzoylformaides derives de la S(-)-proline," *Bull. Soc. Chim. Fr.*, 1988, 185–91.

Bycroft, B. et al., "Efficient Asymmetric Synthesis of α–Amino Acids from α–Keto Acids and Ammonia with Conservation of the Chiral Reagent," *J.C.S. Chem. Comm.*, 1975, 988–89.

Caffrey, M. et al., "Synthesis and Evaluation of Dual Domain Macrocyclic FKBP12 Ligands," *Bioorg. Med. Chem. Lett.*, 1994, 4, 2507–10.

Cai, D. and Still, W.C., "Synthesis of the α, β–Diketo Amide Segment of the Novel Immunosuppressant FK506," *J. Org. Chem.*, 1988, 53, 4643–44.

Callens, Roland E.A. et al., "Preparation of Trans–5–Hydroxy–L–Pipecolic Acid and Cis–4–Hydroxy–L–Pipecolic Acid from L–Baikiain (1,2,5, 6–L–Tetrahydropyridine–2– Carboxylic Acid)," *Bull. Soc. Chim. Belg.*, 1982, 91, 713–23.

Caufield, C. and Musser, J., "Macrocyclic Immunomodulators," *Ann. Rep. Med. Chem.*, 1989, 195–204.

Chakaraborty, Tushar K. et al., "Design and Synthesis of a rapamycin–based high affinity binding FKBP12 Ligand," *Chem. Biol.*, 1995, 2(3), 157–61.

Chakaraborty, Tushar K., "Studies Directed Towards the Development of Cyclic Peptide Based Analogs of Macrolide Immunosuppressants," *Pure Appl. Chem.*, 1996, 68(3), 565–68.

Coleman, R. and Danishefsky, S., "Degradation and Manipulations of the Immunosuppressant FK506: Preparation of Potential Synthetic Inermediates," *Heterocycles*, 1989, 28, 157–61.

Colombo, L. et al., "Enantioselective Synthesis of Secondary Alcohols in the Presence of Chiral Ligands," *Tetrahedron*, 1982, 38(17), 2725–27.

Cushman, D.W. et al., "Design of potent competitive inhibitors of angiotensin–converting enzyme. Carboxyalkanoyl and mercaptoalkanoyl amino acids," *Biochem.*, 1977, 16(25), 5484–91.

Dawson, T. et al., "Immunosuppressant RK506 enhances phosphorylation of nitric oxide synthase and protects against glutamate neurotoxicity," *Proc. Nat. Acad. Sci.*, 1993, 90, 9808–12.

Dawson, T. et al., "The immunophilins, FK506 binding protein and cyclophilin, are discretely localized in the brain: relationship to calcineurin," *Neuroscience*, 1994, 62, 569–80.

Dumont, Francis J. et al., "The Immunosuppressive and Toxic Effects of FK–506 are Mechanistically Related: Pharmacology of a Novel Antagonist of FK–506 and Rapamycin," *J. Exp. Med.*, 1992, 176, 751–60.

Egbertson, M. and Danishefsky, S., "Synthetic Route to the "Tricarbonyl" Region of FK506," *J. Org. Chem.*, 1989, 54 11–12.

Finberg, R. et al., "Prevention of HIV–1 Infection and Preservation of CD4 Function by the Binding of CPFs to gp120," *Science*, 1990, 249, 287–90.

Fisher, Matthew et al., "On the Remarkable Propensity for Carbon–Carbon Bond Cleavage Reactions in the C(8)–C(10) Region of FK–506," *J. Org. Chem.*, 1991, 56(8), 2900–07.

Furber, Mark et al., "Studies Relating to the Immunosuppressive Activity of FK506," *Tetrahedron Lett.*, 1993, 34(8), 1351–54.

Furber, Mark, "FKBP–12–Ligand–Calcineurin Interactions: Analogs of SBL506," *J. Am. Chem. Soc.*, 1995, 117(27), 7267–68.

Gold, B. et al., "Regulation of aberrant neurofilament phosphorylation in neuronal perikarya. IV. Evidence for the involvement of two signals," *Brain Research*, 1993, 626, 23–30.

Gold, B. et al., "Regulation of the Transcription Factor c–JUN by nerve growth factor in adult sensory neurons," *Neuroscience Letters*, 1993, 154, 129–33.

Gold, B. et al., "The immunosuppressant FK506 increases functional recovery and nerve regeneration following peripheral nerve injury," *Restorative Neurology and Neuroscience*, 1994, 6, 287–96.

Gold, B. et al., "Multiple signals underlie the axotomy–induced up–regulation of c–JUN in adult sensory neurons," *Neuroscience Letters*, 1994, 176, 123–27.

Gold, B. et al., "The immunosuppressant FK506 increases the rate of axonal regeneration in rat sciatic nerve," *J. Neuroscience*, 15 (1995) 7509–16.

Goodfellow, Val S. et al., "p–Nitrophenyl 3–Diazopyruvate and Diazopyruvamides, a New Family of Photoactivatable Cross–Linking Bioprobes," *Biochemistry*, 1989, 28(15), 6346–60.

Goulet, M. and Boger, J., "Degradative Studies on the Tricarbonyl Containing Macrolide Rapamycin," 1990, 4845–48.

Goulet, Mark T. et al., "Construction of an FK–506 Analog From Rapamycin–Derived Materials," *Tetrahedron Lett.*, 1991, 32(36), 4627–30.

Hamilton, Gary S. and Steiner, Joseph P., "Neuroimmunophilin Ligands as Novel Therapeutics for the Treatment of Degenerative Disorders of the Nervous System," 1–71.

Harding, M. et al., "A receptor for the immunosuppressant FK506 is a cis–trans peptidylprolyl isomerase," *Nature*, 1989, 349, 758–60.

Hauske, J. et al., "Design and Synthesis of Novel FKBP Inhibitors," *J. Med. Chem.*, 1992, 35, 4284–96.

Hauske, James R. et al., "Investigation of the effects of synthetic, non–cytotoxic immunophilin inhibitors on MDR," *Bioorg. Med. Chem. Lett.*, 1994, 4(17), 2097–102.

Haüsler, Johannes and Schmidt, Ulrich, "Amino Acids and peptides. IX. Pyruvoyl amino acids," *Chem. Ber.*, 1974, 107, 145–51. (In German).

Hayward, C. et al., "An Application of the Suarez Reaction to the Regiospecific and Stereospecific Synthesis of the C28–C42 segment of Rapamycin," 1993, 3989–92.

Hayward, C. et al., "Total Synthesis of rapamycin via a novel titanium–mediated aldol macrocyclization reaction," *J. Am. Chem. Soc.*, 1993, 115(20), 9345–46.

Hearn, Walter R., and Worthington, Robert E., "L–Proline–N–oxalic Anhydride," *J. Org. Chem.*, 1967, 32(12), 4072–74.

Holt, D. et al., "Structure–Activity Studies of Nonmacrocyclic Rapamycin Derivatives," *Bioorg. Med. Chem. Lett.*, 1993, 3, 1977–80.

Holt, D. et al., "Design, Synthesis, and Kinetic Evaluation of High–Affinity FKBP Ligands and the X–ray Crystal Structures of Their Complexes with FKBP12," *J. Am. Chem. Soc.*, 1993, 115, 9925–38.

Holt, Dennis A. et al., "Structure–activity of synthetic FKBP ligands as peptidyl–prolyl isomerase inhibitors," *Bioorg. Med. Chem. Lett.*, 1994, 4(2), 315–20.

Iwabuchi, Tokuro et al., "Effects of immunosuppressive peptidyl–prolyl cis–trans isomerase (PPIase) inhibitors, cyclosporin A, FK506, ascomycin and rapamycin, on hair growth initiation in mouse: immunosuppression is not required for new hair growth," *J. Dermatol. Sci.*, 1995, 9, 64–69.

Jiang, Hong et al., "Induction of Anagen in Telogen Mouse Skin by Topical Application of FK506, a Potent Immunosuppressant," *J. Invest. Dermatol.*, 1995, 104, 523–25.

Jones, T. et al., "Chemistry of Tricarbonyl Hemiketals and Application of Evans Technology to the Total Synthesis of the Immunosuppressant (−)–FK–506," *J. Am. Chem. Soc.*, 1990, 112(8), 2998–3017.

Jones, Brian A. et al., "A Formal Synthesis of FK–506. Exploration of Some Alternatives to Macrolactamization," *J. Org. Chem.*, 1990, 55(9), 2786–97.

Karle, Isabella L. et al., "Conformation of the Oxalamide Group in Retro–Bispeptides," *Int. J. Pept. Protein Res.*, 1994, 43(2), 160–65.

Kino, T. et al., "FK–506, A Novel Immunosuppressant Isolated from A. Streptomyces: Fermentation, Isolation, and Physico–Chemical and Biological Characteristics," *J. Antibiotics*, XL, 1987, 1249–55.

Kitamura et al., "Suppressive Effect of FK–506, a Novel Immunosuppressant, Against MPTP–Induced Dopamine Depletion in the Striatum of Young C57BL/6 Mice," *J. Neuroimmunology*, 1994, 50, 221–24.

Kocienski, P. et al., "A Synthesis of the C(1)–C(15) Segment of Tsukubaenolide (FK 506)," *Tetrahedron Lett.*, 1988, 29, 4481–84.

Linde, Robert G. et al., "Straightforward Synthesis of 1,2,3–Tricarbonyl Systems," *J. Org. Chem.*, 1991, 56(7), 2543–38.

Luengo, Juan et al., "Efficient Removal of Pipecolinate from Rapamycin and FK506 by Reaction with n–Bu$_4$N$^+$CN$^-$," *Tetrahedron Lett.*, 1993, 34(29), 4599–4602.

Luengo, Juan I. et al., "Studies on the Chemistry of Rapamycin: Novel Transformations under Lewis–Acid Catalysis," *Tetrahedron Lett.*, 1993, 34(6), 991–94.

Luengo, J. et al., "Synthesis and Structure–Activity Relationships of Macrocyclic FKBP Ligands," *Bioorg. Med. Chem. Lett.*, 1994, 4, 321–24.

Luengo, Juan I. et al., "Structure–Activity Studies of Rapamycin Analogs: Evidence That the C–7 Methoxy Group is Part of the Effector Domain and Positioned at the FKBP 12–FRAP Interface," *Chem. & Biol.*, 1995, 2(7), 471–81.

Lyons, W. E. et al., "Immunosuppressant FK506 promotes neurite outgrowth in cultures of PC 12 cells and sensory ganglia," *Proc. Nat. Acad. Sci.*, 1994, 91, 3191–95.

Lyons, W. E. et al., "Neuronal Regeneration Enhances the Expression of the Immunophilin FKBP–12," *J. Neuroscience*, 1995, 15(4), 2985–94.

Marshall, J.A. et al., "A Convenient Synthesis of Diketopiperazines Via Aminolysis of N Pyruvl α–Amino Esters," *Synthetic Communications*, 1975, 5(3), 237–44.

Mashkovskii, M.D. et al., "1–[4–(2–Hydroxy–3–Tert–Butylaminopropoxy)–indole–3–yl(5–acetamido–1–(S)–carboxypentyl)–DL–alanyl]–L–proline dihydrochloride, a new angiotensin–converting enzyme inhibitor with β–adrenoblocking properties," *Khim.–Farm. Zh.*, 1993, 27(10), 16–20. (In Russian).

Munegumi, Toratane et al., "Asymmetric Catalytic Hydrogenations of N–pyruvoyl–(S) proline esters," *Bull. Chem. Soc. Jpn.*, 1987, 60(1), 243–53.

Munoz, Benito et al., "α–Ketoamide Phe–Pro Isostere as a New Core Structure for the Inhibition of HIV Protease," *Bioorg. & Med. Chem.*, 1994, 2(10), 1085–1090.

Nakatsuka, M. et al., "Total Synthesis of FK506 and an FKBP Probe Reagent, (C$_8$, C$_9$–$^{13}$C$_2$)–FK506," *J. Am. Chem. Soc.*, 1990, 112, 5583–5601.

Nelson, F. et al., "A Novel Ring Contraction of Rapamycin," *Tetrahedron Lett.*, 1994, 35(41), 7557–60.

Ocain, T. et al., "A Nonimmunosuppressive Triene–Modified Rapamycin Analog Is A Potent Inhibitor of Peptidyl Prolyl Cis–Trans Isomerase," *Biochem. Biophys. Res. Comm.*, 1993, 192(3), 1340–46.

Pattenden, Gerald and Tankard, Mark, "Facile Synthesis of the Tricarbonyl Subunit in the Immunosuppressant Rapamycin," *Tetrahedron Lett.*, 1993, 34(16), 2677–80.

Ranganathan, Darshan et al., "Oxalopeptides as core motifs for protein design," *J. Chem. Soc*, 1994, 116, 6545–57.

Rao, A.V. Rama et al., "Studies Directed Towards the Synthesis of Immunosuppressive Agent FK–506: Construction of the Tricarbonyl Moiety," *Tetrahedron Letters*, 1990, 31, 1439–42.

Rao, A.V. Rama et al., "Studies Directed Towards the Synthesis of Immunosuppressive Agent FK–506: Synthesis of the Entire Bottom Half," *Tetrahedron Lett.*, 1991, 32(9), 1251–54.

Rao, A.V. Rama and Desibhatla, Vidyanand, "Studies Directed Towards the Synthesis of Rapamycin: Stereoselective Synthesis of C–1 to C–15 Segment," *Tetrahedron Lett.*, 1993, 34(44), 7111–14.

Ryba et al., "Cyclosporine A Prevents Neurological Deterioration of Patients with SAH—A Preliminary Report," *Acta Neurochirurgica*, 1991, 112, 25–27.

Schreiber, S., "Chemistry and Biology of the Immunophilins and their Immunosuppressive Ligands," *Science*, 1991, 251, 283–87.

Shiga et al., "Cyclosporin A Protects Against Ischemia–Reperfusion Injury in the Brain," *Brain Research*, 1992, 595, 145–48.

Skotnicki, Jerauld and Kearney, Robert M., "Ring Expanded Rapamycin Derivatives," *Tetrahedron Lett.*, 1994, 35(2), 201–02.

Skotnicki, Jerauld et al., "Synthesis of Secorapamycin Esters and Amides," *Tetrahedron Lett.*, 1994, 35(2), 197–200.

Slee, Deborah H. et al., "Selectivity in the Inhibition of HIV and FIV Protease: Inhibitory and Mechanistic Studies of Pyrrolidine–Containing α–Keto Amide and Hydroxyethylamine Core Structures," *J. Am. Chem. Soc.*, 1995, 117(48), 1187–78.

Snyder, S. and Sabatini, D., "Immunophilins and the Nervous System," *Nature Medicine*, 1995, 1, 32–37.

Soai, Kenso et al., "Asymmetric Allylation of α–Keto Amides Derived From (S)–Proline Esters," *Pept. Chem.*, 1986, 24, 327–330.

Soai, K. et al., "Asymmetric Synthesis of the Both Enantiomers of α–Hydroxy Acids by the Diastereoselective Reduction of Chiral α–Keto Amides with (Complex) Metal Hydrides in the Presence of Metallic Salt," *Chem. Lett.*, 1986, 1897–1900.

Soai, Kenso and Ishizaki, Miyuki, "Asymmetric Synthesis of Functionalized Tertiary Alcohols by Diastereoselective Allylation of Chiral α–Keto Amides Derived From (S)–Proline Esters: Control of Stereochemistry Based on Saturated Coordination of Lewis Acid," *J. Org. Chem.*, 1986, 57(17), 3290–95.

Soai, K. and Hasegawa, H., "Diasteroselective Reduction of Chiral α–Ketoamides Derived from (S)–Proline Esters with Sodium Borohydride, Preparation of Optically Active α–Hydroxy Acids," *J. Chem. Soc. Perkins Trans.I*,1985, 769–72.

Soai, K. and Ishizaki, M., "Diastereoselective Asymmetric Allylation of Chiral α–Keto amides with Allyltrimethyl–silane Preparation of Protected Homoallylic Alcohols," *J. Chem. Soc.*, 1984, 1016–17.

Somers, Patricia K. et al., "Synthesis and Analysis of 506BD, a High–Affinity Ligand for the Immunophilin FKBP," *J. Am. Chem. Soc.*, 1991, 113, 8045–56.

Steffan, Robert J. et al., "Base Catalyzed Degradations of Rapamycin," *Tetrahedron Lett.*, 1993, 34(23), 3699–702.

Steglich, Wolfgang et al., "Activated Carboxylic Acid Derivatives. II. A Simple Synthesis of 2–Oxycarboxylic Acid Amides, N– (2–Oxoacyl)amino Acid Esters and 2–oxocarboxylic Acid Hydrides," *Synthesis*, 1978, 8, 622–24. (In German).

Steiner, J. et al., "High brain densities of the immunophilin FKBP colocalized with calcineurin," *Nature*, 358 (1992) 584–7.

Steiner, J. et al., "Nonimmunosupressive ligands for neuroimmunophilins promote nerve extension in vitro and in vivo," *Society for Neuroscience Abstracts*, 1996, 22, 297.

Steiner, J. et al., "Neurotrophic immunophilin ligands stimulate structural and functional recovery in neurodegenerative animal models," *Proc. Nat. Acad. Sci.*, 1997, 94, 2019–24.

Steiner, J. et al., "Neurotrophic actions of nonimmunosuppressive analogues of immunosuppressive drugs FK506, rapamycin and cyclosporin A," *Nature Medicine*, 1997, 421–28.

Stocks, M. et al., "The Contribution to Binding of the Pyranoside Substituents in the Excised Binding Domain of Fk–506," *Bioorg. and Med. Chem. Lett.*, 1994, 4, 1457–60.

Stocks, Michael J. et al., "Macrocyclic Ring Closures Employing The Intramolecular Heck Reaction," *Tetrahedron Lett.*, 1995, 36(36), 6555–58.

Tanaka, Hirokazu et al., "Structure of FK506: A Novel Immunosuppressant Isolated from Streptomyces," *J. Am. Chem. Soc.*, 1987, 109, 5031–33.

Tatlock, J. et al., "High Affinity FKBP–12 Ligands from (R)–(-)–Carvone. Synthesis and Evaluation of FK506 Pyranose Ring Replacements," *Bioorg. Med. Chem. Lett.*, 1995, 5(21), 2489–94.

Teague, S. and Stocks, M., "The Affinity of the Excised Binding Domain of FK–506 for the Immunophilin FKBP12," *Bioorg. Med. Chem. Lett.*, 1993, 3, 1947–50.

Teaugue, S. et al., "Synthesis and Study of a Non Macrocyclic FK506 Derivative," *Bioorg. Med. Chem. Lett.*, 1994, 4, 1581–84.

Teague, S. et al., "Synthesis of FK506–Cyclosporin Hybrid Macrocycles," *Bioorg. Med. Chem. Lett.*, 1995, 5(20), 2341–46.

Teichner et al., "Treatment with Cyclosporin A Promotes Axonal Regeneration in Rats Submitted to Transverse Section of the Spinal Cord," *Int'l J. Brain Research & Neurobio.*, 1993, 34(3), 343–349.

Wang, Gary T. et al., "Synthesis of FKBP Binding of Small Molecule Mimics of the Tricarbonyl Region of FK506," *Bioorg. Med. Chem. Lett.*, 1994, 4,1161–66.

Wasserman, H. et al., "Synthesis of the "Tricarbonyl" Region of FK–506 through an Amidophosphorane," *J. Org Chem.*, 54, 2785–86.

Yohannes, Daniel et al., "Degradation of Rapamycin: Retrieval of Major Intact Subunits," *Tetrahedron Lett.*, 1992, 33(49), 7469–72.

Yohannes, Daniel et al., "Degradation of Rapamycin: Synthesis of a Rapamycin–Derived Fragment Containing the Tricarbonyl and Triene Sectors," *Tetrahedron Lett.*, 1993, 34(13), 2075–78.

Yamamoto, Satoshi et al., "Stimulation of Hair Growth by Topical Application of FK506, a Potent Immunosuppressive Agent," *J. Invest. Dermat.*, 1994, 102(2), 160–64.

Gudasheva, T.A. et al., "Synthesis and antiamnesic activity of a series of N–acylprolyl–containing dipeptides," *Eur. J. Med. Chem.*, 31 (1996), 151–7.

Waldmann, H., "Proline Benzyl Ester as Chiral Auxiliary in Barbier–Type Reactions in Aqueous Solution," *Synlett*, 1990, 627–8.

Munegumi, T. et al., "Diasteroeselective Catalytic Hydrogenation of $N^\alpha$–Pyruvoyl–(S)–prolinamide," *Bull. Chem. Soc. Jpn.*, 63 (1990)1832–34.

Hausler, J. et al., "Hydroxylsubstituierie Cyclodipeptide Durch Ringschluft Von Pyruvoylaminosaure–amiden," *Chem. Ber.*, 107 (1974) 2804–15.

Steglich, W. et al., "Eine rationelle Synthese von N–Trifluoroacetylaminosauren," *Synthesis*, (1976) 399–401.

Jou, Chemical Abstracts, vol. 126:89769.

Burbaum, Chemical Abstracts, vol. 121:109686.

Rinehart, Chemical Abstracts, vol. 121:887.

Gold, 94:82238 USPATFULL.

Baader, Chemical Abstracts, vol. 121:102790.

Baader, 93:31405 USPATFULL.

Mashkovskii, Chemical Abstracts, vol. 121:212542.

Cunliffe, Chemical Abstracts, vol. 117:49183.

Rinehart, Chemical Abstracts, vol. 115:248086.

Baader, Chemical Abstracts, vol. 116:129617.

Krit, Chemical Abstracts, vol. 115:232847.

Gold, Chemical Abstracts, vol. 111:195414.

Gold, Chemical Abstracts, vol. 111:197735.

Gold, 89:39096 USPATFULL.

Boulmedais, Chemical Abstracts, vol. 112:44174.

Ryan, 88:53796 USPATFULL.

Arzeno, 110:8697 MARPAT.

Harris, 84:52709 USPATFULL.
Smith, 84:8849 USPATFULL.
Smith, 84:8848 USPATFULL.
Harris, Chemical Abstracts, vol. 99:88574.
Smith, Chemical Abstracts, vol. 100:175294.
Neustadt, Chemical Abstracts, vol. 97:216730.
Ryan, Chemical Abstracts, vol. 97:163506.
Patchett, Chemical Abstracts, vol. 95:25634.
Cushman, Chemical Abstracts, vol. 88:18091.
Steglich, Chemical Abstracts, vol. 85:108966.
Hearn, Chemical Abstracts, vol. 68:22217.
543118 *Beilstein*.
5337004 *Beilstein*.
5059234 *Beilstein*.
442355 *Beilstein*.
422738 *Beilstein*.
407472 *Beilstein*.
Armistead, Chemical Abstracts, vol. 126:343875.
Armistead, Chemical Abstracts, vol. 127:346300.
Holt, Chemical Abstracts, vol. 127:262560.
Holt, Chemical Abstracts, vol. 127:247960.
Armistead, 97:81322 USPATFULL.
Armistead, 97:68499 USPATFULL.
Armistead, 97:33765 USPATFULL.
Amara, Chemical Abstracts, vol. 127:316501.
Armistead, Chemical Abstracts, vol. 126:272378.
Holt, Chemical Abstracts, vol. 125:86501.
Armistead, 96:41236 USPATFULL.
Stocks, Chemical Abstracts, vol. 124:29735.
Armistead, Chemical Abstracts, vol. 121:170549.
Armistead, Chemical Abstracts, vol. 122:55896.
Birkenshaw, Chemical Abstracts, vol. 122:187213.
Teague, Chemical Abstracts, vol. 121:255492.
Yamashita, Chemical Abstracts, vol. 120:315168.
Luengo, Chemical Abstracts, vol. 121:49600.
Armistead, 93:18679 USPATFULL.
Holt, Chemical Abstracts, vol. 120:134099.
Armistead, Chemical Abstracts, vol. 117:131071.
Armistead, Chemical Abstracts, vol. 119:95338.
Bender, Chemical Abstracts, vol. 89:128811.
7304610 *Beilstein*.
6662799 *Beilstein*.
6653693 *Beilstein*.
409811 *Beilstein*.
Hamilton, 97:25061 USPATFULL.
Hamilton, Chemical Abstracts, vol. 126:144545.
Hamilton, Chemical Abstracts, vol. 126:118197.
Steiner, Chemical Abstracts, vol. 126:152817.
Steiner, Chemical Abstracts, vol. 126:152815.
Baldwin, 123:350246 MARPAT.
MacLeod, 121:205217 MARPAT.
Hauske, Chemical Abstracts, vol. 122:45705.
Holt, Chemical Abstracts, vol. 121:224.
Burakoff, 92:40822 USPATFULL.
Hauske, Chemical Abstracts, vol. 118:22591.
Schreiber, Chemical Abstracts, vol. 116:34554.
Munegumi, Chemical Abstracts, vol. 113:191883.
Finberg, Chemical Abstracts, vol. 113:184256.
Toda, 113:23894 MARPAT.
Frey, 1988:488188 ZCAPLUS.
Ryan, 88:53796 USPATFULL.
Roloff, 87:68534 USPATFULL.
Roloff, Chemical Abstracts, vol. 105:1333746.
Roloff, 86:35764 USPATFULL.
Ryan, Chemical Abstracts, vol. 97:163506.
Haeusler, 1974:569816 ZCAPLUS.
Pansare, Chemical Abstracts, vol. 123:339285.
Byun, Chemical Abstracts, vol. 123:111799.
Toda, 113:23894 MARPAT.
Suzuki, Chemical Abstracts, vol. 108:150009.
Koft, Chemical Abstracts, vol. 106:119239.
Bycroft, Chemical Abstracts, vol. 84:106021.

* cited by examiner

Promotion of Hair Growth by Neuroimmunophilin Ligands

CARBOXYLIC ACIDS AND CARBOXYLIC ACID ISOSTERES OF N-HETEROCYCLIC COMPOUNDS

RELATED APPLICATION DATA

This application is a continuation-in-part of U.S. patent application Ser. No. 09/204,237 filed Dec. 3, 1998, now abandoned which is a continuation-in-part of U.S. patent application Ser. No. 60/087,788 filed Jun. 3, 1998.

BACKGROUND OF THE INVENTION

1. Field of the Invention

This invention relates to novel carboxylic acid and carboxylic acid isosteres of N-heterocylic compounds, their preparation, their inclusion in pharmaceutical compositions, and their preparation and use for preventing and/or treating neurological disorders; for treating alopecia and promoting hair growth; for treating vision disorders and/or improving vision; for treating memory impairment and/or enhancing memory performance; and for preventing and/or treating hearing loss in an animal.

2. Description of the Prior Art

Neurological Background

It has been found that picomolar concentrations of an immunosuppressant such as FK506 and rapamycin stimulate neurite out growth in PC12 cells and sensory nervous, namely dorsal root ganglion cells (DRGs). Lyons et al., *Proc. of Natl. Acad. Sci.,* 1994 vol. 91, pp. 3191–3195. In whole animal experiments, FK506 has been shown to stimulate nerve regeneration following facial nerve injury and results in functional recovery in animals with sciatic nerve lesions.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived nerve factor (BDNF), glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, J. Am. Soc. Nephrol. 1:162); neurological deficits, such as involuntary tremors, or non-specific cerebral angina such as non-localized headaches (De Groen et al., 1987, N. Engl. J. Med. 317:861); and vascular hypertension with complications resulting therefrom (Kahan et al., 1989 N. Engl. J. Mod. 321: 1725).

Accordingly, there is a need for small-molecule compounds which are useful for neurotrophic effects and for treating neurodegenerative disorders.

Hair Loss Background

Hair loss occurs in a variety of situations. These situations include male pattern alopecia, alopecia senilis, alopecia areata, diseases accompanied by basic skin lesions or tumors, and systematic disorders such as nutritional disorders and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of EK506 (Yamamoto et al., J. Invest. Dermatol., 1994, 102, 160–164; Jiang et al., J. Tnvest. Dermatol. 1995, 104, 523–525) and cyclosporin (Iwabuchi et al., J. Dermatol. Sci. 1995, 9, 64–69) stimulates hair growth in a dose-dependent manner. One form of hair loss, alopecia areata, is known to be associated with autoimmune activities; hence, topically administered immunomodulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for affecting hair growth. Similar to FK506 (and the claimed variations in the Honbo et al. patent), the compounds claimed in these patents are relatively large. Further, the cited patents relate to immunomodulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for small molecule compounds which are useful as hair revitalizing compounds.

Vision Disorder Background

The visual system is composed of the eyes, ocular adnexa and the visual pathways. Dysfunction of the visual system may lead to permanent or temporary visual impairment, i.e. a deviation from normal in one or more functions of the eye. Visual impairment manifests itself in various ways and includes a broad range of visual dysfunctions and disturbances. Without limitation, these dysfunctions and disturbances include partial or total loss of vision, the need for correction of visual acuity for objects near and far, loss of visual field, impaired ocular motility without diplopia (double vision), impaired or skewed color perception, limited adaptation to light and dark, diminished accommodation, metamorphopsic distortion, impaired binocular vision, paresis of accommodation, iridoplegia, entropion, ectropion, epiphora, lagophthalmos, and scarring. See *Physicians' Desk Reference (PDR) for Ophthalmology,* 16th Edition, 6:47 (1988). The visual system may be adversely affected by various ophthalmologic disorders, diseases, injuries, and complications, including, without limitation, genetic disorders; disorders associated with aging or degenerative diseases; disorders correlating to physical injury to the eye, head, or other parts of the body resulting from external forces; disorders resulting from environmental factors; disorders resulting from a broad range of diseases; and combinations of any of the above.

The visual system is a complex system composed of numerous components. Visual impairment can involve the entire visual system, any one component, or any combination of components, depending upon the precise nature of the circumstances. The eye is composed of a lens, which is suspended in the zonules of Zinn and is focused by the ciliary body. The ciliary body also secretes aqueous humor, which fills the posterior chamber, passes through the pupil into the anterior chamber, then drains primarily via the canal of Schlemm. The iris regulates the quantity of light entering the eye by adjusting the size of its central opening, the pupil. A visual image is focused onto the retina, the fovea centralis being the retinal area of sharpest visual acuity. The conjunctive is the mucus membrane which lines the eyelids and the eyeball, and ends abruptly at the limbus conjunctivae, the edge of the conjunctive overlapping the cornea. The cornea is the clear, transparent anterior portion of the fibrous coat of the eye; it is important in light refraction and is covered with an epithelium that differs in many respects from the conjunctival epithelium.

The retina is the innermost, light sensitive portion of the eye, containing two types of photoreceptors, cones, which are responsible for color vision in brighter light, and rods, which are essential for vision in dim light but do not perceive colors. After light passes through the cornea, lens system, and the vitreous humor, it enters the retina from the inside; that is, it passes through the ganglion cells and nerve fibers, the inner and outer plexiform layers, the inner and outer nuclear layers, and the internal and external limiting membranes before it finally reaches the layer of photoreceptors located near the outside of the retina, just inside the outermost pigment epithelium layer. The cells of the pigment epithelium layer act as an anatomical barrier to liquids and substances located outside of the eye, forming the "blood-retina" barrier, and provide nourishment, oxygen, a source of functionally useful substances like vitamin A, and phagocytosis of decomposition products to photoreceptor cells. There is no anatomical connection between the pigment epithelium and the photoreceptor layer, permitting separation of the layers in some pathological situations.

When rods or cones are excited by light, signals are transmitted through successive neurons in the retina itself, into the optic nerve fibers, and ultimately to the cerebral cortex. Both rods and cones contain molecules that decompose on exposure to light and, in the process, excite the nerve fibers leading from the eye. The molecule in rods is rhodopsin. The three light-sensitive molecules in cones, collectively called iodopsin, have compositions only slightly different from that of rhodopsin and are maximally excited by red, blue, or green light, respectively.

Neither rods nor cones generate action potentials. Rather, the light-induced membrane hyperpolarization generated in the outer, photosensitive segment of a rod or cone cell is transmitted from the outer segment through the inner segment to the synaptic body by direct conduction of the electrical voltage itself, a process called electrotonic conduction. At the synaptic body, the membrane potential controls the release of an unknown transmitter molecule. In low light, rod and cone cell membranes are depolarized and the rate of transmitter release is greatest. Light-induced hyperpolarization causes a marked decrease in the release of transmitter molecules.

The transmitters released by rod and cone cells induce signals in the bipolar neurons and horizontal cells. The signals in both these cells are also transmitted by electrotonic conduction and not by action potential.

The rod bipolar neurons connect with as many as 50 rod cells, while the dwarf and diffuse bipolar cells connect with one or several cone cells. A depolarizing bipolar cell is stimulated when its connecting rods or cones are exposed to light. The release of transmitter molecules inhibits the depolarizing bipolar cell. Therefore, in the dark, when the rods and cones are secreting large quantities of transmitter molecules, the depolarizing bipolar cells are inhibited. In the light, the decrease in release of transmitter molecules from the rods and cones reduces the inhibition of the bipolar cell, allowing it to become excited. In this manner, both positive and negative signals can be transmitted through different bipolar cells from the rods and cones to the amacrine and ganglion cells.

As their name suggests, horizontal cells project horizontally in the retina, where they may synapse with rods, cones, other horizontal cells, or a combination of cells types. The function of horizontal cells is unclear, although some mechanism in the convergence of photoreceptor signaling has been postulated.

All types of bipolar cells connect with ganglion cells, which are of two primary types. A-type ganglion cells predominately connect with rod bipolar cells, while B-type ganglion cells predominately connect with dwarf and diffuse bipolar cells. It appears that A-type ganglion cells are sensitive to contrast, light intensity, and perception of movement, while B-type ganglion cells appear more concerned with color vision and visual acuity.

Like horizontal cells, the Amacrine cells horizontally synapse with several to many other cells, in this case bipolar cells, ganglion cells, and other Amacrine cells. The function of Amacrine cells is also unclear.

The axons of ganglion cells carry signals into the nerve fiber layer of the eye, where the axons converge into fibers which further converge at the optic disc, where they exit the eye as the optic nerve. The ganglion cells transmit their signals through the optic nerve fibers to the brain in the form of action potentials. These cells, even when unstimulated, transmit continuous nerve impulses at an average, baseline rate of about 5 per second. The visual signal is superimposed onto this baseline level of ganglion cell stimulation. It can be either an excitatory signal, with the number of impulses increasing above the baseline rate, or an inhibitory signal, with the number of nerve impulses decreasing below the baseline rate.

As part of the central nervous system, the eye is in some ways an extension of the brain; as such, it has a limited capacity for regeneration. This limited regeneration capacity further complicates the challenging task of improving vision, resolving dysfunction of the visual system, and/or treating or preventing ophthalmologic disorders. Many disorders of the eye, such as retinal photic injury, retinal ischemia-induced eye injury, age-related macular degeneration, free radical- induced eye diseases, as well as numerous other disorders, are considered to be entirely untreatable. Other ophthalmologic disorders, e.g., disorders causing permanent visual impairment, are corrected only by the use of ophthalmic devices and/or surgery, with varying degrees of success.

The immunosuppressant drugs FK506, rapamycin, and cyclosporin are well known as potent T-cell specific immunosuppressants, and are effective against autoimmunity, transplant or graft rejection, inflammation, allergic responses, other autoimmune or immune-mediated diseases, and infectious diseases. It has been disclosed that application of Cyclosporin, FK-506, Rapamycin, Buspirone, Spiperone, and/or their derivatives are effective in treating some ophthalmologic disorders of these types. Several ophthalmologic disorders or vision problems are known to be associated with autoimmune and immunologically-mediated activities; hence, immunomodulatory compounds are expected to demonstrate efficacy for treating those types of ophthalmologic disorders or vision problems.

The effects of FK506, Rapamycin, and related agents in the treatment of ophthalmologic diseases are disclosed in several U.S. patents (Goulet et al., U.S. Pat. No. 5,532,248; Mochizuki et al., U.S. Pat. No. 5,514,686; Luly et al., U.S. Pat. No. 5,457,111; Russo et al., U.S. Pat. No. 5,441,937; Kulkarni, U.S. Pat. No. 5,387,589; Asakura et al., U.S. Pat. No. 5,368,865; Goulet et al., U.S. Pat. No. 5,258,389; Armistead et al., U.S. Pat. No. 5,192,773; Goulet et al., U.S. Pat. No. 5,189,042; and Fehr, U.S. Pat. No. 5,011,844). These patents claim FK506 or kapamycin related compounds and disclose the known use of FK506 or kapamycin related compounds in the treatment of ophthalmologic disorders in association with the known immunosuppressive effects of FK506 and kapamycin. The compounds disclosed in these patents are relatively large. Further, the cited patents relate to immunomodulatory compounds limited to treating autoimmunity or related diseases, or immunologically-mediated diseases, for which the efficacy of FK506 and Rapamycin is well known.

Other U.S. patents disclose the use of cyclosporin, Spiperone, Buspirone, their derivatives, and other immunosuppressive compounds for use in the treatment of ophthalmologic diseases (Sharpe et al., U.S. Pat. No. 5,703,088; Sharpe et al., U.S. Pat. No. 5,693,645; Sullivan, U.S. Pat. No. 5,688,765; Sullivan, U.S. Patent No. 5,620,921; Sharpe et al., U.S. Pat. No. 5,574,041; Eberle, U.S. Pat. No. 5,284,826; Sharpe et al., U.S. Pat. No. 5,244,902; Chiou et al., U.S. Pat. Nos. 5,198,454 and 5,194,434; and Kaswan, U.S. Pat. No. 4,839,342). These patents also relate to compounds useful for treating autoimmune diseases and cite the known use of cyclosporin, Spiperone, Buspirone, their derivatives, and other immunosuppressive compounds in treating ocular inflammation and other immunologically-mediated ophthalmologic diseases.

The immunosuppressive compounds disclosed in the prior art suppress the immune system, by definition, and also exhibit other toxic side effects. Accordingly, there is a need for non-immunosuppressant, small molecule compounds, and compositions and methods for use of such compounds, that are useful in improving vision; preventing, treating, and/or repairing visual impairment or dysfunction of the visual system; and preventing, treating, and/or resolving ophthalmologic disorders.

There are also a number of patents on non-immunosuppressive compounds disclosing methods of use for permitting or promoting wound healing (whether from injury or surgery); controlling intraocular pressure (often resulting from glaucoma); controlling neurodegenerative eye disorders, including damage or injury to retinal neurons, damage or injury to retinal ganglion cells, and macular degeneration; stimulating neurite outgrowth; preventing or reducing oxidative damage caused by free radicals; and treating impaired oxygen and nutrient supply, as well as impaired waste product removal, resulting from low blood flow. These non-immunosuppressive substances fall into one of two general categories: naturally occurring molecules, such as proteins, glycoproteins, peptides, hormones, and growth factors; and synthetic molecules.

Within the group of naturally occurring non-immunosuppressive molecules, several hormones, growth factors, and signaling molecules have been patented for use as supplements to naturally occurring quantities of such molecules, as well as for targeting of specific cells where the particular molecule does not naturally occur in a mature individual. These patents generally claim methods of use for reducing or preventing the symptoms of ocular disease, or arresting or reversing vision loss.

Specifically, Louis et al., U.S. Pat. Nos. 5,736,516 and 5,641,749, disclose the use of a glial cell line derived neurotrophic factor (GDNF) to stop or reverse the degeneration of retinal neurons (i.e. photoreceptors) and retinal ganglion cells caused by glaucoma, or other degenerative or traumatic retinal diseases or injuries. O'Brien, et al., U.S. Pat. Nos. 5,714,459 and 5,700,909, disclose the use of a glycoprotein, Saposin, and its derivatives for stimulating neurite outgrowth and increasing myelination. To stop or reverse degeneration or retinal neurons, LaVail et al., U.S. Pat. No. 5,667,968, discloses the use of a variety of neurotrophic proteins, including brain-derived neurotrophic factor, ciliary neurotrophic factor, neurotrophin-3 or neurotrophin-4, acidic or basic fibroblast growth factors, interleukin, tumor necrosis factor-$\alpha$, insulin-like growth factor-2 and other growth factors. Wong et al., U.S. Pat. No. 5,632,984, discloses the use of interferons, especially interferon $\alpha$-2a, for treating the symptoms of macular degeneration by reducing hemorrhage and limiting neovascularization. Finally, Wallace et al., U.S. Pat. No. 5,441,937, discloses the use of a lung-derived neurotrophic factor (NTF) to maintain the functionality of ciliary ganglion and parasympathetic neuron cells.

A key characteristic of factors derived from specific cell lines is their localization to specific cell lines or tissues; systemic treatment with these molecules would run a substantial risk of unintended, and potentially dangerous, effects in cell lines where the genes encoding these molecules are inactive. Similarly, hormones and growth factors often activate a large number of genes in many cell lines; again, non-localized application of these molecules would run a substantial risk of provoking an inappropriate, and potentially dangerous, response.

Within the category of synthetic molecules, most of the patented compounds are immunosuppressive and disclose uses in treating inflammatory, autoimmune, and allergic responses, as discussed above. A few others are non-immunosuppressive and claim the ability to treat cellular degeneration, and in some cases promote cellular regeneration, most often in the context of their antioxidant properties.

Specifically, Tso et al., U.S. Pat. No. 5,527,533, discloses the use of astaxanthin, a carotenoid antioxidant, for preventing or reducing photoreceptor damage resulting from the presence of free radicals. Similarly, Babcock et al., U.S. Pat. No. 5,252,319, discloses the use of antioxidant aminosteroids for treating eye disease and injury, by increasing resistance to oxidative damage. Freeman, U.S. Pat. No. 5,468,752, discloses the use of the antiviral phosphonyl-methoxyalkylcytosines to reduce abnormally increased intraocular pressure.

Naturally occurring hormones, growth factors, cytokines, and signaling molecules are generally multifunctional and activate many genes in diverse cell lines. The present compounds do not, thus avoiding the unexpected, and potentially dangerous, side effects of systemic use. Similarly, the present compounds also avoid the potential unexpected side effects of introducing cell line-specific molecules into other cell lines were they do not naturally occur.

Hearing Loss Background

The epithelial hair cells in the organ of Corti of the inner ear, transduce sound into neural activity, which is transmitted along the cochlear division of the eighth cranial nerve. This nerve consists of fibers from three types of neurons (Spoendllin, H. H., in Friedmann, I. Ballantyne, J., eds. "Ultrastructural Atlas of the Inner Ear", London, Butterworth, pp. 133–164, (1984)) 1) afferent neurons, which lie in the spiral ganglion and connect the cochlea to the brainstem; 2) efferent olivocochlear neurons, which originate in the superior olivary complex; and 3) autonomic adrenergic neurons, which originate in the cervical sympathetic trunk and innervate the cochlea. In the human, there are approximately 30,000 afferent cochlear neurons, with myelinated axons, each consisting of about 50 lamellae, and 4–6 $\mu$m in diameter. This histologic structure forms the basis of uniform conduction velocity, which is an important functional feature. Throughout the length of the auditory nerve, there is a trophic arrangement of afferent fibers, with 'basal' fibers wrapped over the centrally placed 'apical' fibers in a twisted rope-like fashion. Spoendlin (Spoendlin, H. H. in Naunton, R. F., Fernadex, C. eds., "Evoked Electrical Activity in the Auditory Nervous System", London, Academic Press, pp. 21–39, (1978)) identified two types of afferent neurons in the spiral ganglion on the basis of morphologic differences: type I cells (95%) are bipolar and have myelinated cell bodies and axons that project to the inner hair cells. Type II cells (5%) are monopolar with unmyelinated axons and project to the outer hair cells of the organ of Cortd. Each inner hair cell is innervated by about 20 fibers, each of which synapses on only one cell. In contrast, each outer hair cell is innervated by approximately six fibers, and each fiber branches to supply approximately 10 cells. Within the cochlea, the fibers divide into: 1) an inner spiral group, which arises primarily ipsilaterally and synapses with the afferent neurons to the inner hair cells, and 2) a more numerous outer radial group, which arises mainly contralaterally and synapses directly with outer hair cells. There is a minimal threshold at one frequency, the characteristic or best frequency, but the threshold rises sharply for frequencies above and below this level (Pickles, J. C. in "Introduction to the Physiology of Hearing", London, Academic Press, pp. 71–106, (1982)). Single auditory nerve fibers therefore appear to behave as band-pass filters. The basilar membrane vibrates preferentially to different frequencies, at different distances along its length, and the frequency selectivity of each cochlear nerve fiber is similar to that of the inner hair cell to which the fiber is connected. Thus, each cochlear nerve fiber exhibits a tuning curve covering a different range of frequencies from its neighboring fiber (Evans, E. F. in Beagley H. A. ed., "Auditory investigation: The Scientific and Technological basis", New York, Oxford University Pressm (1979)). By this mechanism, complex sounds are broken down into component frequencies (frequency resolution) by the filters of the inner ear.

Impairment anywhere along the auditory pathway, from the external auditory canal to the central nervous system, may result in hearing loss. The auditory apparatus can be subdivided into the external and middle ear, inner ear and auditory nerve and central auditory pathways. Auditory information in humans is transduced from a mechanical signal to a neurally conducted electrical impulse by the action of approximately 15,000 epithelial cells (hair cells) and 30,000 first-order neurons (spiral ganglion cells) in the inner ear. All central fibers of spiral ganglion neurons form synapses in the cochlear nucleus of the pontine brainstem, The number of neurons involved in hearing increases dramatically from the cochlea to the auditory brain stem and the auditory cortex. All auditory information is transduced by only 15,000 hair cells, of which the so-called inner hair cells, numbering 3500, are critically important, since they from synapses with approximately 90 percent of the 30,000 primary auditory neurons. Thus, damage to a relatively few cells in the auditory periphery can lead to substantial hearing loss. Hence, most causes of sensorineural loss can be ascribed to lesions in the inner ear (Nadol, J. B., *New Englans Journal of Medicine*, (1993), 329:1092–1102).

Hearing loss can be on the level of conductivity, sensorineural and central level. Conductive hearing loss is caused by lesions involving the external or middle ear, resulting in the destruction of the normal pathway of airborne sound amplified by the tympanic membrane and the ossicles to the inner ear fluids. Sensorineural hearing loss is due to lesions of the central auditory pathways. These consist of the cochlear and dorsal olivary nucleus complex, inferior colliculi, medial geniculate bodies, auditory cortex in the temporal lobes and interconnecting afferent and efferent fiber tracts (Adams R. D. and Maurice, V., eds., in "Principles of Neurology", (1989), McGraw-Hill Information Services Company, pp. 226–246).

Trauma due to acoustic overstimulation is another leading cause of deafness. There is individual susceptibility to trauma from noise. Clinically important sensorineural hearing loss may occur in some people exposed to high-intensity noise, even below levels approved by the Occupational Safety and Health Agency (Osguthorpe, J. D., ed., Washington D.C., American Academy of Otolaryngology-Head and Neck Surgery Foundation, (1988)).

Demyelinating processes, such as multiple sclerosis, may cause sensorineural hearing loss (Noffsinger, D., et al., *Acto Otolaryngol. Suppl.* (Stockh.) (1972), 303:1–63). More recently, a form of immune-mediated sensorineural hearing loss has been recognized (McCabe, B. F., *Ann. Otol. Rhinol. Laryngol.* (1979), 88:585–9). The hearing loss is usually bilateral, is rapidly progressive (measured in weeks and months), and may or may not be associated with vestibular symptoms.

A variety of tumors, both primary and metastatic, can produce either a conductive hearing loss, or a sensorineural hearing loss, by invading the inner ear or auditory nerve (Houck, J. R., et al., *Otolaryngol. Head Neck Surg.* (1992), 106:92–7). A variety of degenerative disorders of unknown cause can produce sensorineural hearing loss. Meniere's syndrome (Nadol, J. B., ed., "Meniere's Disease: Pathogenesis, Pathophysiology, Diagnosis, And Treatment," Amsterdam: Kugler & Ghedini (1989)), characterized by fluctuating sensorineural hearing loss, episodic certigo, and tinnitus, appears to be caused by a disorder of fluid homeostasis within the inner ear, although the pathogenesis remains unknown. Sudden idiopathic sensorineural hearing loss (Wilson, W. R., et al., *Arch. Otolarynqol.* (1980), 106:772–6), causing moderate-to-severe sensorineural deafness, may be due to various causes, including inner ear ischemia and viral labyrinthitis.

Regardless of the cause, there exists a need to prevent or treat sensorineural hearing loss. The present invention provides such a method.

SUMMARY OF THE INVENTION

The present invention relates to the surprising discovery that N-heterocyclic compounds containing a carboxylic acid or carboxylic acid isostere moiety may be useful for treating neurological and/or neurodegenerative disorders, for treating alopecia and related hair loss disorders, for treating vision disorders and/or improving vision, for treating memory impairment and/or enhancing memory performance, and for treating sensorineural hearing loss. Accordingly, a novel class of compounds containing an acidic moiety or an isostere thereof attached to the 2-carbon of the N-heterocyclic ring is provided.

These compounds stimulate neuronal regeneration and outgrowth and as such are useful for treating neurological disorders and neurodegenerative diseases. These compounds also promote hair growth and as such are useful for treating hair loss disorders. These compounds also are useful for treating vision disorders, improving vision, treating memory impairment, enhancing memory performance, or treating hearing loss. A preferred feature of the compounds of the present invention is that they do not exert any significant immunosuppressive activity and/or are non-immunosuppressive.

A preferred embodiment of the invention is a pharmaceutical composition containing: a therapeutically effective amount of an N-heterocyclic carboxylic acid or carboxylic acid isostere compound; and a pharmaceutically suitable or acceptable carrier.

For pharmaceutical compositions directed specifically to neurotrophic medical indications, one or more additional neurotrophic factor(s) or neurotrophic agent(s) may be administered in combination with, or otherwise included in, the composition. Similarly pharmaceutical compositions directed specifically to hair loss related medical indications may also be administered in combination with an additional agent(s). Similarly pharmaceutical compositions directed specifically to vision disorder related medical indications may also be administered in combination with an additional agent(s). Similarly pharmaceutical compositions directed specifically to memory impairment related medical indications may also be administered in combination with an additional agent(s). Similarly pharmaceutical compositions directed specifically to hearing loss related medical indications may also be administered in combination with an additional agent(s).

A preferred method or use of the invention is a method of promoting neuronal regeneration and growth in mammals, comprising administering to a mammal an effective amount of an N-heterocyclic carboxylic acid or carboxylic acid isostere.

Another preferred method or use of the invention is a method of treating a neurological disorder in an animal, comprising administering to an animal an effective amount of an N-heterocyclic carboxylic acid or carboxylic acid isostere to stimulate growth of damaged peripheral nerves or to promote neuronal regeneration.

Yet another preferred method or use of the invention is a method of preventing neurodegeneration in an animal, comprising administering to an animal an effective amount of an N-heterocyclic carboxylic acid or carboxylic acid isostere.

Yet another preferred method or use of the invention is a method of stimulating growth of damaged peripheral nerves, comprising administering to a damaged peripheral nerve an effective amount of an N-heterocyclic carboxylic acid or carboxylic acid isostere.

Yet another preferred method or use of the invention is a method of treating alopecia or promoting hair growth in an animal, comprising administering to an animal an effective amount of an N-heterocyclic carboxylic acid or carboxylic acid isostere.

Yet another preferred embodiment of this invention is a method for treating a vision disorder, improving vision, treating memory impairment, or enhancing memory performance in an animal, comprising administering to an animal an effective amount of an N-heterocyclic carboxylic acid or carboxylic acid isostere.

Yet another preferred embodiment of this invention is a method for treating sensorineural hearing loss in an animal, comprising administering to an animal an effective amount of an N-heterocyclic carboxylic acid or carboxylic acid isostere.

The present invention further contemplates a process for preparing the an N-heterocyclic carboxylic acid or carboxylic acid isostere of the invention, comprising acidifying an intermediate compound.

The present invention further contemplates the compound(s) of the invention for use in treatment of a disease. In particular, the present invention contemplates the compound(s) of the invention for use in treatment of the disorders enumerated herein.

The invention further contemplates the compound(s) of the invention for use in the preparation of a medicament or pharmaceutical composition. in particular, the invention contemplates the compound(s) of the invention for use in the preparation of a medicament or pharmaceutical composition for treatment of the disorders enumerated herein.

The invention also provides for the use of compound(s) of the invention for treating a disease. In particular, the invention provides for the use of compound(s) of the invention for treating the disorders enumerated herein.

The invention also provides for the use of compound(s) of the invention in the manufacture of a medicament or pharmaceutical composition. In particular, the invention provides for the use of compound(s) of the invention in the manufacture of a medicament or pharmaceutical composition for the treatment of the disorders enumerated herein. Such pharmaceutical compositions include, as appropriate to the specific disorder, topical, systemic, oral or injectable formulations. It is further contemplated that the compound(s) of the invention may be administered with an effective amount of a second therapeutic agent for the treatment of the enumerated disorders. A variety of pharmaceutical formulations and different delivery techniques are described in further detail below.

A preferred compound of the invention is a compound of formula (I):

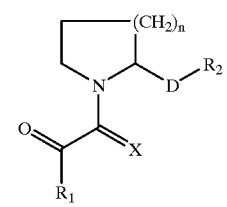

where
n is 1–3;
x is either O or S;
$R_1$ is selected from the group consisting of $C_1$–$C_9$ straight or branched chain alkyl, $C_2$–$C_9$ straight or branched chain alkenyl, aryl, heteroaryl, carbocycle, or heterocycle;
D is a bond, or a $C_1$–$C_{10}$ straight or branched chain alkyl, $C_2$–$C_{10}$ alkenyl or $C_2$–$C_{10}$ alkynyl;

$R_2$ is a carboxylic acid or a carboxylic acid isostere; and
wherein said alkyl, alkenyl, alkynyl, aryl, heteroaryl, carbocycle, heterocycle, or carboxylic acid isostere is optionally substituted with one or more substituents selected from $R^3$ and Z, where $R^3$ and Z are independently hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thloalkyl, alkylthio, sulfonyl, $C_1$–$C_6$ straight or branched chain alkyl, $C_2$–$C_6$ straight or branched chain alkenyl or alkynyl, aryl, aralkyl, heteroaryl, carbocycle, heterocycle, and $CO_2R^7$ where $R^7$ is hydrogen or $C_1$–$C_9$ straight or branched chain alkyl or $C_2$–$C_9$ straight or branched chain alkenyl;

or a pharmaceutically acceptable salt, ester, or solvate thereof;

provided that:
when n=1, and D is a bond, and $R_2$ is COOH,
then $R_1$ is not $C_1$–$C_9$ straight or branched chain alkyl, $C_2$–$C_9$ straight or branched chain alkenyl, $C_5$–$C_7$ cycloalkyl, $C_5$–$C_7$ cycloalkenyl, phenylamine, 2-(3,4-dichlorophenyl)ethyl, hydroxy, ethoxy, benzyl, or $Ar_1$, where $Ar_1$ is 1-naphthyl, 2-naphthyl, 2-indolyl, 3-indolyl, 2-furyl, 3-furyl, 2-thiazolyl, 2-thienyl, 3-thienyl, 1-pyridyl, 2-pyridyl, 3-pyridyl, 4-pyridyl, or phenyl, and wherein said alkyl, alkenyl, cycloalkyl, cycloalkenyl, or $Ar_1$ are optionally substituted with one or more substituents selected from the group consisting of hydrogen, halo, hydroxyl, nitro, trifluoromethyl, $C_1$–$C_9$ straight or branched alkyl, $C_2$–$C_9$ straight or branched alkenyl, $C_1$–$C_4$ alkoxy, $C_2$–$C_4$ alkenyloxy, phenoxy, benzyloxy, COOH, and amino;

further provided that:
when n=1, and D is a bond, and $R_2$ is the carboxylic acid isostere —CONZ($R^3$), and Z is hydrogen or $C_1$–$C_6$ alkyl, and $R^3$ is phenyl, or $C_2$–$C_6$ straight or branched chain alkyl or alkenyl, wherein said alkyl is unsubstituted or substituted in one or more positions with $Ar_2$ as defined below, $C_3$–$C_8$ cycloalkyl, cycloalkyl connected by methyl or a $C_2$–$C_6$ straight or branched chain alkyl or alkenyl chain, $C_1$–$C_4$ alkyl ester, or $Ar_3$ where $Ar_3$ is selected from the group consisting of 2-indolyl, 3-indolyl, 2-furyl, 3-furyl, 2-thiazolyl, 2-thienyl, 3-thienyl, 2-pyridyl, 3-pyridyl, 4-pyridyl, or phenyl, having one to three substituents independently selected from the group consisting of hydrogen, halo, hydroxy, nitro, trifluoromethyl, $C_1$–$C_6$ straight or branched alkyl, $C_2$–$C_6$ straight or branched alkenyl, $C_1$–$C_4$ alkoxy, $C_2$–$C_4$ alkenyloxy, phenoxy, benzyloxy, and amino; wherein said alkyl ester is optionally substituted with phenyl; or $R^3$ is the fragment:

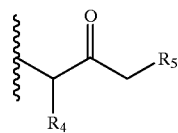

where $R^4$ is selected from the group consisting of straight or branched chain $C_1$–$C_8$ alkyl optionally substituted with $C_3$–$C_8$ cycloalkyl, benzyl, or $Ar_2$ as defined below, and where $R_2$ is COOZ or $CONR^6$, where $R^6$ is selected from the group consisting of hydrogen, $C_1$–$C_6$ straight or branched alkyl, and $C_2$–$C_6$ straight or branched alkenyl, and where $R_5$ is selected from the group consisting of phenyl, benzyl, $C_1$–$C_6$ straight or branched alkyl, and $C_2$–$C_6$ straight or branched alkenyl, where said alkyl or alkenyl is optionally substituted with phenyl;

then $R_1$ is not $C_1$–$C_9$ straight or branched chain alkyl, $C_2$–$C_9$ straight or branched chain alkenyl, substituted thiophene, or $C_1$–$C_4$ alkoxy, wherein said alkyl or alkenyl is optionally substituted in one or more positions with $C_3$–$C_8$ cycloalkyl, $C_5$–$C_7$ cycloalkenyl, or $Ar_2$, where $Ar_2$ is defined below, where said alkyl, alkenyl, cycloalkyl or cycloalkenyl groups may be optionally substituted with $C_1$–$C_4$ alkyl, $C_1$–$C_4$ alkenyl, or hydroxy, and where $Ar_2$ is 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, or phenyl, having one to three substituents selected from the group consisting of hydrogen, halo, hydroxy, nitro, trifluoromethyl, $C_1$–$C_6$ straight or branched alkyl, $C_2$–$C_6$ straight or branched alkenyl, $C_1$–$C_6$ alkoxy, $C_2$–$C_4$ alkenyloxy, phenoxy, benzyloxy, and amino;

further provided that:
when n=1, and X is O, and D is a bond, and $R_2$ is —$CONH_2$,
then $R_1$ is not methyl, ethyl, iso-propyl, iso-butyl, iso-pentyl, 4-merhylpentyl, indolyl, phenyl, or hydroxyphenyl;

further provided that:
when n=1, and X is O, and D is a bond, and $R_2$ is cyano,
then $R_1$ is not methyl;

further provided that:
when n=2, and X is O, and D is a bond, and $R_2$ is CONZ($R^3$), and $R_1$ is ethoxy, then $R^3$ or Z is not halo-substituted phenyl;

further provided that:
when n=2, and X is O, and D is a bond, and $R_2$ is CONZ($R^3$) and $R_1$ is substituted thiophene or tetrahydropyranoxy, or methoxy, then $R^3$ or Z is not $C_1$–$C_4$ alkyl ester substituted ethyl;

further provided that:
when n=2, and X is O, and D is a bond, and $R_2$ is CONZ($R^3$) and $R_1$ is ethoxy, then $R^3$ or Z is not 4-chlorophenyl;

further provided that:
when n=2, and X is O, and D is a bond, and $R_2$ is CONZ($R^3$) and $R_1$ is cyclohexyl, then $R^3$ or Z is not ethyl or propyl substituted with phenyl;

further provided that:
when D is $CH_2$, then $R_2$ is not —OMe, —NHMe, or substituted —NHcyclohexyl;

further provided that:
when D is CH,, and R is —OH,
then $R_1$ is not phenyl or pyrrolidinemethanol;

further provided that:
when n=2, and X is O, and D is a bond, and $R_2$ is COOH,
then $R_1$ is not methyl, tert-butyl, 1,1-dimethyl-2-methylpropyl, 1,1-dimethyl-propyl, methoxy, ethoxy, phenyl, tetrahydropyranoxy substituted $C_4$–$C_6$ alkyl, 1-methyl-1-methoxyamide, 1-methylcyclohexyl, 3-iodophenyl, 3-methyl ester-cyclopentyl, 1,1-dimethyl-6-phenyl-hex-3,5-dioxy, or trimethoxyphenyl.

Preferred embodiments of this invention are where PR is a carbocycle or heterocycle containing any combination of $CH_2$, O, S, or N in any chemically stable oxidation state, where any of the atoms of said ring structure are optionally substituted in one or more positions with $R^3$.

Especially preferred embodiments of this invention are where $R_2$ is selected from the group below:

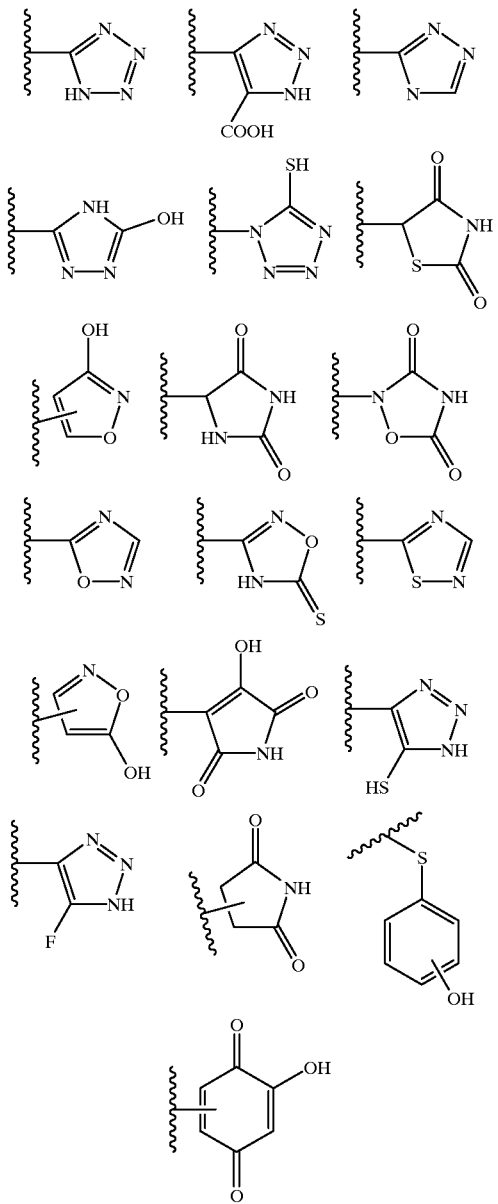

where the atoms of said ring structure may be optionally substituted at one or more positions with R³.

Another preferred embodiment of this invention is where R₂ is selected from the group consisting of —COOH, —SO₃H, —SO₂HNR³, —PO₃(R³)₂, —CN, —PO₃(R³)₂, —OR³, —SR³, —NHCOR³, —N(R³)₂, —CON(O)R³)₂, —CONH(O)R³, —CONHNHSO₂R³, —COHNSO₂R³, and —CONR³CN.

Preferred embodiments of this invention are:
(2S)-1-(1,2-dioxo-3,3-dimethylpentyl)-2-hydroxymethyl pyrrolidine;
(2S)-1-(1,2-dioxo-3,3-dimethylpentyl)-2-pyrrolidine tetrazole;
(2S)-1-(1,2-dioxo-3,3-dimethylpentyl)-2-pyrrolidine carbonitrile;
(2S)-1-(1,2-dioxo-3,3-dimethylpentyl)-2-aminocarbonyl piperidine;
[1-(3,3-Dimethyl-2-oxopentanoyl)pyrrolidin-2-yl]-N-(2-thienylcarbonylamino)-formamide;
3,3-Dimethyl-1-{2-[(4-nitrophenoxy)methyl]pyrrolidinyl}pentane-1,2-dione;
2-[1-(3,3-Dimethyl-2-oxopentanoyl)pyrrolidin-2-yl]ethane nitrile;
1-[2-(3-Ethyl(1,2,4-oxadiazol-5-yl))pyrrolidinyl]-3,3-dimethylpentane-1,2-dione;
1-{2-[3-(4-Fluorophenyl)(1,2,4-oxadiazol-5-yl)]pyrrolidinyl}-3,3-dimethylpent-ane-1,2-dione;
3,3-Dimethyl-1-[2-(3-methyl(1,2,4-oxadiazol-5-yl))pyrrolidinyl]pentane-1,2-dione;
[1-(3,3-Dimethyl-2-oxopentanoyl)pyrrolidin-2-yl]-N-[(methylsulfonyl)amino]-formamide;
[1-(3,3-Dimethyl-2-oxopentanoyl)pyrrolidin-2-yl]-N-{[(4-methylphenyl)sulfonyl]-amino}formamide;
[1-(3,3-Dimethyl-2-oxopentanoyl)pyrrolidin-2-yl]-N-{[(4-fluorophenyl)sulfonyl]-amino}formamide;
1-[Benzylsulfonyl]-2-(pyrrolidinylmethyl)pyrrolidine;
(2S)-3,3-Dimethyl-1-[2-(5-sulfanyl(4H-1,2,4-triazol-3-yl))pyrrolidinyl]-pentane-1,2-dione;
(2S)-3,3-Dimethyl-1-[2-(pyrrolidinylmethyl)pyrrolidinyl]pentane-1,2-dione;
(2S)-N-[(Aminothioxomethyl)amino][1-(3,3-dimethyl-2-oxopentanoyl)pyrrolid-in-2-yl]formamide;
(2S)-1-[2-(Benzotriazol-1-ylcarbonyl)pyrrolidinyl]-3,3-dimethylpentane-1,2-dione;
N-Amino-2-[2-(N-aminocarbamoyl)pyrrolidinyl]-2-oxoethanamide;
2-[1-(3,3-Dimethyl-2-oxopentanoyl)-2-piperidyl]acetic acid;
1-(2-{[4-(2H-Benzo[3,4-d]1,3-dioxolen-5-ylmethyl)piperazinyl]carbonyl}pyrrol-idinyl)-3,3-dimethylpentane-1,2-dione; and,
1-[2-({4-[Bis(4-fluorophenyl)methyl]piperazinyl}carbonyl)pyrrolidinyl]-3,3-di-methylpentane-1,2-dione.

BRIEF DESCRIPTION OF THE DRAWINGS

FIG. 2 shows that less than 3% of the shaved area is covered with new hair growth when the vehicle (control) is administered.

DETAILED DESCRIPTION OF THE INVENTION

Definitions

Figure 1:
FIG. 1 is a photograph of C57 Black 6 mice before being shaved for the hair regeneration experiment.

"Alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like. It is also contemplated as within the scope of the present invention that "alkyl" may also refer to a hydrocarbon chain wherein any of the carbon atoms of said alkyl are optionally replaced with O, NH, S, or $SO_2$. For example, carbon 2 of n-pentyl can be replaced with O to form propyloxymethyl.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like. It is also contemplated as within the scope of the present invention that "alkenyl" may also refer to an unsaturated hydrocarbon chain wherein any of the carbon atoms of said alkenyl are optionally replaced with O, NH, S, or $SO_2$. For example, carbon 2 of 4-pentene can be replaced with O to form (2-propene)oxymethyl.

"Alkoxy" means the group —OR wherein R is alkyl as herein defined. Preferably, R is a branched or unbranched saturated hydrocarbon chain containing 1 to 6 carbon atoms.

Specifically, the term "carbocycle" or refers to an organic cyclic moiety in which the cyclic skeleton is comprised of only carbon atoms whereas the term "heterocycle" refers to an organic cyclic moiety in which the cyclic skeleton contains one or more heteroatoms selected from nitrogen, oxygen, or sulfur and which may or may not include carbon atoms.

Thus, the term "carbocycle" refers to a carbocyclic moiety containing the indicated number of carbon atoms. The term "$C_3$–$C_8$ cycloalkyl", therefore, refers to an organic cyclic substituent in which three to eight carbon atoms form a three, four, five, six, seven, or eight-membered ring, including, for example, a cyclopropyl, cyclobuty;, cyclopentyl, cyclohexyl, cycloheptyl, or cyclooctyl ring. As used herein, "carbocycle" may also refer to two or more cyclic ring systems which are fused to form, for example bicyclic, tricyclic, or other similar bridged substituents (e.g. adamantyl).

"Aryl" refers to an aromatic carbocyclic group having a single ring, for example a phenyl ring; multiple rings, for example biphenyl; or multiple condensed rings in which at least one ring is aromatic, for example naphthyl, 1,2,3,4-tetrahydronaphthyl, anthryl, or phenanthryl, which can be unsubstituted or substituted with one or more other substituents as defined above. The substituents attached to a phenyl ring portion of an aryl moiety in the compounds of Formula (I) may be configured in the ortho-, meta-, or para-orientations.

Examples of typical aryl moieties included in the scope of the present invention may include, but are not limited to, the following:

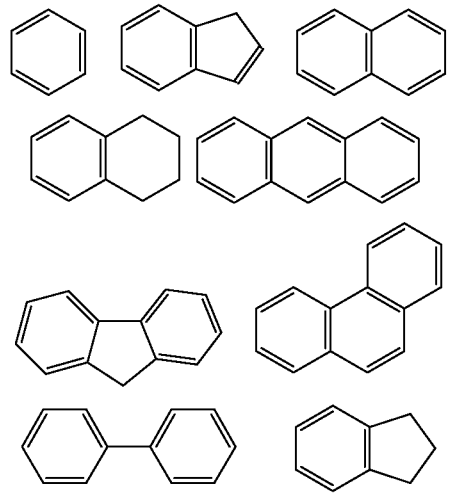

"Aralkyl" refers to alkyl or alkylene (alkenyl) chain which is substituted with aryl, heteroaryl, carbocycle or heterocycle, or alternatively one or more aryl, heteroaryl, carbocycle, or heterocycle(s) which is/are substituted with alkyl or alkenyl, i.e. 'Alkyl/alkylene which is substituted with Ar' or 'Ar which is substituted with alkyl/alkylene'.

"Heterocycle" refers to a saturated, unsaturated, or aromatic carbocyclic group having a single ring, multiple rings, or multiple condensed rings, and having at least one hetero atom such as nitrogen, oxygen, or sulfur within at least one of the rings. "Heteroaryl" refers to a heterocycle in which at least one ring is aromatic. Any of the heterocyclic or heteroaryl groups can be unsubstituted or optionally substituted with one or more groups as defined above. Further, bi- or tri-cyclic heteroaryl moieties may comprise at least one ring which is either completely or partially saturated.

As one skilled in the art will appreciate, such heterocyclic moieties may exist in several isomeric forms, all of which are encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the present invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

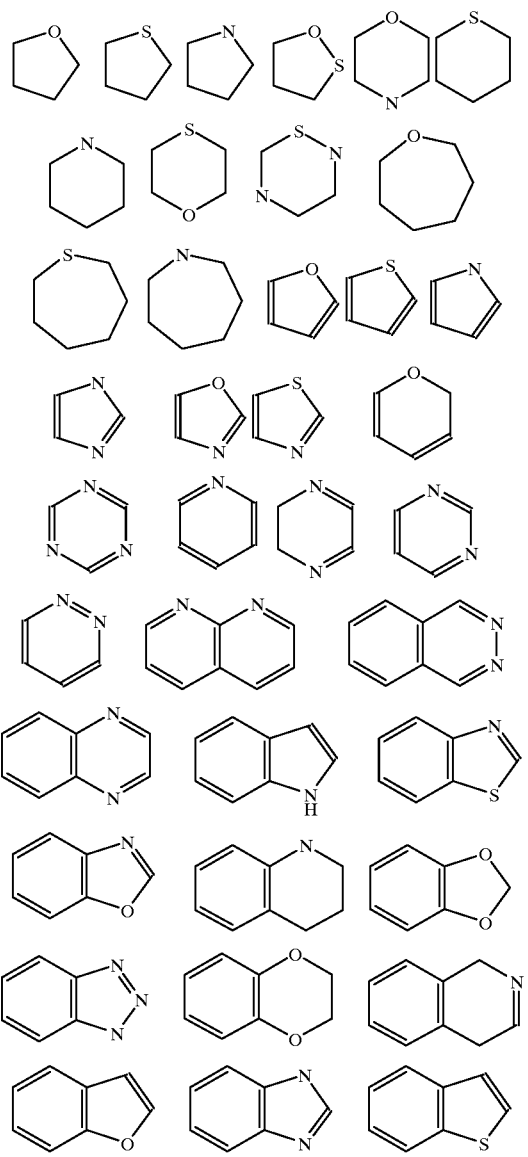

"Halo" means at least one fuoro, chloro, bromo, or iodo moiety.

The term "pharmaceutically acceptable salt, ester, or solvate" refers to salt, ester, or solvates of the subject compounds which possess the desired pharmacological activity and which are neither biologically nor otherwise undesirable. The salt, ester, or solvates can be formed with inorganic or organic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Base salt, ester, or solvates include ammonium salts, alkali metal salts such as lithium, sodium and potassium salts, alkaline earth metal salts such as calcium and magnesium salts, salt with organic bases such as dicyclo-hexylamine salts, N-methyl-D-glucamine, and salts with amino acids such as arginine, lysine, and so forth. Also, the basic nitrogen-containing groups can be quarternized with such agents as: 1) lower alkyl halides, such as methyl, ethyl, propyl, and butyl chloride, bromides and iodides; 2) dialkyl sulfates like dimethyl, diethyl, dibutyl and diamyl sulfates; 3) long chain alkyls such as decyl, lauryl, myristyl and stearyl substituted with one or more halide such as chloride, bromide and iodide; and 4) aralkyl halides like benzyl and phenethyl bromide and others.

The compounds of this invention may possess at least one asymmetric center and thus can be produced as mixtures of stereoisomers or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is a most preferred embodiment of the invention.

"Stereoisomers" are isomers that differ only in the way the atoms are arranged in space.

"Isomers" are different compounds that have the same molecular formula and includes cyclic isomers such as (iso)indole and other isomeric forms of cyclic moieties.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

"Isosteres" are different compounds that have different molecular formulae but exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated by the present invention include —COOH, —SO$_3$H, —SO$_2$HNR$^3$, —PO$_2$(R$^3$)$_2$, —CN, —PO$_3$(R$^3$)$_2$, —OR$^3$, —SR$^3$, —NHCOR$^3$, —N(R$^3$)$_2$, —CON(R$^3$)$_2$, —CONH(O)R$^3$, —CONHNHSO$_2$R$^3$, —COHNSO$_2$R$^3$, and —CONR$^3$CN. In addition, carboxylic acid isosteres can include 5–7 membered carbocycles or heterocycles containing any combination of CH$_2$, O, S, or N in any chemically stable oxidation state, where any of the atoms of said ring structure are optionally substituted in one or more positions. The following structures are non-limiting examples of preferred carbocyclic and heterocyclic isosteres contemplated by this invention.

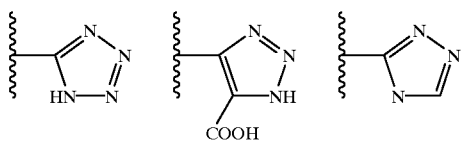

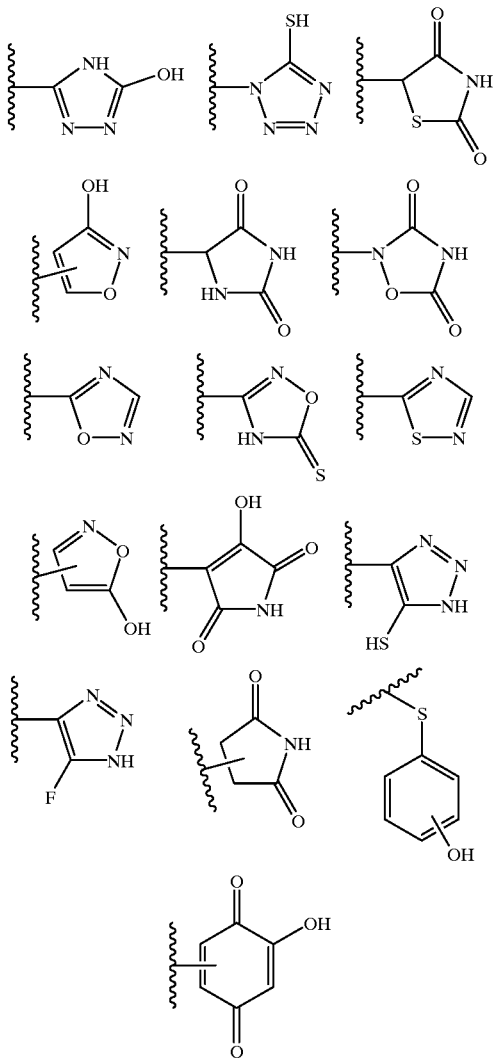

where the atoms of said ring structure may be optionally substituted at one or more positions with $R^3$. The present invention contemplates that when chemical substituents are added to a carboxylic isostere then the inventive compound retains the properties of a carboxylic isostere. The present invention contemplates that when a carboxylic isostere is optionally substituted with one or more moieties selected from $R^3$, then the substitution cannot eliminate the carboxylic acid isosteric properties of the inventive compound. The present invention contemplates that the placement of one or more $R^3$ substituents upon a carbocyclic or heterocyclic carboxylic acid isostere shall not be permitted at one or more atom(s) which maintain(s) or is/are integral to the carboxylic acid isosteric properties of the inventive compound, if such substituent(s) would destroy the carboxylic acid isosteric properties of the inventive compound.

Other carboxylic acid isosteres not specifically exemplified or described in this specification are also contemplated by the present invention.

It is understood that where chemical substitution is indicated then the chemical substituent chosen would form a sufficiently stable compound.

The term "preventing neurodegeneration" as used herein includes the ability to inhibit or prevent neurodegeneration in patients newly diagnosed as having a neurodegenerative disease, or at risk of developing a new degenerative disease and for inhibiting or preventing further neurodegeneration in patients who are already suffering from or have symptoms of a neurodegenerative disease when the compounds are given concurrently.

The term "treatment" as used herein covers any treatment of a disease and/or condition in an animal, particularly a human, and includes:
  (i) preventing a disease and/or condition from occurring in a subject which may be predisposed to the disease and/or condition but has not yet been diagnosed as having it;
  (ii) inhibiting the disease and/or condition, i.e., arresting its development; or
  (iii) relieving the disease and/or condition, i.e., causing regression of the disease and/or condition.

The system used in naming the compounds of the present invention is shown below, using a compound of formula I as an example.

A compound of the present invention, especially formula I, wherein n is 1, X is O, D is a bond, $R_1$ is 1,1-dimethylpropyl, and $R_2$ is —CN, is named (2S)-1-(1,2-dioxo-3,3-dimethylpentyl)-2-pyrrolidinecarbonitrile.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"Pilar cycle" refers to the life cycle of hair follicles, and includes three phases:
  (1) the anagen phase, the period of active hair growth which, insofar as scalp hair is concerned, lasts about three to five years;
  (2) the catagen phase, the period when growth stops and the follicle atrophies which, insofar as scalp hair is concerned, lasts about one to two weeks; and
  (3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Treating alopecia" refers to:
  (i) preventing alopecia in an animal which may be predisposed to alopecia; and/or
  (ii) inhibiting, retarding or reducing alopecia; and/or
  (iii) promoting hair growth; and/or
  (iv) prolonging the anagen phase of the hair cycle; and/or
  (v) converting vellus hair to growth as terminal hair. Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

"Eye" refers to the anatomical structure responsible for vision in humans and other animals, and encompasses the following anatomical structures, without limitation: lens, vitreous body, cilary body, posterior chamber, anterior chamber, pupil, cornea, iris, canal of Schlemm, zonules of Zinn, limbus, conjunctiva, choroid, retina, central vessels of the retina, optic nerve, fovea centralis, macula lutea, and sclera.

"Neopsic factors" or "neopsics" refers to compounds useful in treating vision loss, preventing vision degeneration, or promoting vision regeneration.

"Neopsis" refers to the process of treating vision loss, preventing vision degeneration, or promoting vision regeneration.

"Ophthalmological" refers to anything about or concerning the eye, without limitation, and is used interchangeably with "ocular," "ophthalmic," "ophthalmologic," and other such terms, without limitation.

"Preventing vision degeneration" as used herein includes the ability to prevent degeneration of vision in patients newly diagnosed as having a degenerative disease affecting vision, or at risk of developing a new degenerative disease affecting vision, and for preventing further degeneration of vision in patients who are already suffering from or have symptoms of a degenerative disease affecting vision.

"Promoting vision regeneration" refers to maintaining, improving, stimulating or accelerating recovery of, or revitalizing one or more components of the visual system in a manner which improves or enhances vision, either in the presence or absence of any ophthalmologic disorder, disease, or injury.

"Vision", as used herein, refers to the ability of humans and other animals to process images, and is used interchangeably with "sight", "seeing", and other such terms, without limitation.

"Vision disorder" refers to any disorder that affects or involves vision, including without limitation visual impairment, orbital disorders, disorders of the lacrimal apparatus, disorders of the eyelids, disorders of the conjunctiva, disorders of the cornea, cataracts, disorders of the uveal tract, disorders of the optic nerve or visual pathways, free radical induced eye disorders and diseases, immunologically-mediated eye disorders and diseases, eye injuries, and symptoms and complications of eye disease, eye disorder, or eye injury.

"Visual impairment" refers to any dysfunction in vision including without limitation disturbances or diminution in vision (e.g., binocular, central, peripheral, scotopic), visual acuity for objects near and for, visual field, ocular motility, color perception, adaptation to light and dark, accommodation, refraction, and lacrimation. See Physicians' Desk Reference (PDR) for Ophthalmology, 16th Edition, 6:47 (1988).

"Enhancing memory performance" refers to improving or increasing the mental faculty by which to register, retain or recall past experiences, knowledge, ideas, sensations, thoughts or impressions.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, and drug intoxications. Examples of memory impairment include, without limitation, benign forgetfulness, amnesia and any disorder in which memory deficiency is present, such as Korsakoff's amnesic psychosis, dementia and learning disorders.

The term "middle-ear" refers to the space between the tympanic membrane and the inner ear. This location is external to all inner ear tissue and an invasive procedure might not be required to access this region if a formulation capable of penetrating through the tympanic membrane is administered. Otherwise, the material will be introduced to the middle ear by injection through the tympanic membrane or, in case repeated administrations are needed, a hole can be made in the tympanic membrane. An opening in the tympanic membrane is a frequent procedure, performed on an office-visit basis, in cases such as infections of the middle ear (usually in children). The opening generally closes spontaneously after a few days.

The term "neurotrophic" as used herein includes without limitation the ability to stimulate neuronal regeneration or growth and/or the ability to prevent or treat neurodegeneration.

The term "non-immunosuppressive" refers to the inability of the compounds of the present invention to trigger an immune response when compared to a control such as FK506 or cyclosporin A. Assays for determining immunosuppression are well known to those of ordinary skill in the art. Specific non-limiting examples of well known assays include PMA and OKT3 assays wherein mitogens are used to stimulate proliferation of human peripheral blood lymphocytes (PBC). Compounds added to such assay systems are evaluated for their ability to inhibit such proliferation.

The term "small molecule" refers to the molecular weight of the compounds of the invention as compared to FK506. Thus, the term "small molecule" includes molecular weights less than about 800 Daltons (m.w.), and novel subranges or limits below the same including about 100 to about 750 m.w., about 150 to about 500 m.w., about 150 to about 350 m.w., about 200 to about 300 m.w., about 210 to about 280 m.w., about 220 to about 260, and about 240 m.w. The term "spatially small molecule" refers to the capability of the compounds to fit entirely or substantially within the binding cavity of FKBP-12 as compared to FK506.

Utility of the Compounds of the Invention

The present invention relates to the surprising discovery that carboxylic acid or carboxylic acid isostere compounds are neurotrophic, are able to treat alopecia, are able to treat vision and memory disorders, and are able to treat sensorineural hearing loss. Accordingly, a novel class of compounds are provided. A preferred feature of the compounds of the present invention is that they do not exert any significant immunosuppressive activity.

Preferred compounds of the present invention contain carboxylic acid moieties and other isosteric replacements for carboxylic acid moieties, of which several examples are specified herein. Other isosteric replacements for carboxylic acid moieties, known to those skilled in the art of medicinal chemistry, are within the scope of the invention if not otherwise specified.

The compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertebrate disk syndromes, cervical spondylosis, plexus disorders, thoracic outlet destruction syndromes, peripheral neuropathic such as those caused by lead, dapsone, ticks, prophyria, or Gullain-Barrésyndrome, multiple sclerosis, stroke and ischemia associate with stroke, neural paropathy, other neurodegenerative diseases, motor neuron diseases, sciatic crush, peripheral neuropathy, particularly neuropathy associate with diabetes, spinal cord injuries and facial nerve crush, Huntington's Disease, Alzheimer's disease, and Parkinson's disease.

The above discussion relating to the utility and administration of the compounds of the present invention also applies to the pharmaceutical compositions of the present invention.

The term "pharmaceutically acceptable carrier" as used herein refers to any carrier, diluent, excipient, suspending agent, lubricating agent, adjuvant, vehicle, delivery system, emulsifier, disintegrant, absorbant, preservative, surfactant, colorant, flavorant, or sweetener.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

For oral administration, the compounds of the present invention may be provided in any suitable dosage form known in the art. For example, the compositions may be incorporated into tablets, powders, granules, beads, chewable lozenges, capsules, liquids, aqueous suspensions or solutions, or similar dosage forms, using conventional equipment and techniques known in the art. Tablet dosage forms are preferred. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, poly-vinyl alcohol, and the like; absorbents, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

Compositions and methods of the invention also may utilize controlled release technology. Thus, for example, the inventive compounds may be incorporated into a hydrophobic polymer matrix for controlled release over a period of days. Such controlled release films are well known to the art. Particularly preferred are transdermal delivery systems. Other examples of polymers commonly employed for this purpose that may be used in the present invention include nondegradable ethylene-vinyl acetate copolymer and degradable lactic acid-glycolic acid copolymers which may be used externally or internally. Certain hydrogels such as poly(hydroxyethylmethacrylate) or poly(vinylalcohol) also may be useful, but for shorter release cycles then the other polymer releases systems, such as those mentioned above.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration. Typically, in vitro dosage-effect results provide useful guidance on the proper doses for patient administration. Studies in animal models are also helpful. The considerations for determining the proper dose levels are well known in the art.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

To effectively treat alopecia or promote hair growth, the compounds used in the inventive methods and pharmaceutical compositions must readily affect the targeted areas. For these purposes, the compounds are preferably administered topically to the skin.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

The compounds can be administered with other hair revitalizing agents. Specific dose levels for the other hair revitalizing agents will depend upon the factors previously stated and the effectiveness of the drug combination. Other routes of administration known in the pharmaceutical art are also contemplated by this invention.

Pharmaceutical Compositions of the Present Invention

The present invention relates to a pharmaceutical composition comprising:
(i) an effective amount of an N-heterocyclic carboxylic acid or carboxylic acid isostere compound; and
(ii) a pharmaceutically acceptable carrier.
The present invention also relates to a pharmaceutical composition comprising:

(i) an effective amount of an N-heterocyclic carboxylic acid or carboxylic acid isostere compound for treating neurodegenerative diseases, neurological disorders, and nerve damage, or promoting nerve growth in an animal; and
(ii) a pharmaceuticaliy acceptable carrier.

The present invention also relates to a pharmaceutical composition comprising:
(i) an effective amount of an N-heterocyclic carboxylic acid or carboxylic acid isostere compound for treating alopecia or promoting hair growth in an animal; and
(ii) a pharmaceutically acceptable carrier.

The present invention also relates to a pharmaceutical composition comprising:
(i) an effective amount of an N-heterocyclic carboxylic acid or carboxylic acid isostere compound for treating a vision disorder, improving vision, treating memory impairment, or enhancing memory performance in an animal; and
(ii) a pharmaceutically acceptable carrier.

The present invention also relates to a pharmaceutical composition comprising:
(i) an effective amount of an N-heterocyclic carboxylic acid or carboxylic acid isostere compound for treating sensorineural hearing loss in an animal; and
(ii) a pharmaceutically acceptable carrier.

For pharmaceutical compositions directed specifically to neurotrophic medical indications, one or more additional neurotrophic factor(s) or neurotrophic agent(s) may be administered in combination with, or otherwise included in, the composition. The compounds can be administered with other neurotrophic agents such as neurolrophic growth factor, brain derived growth factor, glial derived growth factor, cilial neurotrophic factor, insulin growth factor and active truncated derivatives thereof, acidic fibroblast growth factor, basic fibroblast growth factor, platelet-derived growth factors, neurotropin-3 and neurotropin 4/5. The dosage level of other neurotrophic drugs will depend upon the factors previously stated and the neurotrophic effectiveness of the drug combination.

Similarly pharmaceutical compositions directed specifically to hair loss related medical indications may also be administered in combination with an additional agent(s).

Methods of the Present Invention

The present invention relates to the use of any of the compounds seen in Tables I, II, III, IV, other compounds embodied herein, and other compounds not specifically mentioned or described herein, in the preparation of a medicament.

These medicaments or formulations are useful in methods for the treatment of a disease such as peripheral neuropathy caused by physical injury or disease state, physical damage to the brain, physical damage to the spinal cord, stroke associated with brain damage, Huntington's Disease, Alzheimer's Disease, Parkinson's Disease, amyotrophic lateral sclerosis, and Huntington's Disease. The present invention also relates to the use of carboxylic acid and carboxylic acid isostere compounds in methods for treating the above-mentioned neuropathies, neurological disorders, and neurological damage.

The present invention also relates to using the inventive compounds and compositions in the preparation of a medicament for the treatment of alopecia or promoting hair growth in an animal. The present invention also relates to the use in a method for treating alopecia or promoting hair growth in an animal, which comprises administering to said animal an effective amount of an N-heterocyclic carboxylic acid or carboxylic acid isostere.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

The present invention also relates to a method for treating a vision disorder, improving vision, treating memory impairment, or enhancing memory performance in an animal, which comprises administering to said animal an effective amount of N-hererocyclic carboxylic acid or carboxylic acid isostere. The present invention also relates to using the inventive compounds and compositions in the preparation of a medicament for the treatment of a vision disorder, improving vision, treating memory impairment, or enhancing memory performance.

The inventive methods are particularly useful for treating various eye disorders including, but not limited to visual disorders, diseases, injuries, and complications, genetic disorders; disorders associated with aging or degenerative vision diseases; vision disorders correlating to physical injury to the eye, head, or other parts of the body resulting from external forces; disorders resulting from environmental factors; disorders resulting from a broad range of diseases; and combinations of any of the above.

In particular, the compositions and methods of the present invention are useful for improving vision, or correcting, treating, or preventing visual (ocular) impairment or dysfunction of the visual system, including permanent and temporary visual impairment, without limitation. The present invention is also useful in preventing and treating ophthalmologic diseases and disorders, treating damaged and injured eyes, and preventing and treating diseases, disorders, and injuries which result in vision deficiency, vision loss, or reduced capacity to see or process images, and the symptoms and complications resulting from same. The eye diseases and disorders which may be treated or prevented by the compositions and methods of the present invention are not limited with regard to the cause of said diseases or disorders. Accordingly, said compositions and methods are applicable whether the disease or disorder is caused by genetic or environmental factors, as well as any other influences. The compositions and methods of the present invention are particularly useful for eye problems or vision loss or deficiency associated with all of the following, without limitation: aging, cellular or physiological degeneration, central nervous system or neurological disorder, vascular defects, muscular defects, and exposure to adverse environmental conditions or substances.

The compositions and methods of the present invention are particularly useful in correcting, treating, or improving visual impairment, without limitation. Visual impairment in varying degrees occurs in the presence of a deviation from normal in one or more functions of the eye, including (1) visual acuity for objects at distance and near; (2) visual fields; and (3) ocular motility without diplopia. See *Physicians' Desk Reference (PDR) for Ophthalmology*, 16th Edition, 6:47 (1988). Vision is imperfect without the coordinated function of all three. Id.

Said compositions and methods of use are also useful in correcting, treating, or improving other ocular functions including, without limitation, color perception, adaptation to light and dark, accommodation, metamorphopsia, and binocular vision. The compositions and methods of use are particularly useful in treating, correcting, or preventing ocular disturbances including, without limitation, paresis of accommodation, iridoplegia, entropion, ectropion, epiphora, lagophthalmos, scarring, vitreous opacities, non-reactive pupil, light scattering disturbances of the cornea or other media, and permanent deformities of the orbit.

The compositions and methods of use of the present invention are also highly useful in improving vision and treating vision loss. Vision loss ranging from slight loss to absolute loss may be treated or prevented using said compositions and methods of use. Vision may be improved by the treatment of eye disorders, diseases, and injuries using the compositions and methods of the invention. However, improvements in vision using the compositions and methods of use are not so limited, and may occur in the absence of any such disorder, disease, or injury.

The compositions and methods of the present invention are also highly useful in preventing and/or treating sensorineural hearing loss in a patient. According to one aspect of the invention, methods are provided for treating damaged hair cells and auditory neurons.

It is further contemplated that administration of an inventive compound will protect hair cells and spiral ganglion neurons from traumatic damage, for example damage caused by noise trauma, acute or chronic treatment with cisplatin and aminoglycoside antibiotics of from damage resulting from a lack of neurotrophic factors resulting from interruption of transport of the factors from the axon to the cell body. Such treatment is expected to allow hair cells and/or auditory neurons to tolerate intermittent insults from either environmental noise trauma or treatment with ototoxins, and to slow down, prevent or reverse the progressive degeneration of the auditory neurons and hair cells which is responsible for hearing loss in pathological conditions such as presbycusis (age-related hearing loss), inherited sensorineural degeneration, and post-idiopathic hearing losses and to preserve the functional integrity of the inner ear. Such treatment will also support the auditory neurons for better and longer performance of cochlear implants.

It is understood, however, that a specific dose level for any particular patient will depend upon a variety of factors including the activity of the specific compound employed, the age, body weight, general health, sex, diet, time of administration, rate of excretion, drug combination, and the severity of the particular disease or disorder being treated and form of administration.

Preferred Compounds of the Invention

Specific embodiments of the inventive compounds are presented in Tables I, II, and III. The present invention contemplates employing the compounds of Tables I, II and III, below, for use in compositions and methods to prevent and/or treat a neurological disorder in an animal, for use in compositions and methods to treat alopecia and promote hair growth in an animal, for use in compositions and methods to treat a vision disorder, improve vision, treat memory impairment, and enhance memory performance in an animal, and all the other uses suggested in this specification.

TABLE I

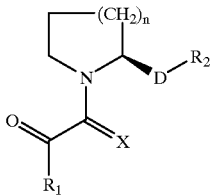

D is a bond and R₂ is COOH,

| No. | X | n | R₁ |
|---|---|---|---|
| 1 | O | 1 | 3,4,5-trimethylphenyl |
| 2 | O | 2 | 3,4,5-trimethylphenyl |
| 3 | O | 1 | tert-butyl |
| 4 | O | 3 | tert-butyl |
| 5 | O | 1 | cyclopentyl |
| 6 | O | 2 | cyclopentyl |
| 7 | O | 3 | cyclopentyl |
| 8 | O | 1 | cyclohexyl |
| 9 | O | 2 | cyclohexyl |
| 10 | O | 3 | cyclohexyl |
| 11 | O | 1 | cycloheptyl |
| 12 | O | 2 | cycloheptyl |
| 13 | O | 3 | cycloheptyl |
| 14 | O | 1 | 2-thienyl |
| 15 | O | 2 | 2-thienyl |
| 16 | O | 3 | 2-thienyl |
| 17 | O | 1 | 2-furyl |
| 18 | O | 2 | 2-furyl |
| 19 | O | 3 | 2-furyl |
| 20 | O | 3 | phenyl |
| 21 | O | 1 | 1,1-dimethylpentyl |
| 22 | O | 2 | 1,1-dimethylhexyl |
| 23 | O | 3 | ethyl |

TABLE II

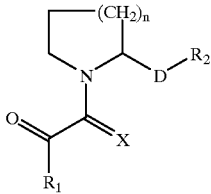

| No. | X | n | R₁ | D | R₂ |
|---|---|---|---|---|---|
| 24 | S | 1 | 1,1-dimethyl propyl | CH₂ | COOH |
| 25 | S | 1 | 1,1-dimethyl propyl | bond | COOH |
| 26 | O | 1 | 1,1-dimethyl propyl | CH₂ | OH |
| 27 | O | 1 | 1,1-dimethyl propyl | bond | SO₃H |
| 28 | O | 1 | 1,1-dimethyl propyl | CH₂ | CN |
| 29 | O | 1 | 1,1-dimethyl propyl | bond | CN |
| 30 | O | 1 | 1,1-dimethyl propyl | bond | tetrazolyl |
| 31 | S | 1 | phenyl | (CH₂)₂ | COOH |
| 32 | S | 1 | phenyl | (CH₂)₃ | COOH |
| 33 | S | 2 | phenyl | CH₂ | COOH |
| 34 | O | 1 | 1,1-dimethyl propyl | bond | CONH₂ |
| 35 | O | 2 | 1,1-dimethyl propyl | bond | CONH₂ |
| 36 | S | 2 | 2-furyl | bond | PO₃H₂ |
| 37 | O | 2 | propyl | (CH₂)₂ | COOH |
| 38 | O | 1 | propyl | (CH₂)₃ | COOH |
| 39 | O | 1 | tert-butyl | (CH₂)₄ | COOH |
| 40 | O | 1 | methyl | (CH₂)₅ | COOH |
| 41 | O | 2 | phenyl | (CH₂)₆ | COOH |
| 42 | O | 2 | 3,4,5-trimethoxyphenyl | CH₂ | COOH |
| 43 | O | 2 | 3,4,5-trimethoxyphenyl | CH₂ | tetrazolyl |

TABLE III

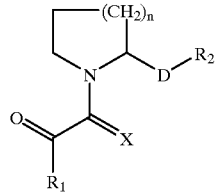

| No. | n | X | D | R₂ | R₁ |
|---|---|---|---|---|---|
| 44 | 1 | S | bond | COOH | Phenyl |
| 45 | 1 | O | bond | COOH | α-MethylBenzyl |
| 46 | 2 | O | bond | COOH | 4-MethylBenzyl |
| 47 | 1 | O | bond | Tetrazole | Benzyl |
| 48 | 1 | O | bond | SO₃H | α-MethylBenzyl |
| 49 | 1 | O | CH₂ | COOH | 4-MethylBenzyl |
| 50 | 1 | O | bond | SO₂HNMe | Benzyl |
| 51 | 1 | O | bond | CN | α-MethylBenzyl |
| 52 | 1 | O | bond | PO₃H₂ | 4-MethylBenzyl |
| 53 | 2 | O | bond | COOH | Benzyl |
| 54 | 2 | O | bond | COOH | α-MethylBenzyl |
| 55 | 2 | O | bond | COOH | 4-MethylBenzyl |
| 56 | 2 | S | bond | COOH | 3,4,5-trimethoxyphenyl |
| 57 | 2 | O | bond | COOH | Cyclohexyl |
| 58 | 2 | O | bond | PO₂HEt | i-propyl |
| 59 | 2 | O | bond | PO₃HPropyl | ethyl |
| 60 | 2 | O | bond | PO₃(Et)₂ | Methyl |
| 61 | 2 | O | bond | OMe | tert-butyl |
| 62 | 1 | O | bond | OEt | n-pentyl |
| 63 | 2 | O | bond | OPropyl | n-hexyl |
| 64 | 1 | O | bond | OButyl | Cyclohexyl |
| 65 | 1 | O | bond | OPentyl | cyclopentyl |
| 66 | 1 | O | bond | OHexyl | n-heptyl |
| 67 | 1 | O | bond | SMe | n-octyl |
| 68 | 1 | O | bond | SEt | n-nonyl |
| 69 | 2 | O | bond | SPropyl | 2-indolyl |
| 70 | 2 | O | bond | SButyl | 2-furyl |
| 71 | 2 | O | bond | NHCOMe | 2-thiazolyl |
| 72 | 2 | O | bond | NHCOEt | 2-thienyl |
| 73 | 1 | O | CH₂ | N(Me)₂ | 2-pyridyl |
| 74 | 1 | O | (CH₂)₂ | N(Me)Et | 1,1-dimethylpropyl |
| 75 | 1 | O | (CH₂)₃ | CON(Me)₂ | 1,1-dimethylpropyl |
| 76 | 1 | O | (CH₂)₄ | CONHMe | 1,1-dimethylpropyl |
| 77 | 1 | O | (CH₂)₅ | CONHEt | 1,1-dimethylpropyl |
| 78 | 1 | O | (CH₂)₆ | CONHPropyl | 1,1-dimethylpropyl |
| 79 | 1 | O | bond | CONH(O)Me | Benzyl |
| 80 | 1 | O | bond | CONH(O)Et | α-Methylphenyl |
| 81 | 1 | O | bond | CONH(O)Propyl | 4-Methylphenyl |
| 82 | 1 | O | (CH₂)₂ | COOH | Benzyl |
| 83 | 1 | O | bond | COOH | α-Methylphenyl |
| 84 | 1 | O | bond | COOH | 4-Methylphenyl |
| 85 | 1 | O | CH₂ | COOH | 1,1-dimethylpropyl |
| 86 | 1 | O | (CH₂)₂ | COOH | 1,1-dimethylbutyl |
| 87 | 1 | O | (CH₂)₃ | COOH | 1,1-dimethylpentyl |
| 88 | 1 | O | (CH₂)₄ | COOH | 1,1-dimethylhexyl |
| 89 | 1 | O | (CH₂)₅ | COOH | 1,1-dimethylethyl |
| 90 | 1 | O | (CH₂)₆ | COOH | iso-propyl |
| 91 | 1 | O | (CH₂)₇ | COOH | tert-butyl |
| 92 | 1 | O | (CH₂)₈ | COOH | 1,1-dimethylpropyl |
| 93 | 1 | O | (CH₂)₉ | COOH | benzyl |
| 94 | 1 | O | (CH₂)₁₀ | COOH | 1,1-dimethylpropyl |
| 95 | 1 | O | C₂H₂ | COOH | cyclohexylmethyl |
| 96 | 1 | O | 2-OH,Et | COOH | 1,1-dimethylpropyl |
| 97 | 1 | O | 2-butylene | COOH | 1,1-dimethylpropyl |
| 98 | 1 | S | i-Pro | COOH | 1,1-dimethylpropyl |
| 99 | 2 | S | tert-Bu | COOH | phenyl |
| 100 | 2 | O | 2-nitro-hexyl | COOH | 1,1-dimethylpropyl |
| 101 | 1 | O | (CH₂)₂ | CN | 1,1-dimethylpropyl |
| 102 | 1 | O | (CH₂)₃ | CN | 1,1-dimethylpropyl |
| 103 | 3 | O | bond | CONHNHSO₂Me | Benzyl |
| 104 | 3 | O | bond | CONHSO₂Et | α-Methylphenyl |
| 105 | 3 | O | bond | CONHSO₂Me | 4-Methylphenyl |
| 106 | 1 | O | bond | CONHNHSO₂Et | Phenyl |

TABLE III-continued

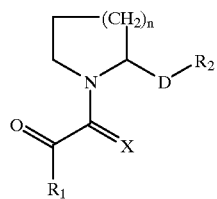

| No. | n | X | D | R₂ | R₁ |
|---|---|---|---|---|---|
| 107 | 2 | O | bond | CON(Me)CN | α-Methylphenyl |
| 108 | 1 | O | bond | CON(Et)CN | 4-Methylphenyl |
| 109 | 1 | O | (CH₂)₂ | COOH | methyl |
| 110 | 1 | O | (CH₂)₃ | COOH | ethyl |
| 111 | 1 | O | (CH₂)₄ | COOH | n-propyl |
| 112 | 1 | O | (CH₂)₅ | COOH | t-butyl |
| 113 | 1 | O | (CH₂)₆ | COOH | Pentyl |
| 114 | 1 | O | (CH₂)₇ | COOH | Hexyl |
| 115 | 1 | O | (CH₂)₈ | COOH | Septyl |
| 116 | 1 | O | (CH₂)₉ | COOH | Octyl |
| 117 | 1 | O | C₂H₂ | COOH | Cyclohexyl |
| 118 | 2 | O | bond | (tetrazole) | 1,1-dimethylpropyl |
| 119 | 1 | O | bond | (triazole-COOH) | 1,1-dimethylpropyl |
| 120 | 1 | O | bond | (N,N-dimethyl triazole) | 1,1-dimethylpropyl |
| 121 | 1 | O | bond | (thiazolidinedione) | 1,1-dimethylpropyl |
| 122 | 1 | O | bond | (hydroxy triazole) | 1,1-dimethylpropyl |
| 123 | 1 | O | bond | (mercapto tetrazole) | 1,1-dimethylpropyl |
| 124 | 1 | O | bond | (hydantoin) | 1,1-dimethylpropyl |

TABLE III-continued

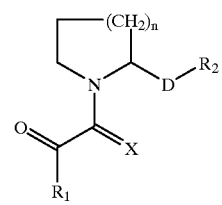

| No. | n | X | D | R₂ | R₁ |
|---|---|---|---|---|---|
| 125 | 1 | O | bond | (hydroxy isoxazole) | 1,1-dimethylpropyl |
| 126 | 1 | O | bond | (hydroxy maleimide) | 1,1-dimethylpropyl |
| 127 | 1 | O | bond | (hydroxy isoxazole) | 1,1-dimethylpropyl |
| 128 | 1 | O | bond | (mercapto triazole) | 1,1-dimethylpropyl |
| 129 | 1 | O | bond | (fluoro triazole) | 1,1-dimethylpropyl |
| 130 | 1 | O | bond | (ethyl oxadiazole) | 1,1-dimethylpropyl |
| 131 | 1 | O | bond | (oxadiazolidinedione) | 1,1-dimethylpropyl |
| 132 | 1 | O | bond | (succinimide) | 1,1-dimethylpropyl |

TABLE III-continued
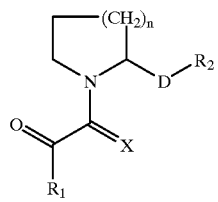
| No. | n | X | D | R₂ | R₁ |
|---|---|---|---|---|---|
| 133 | 1 | O | bond | 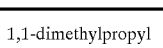 | 1,1-dimethylpropyl |
| 134 | 1 | O | bond | 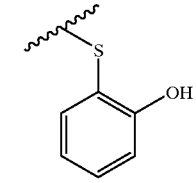 | 1,1-dimethylpropyl |
| 135 | 1 | O | bond | 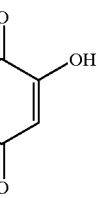 | 1,1-dimethylpropyl |
| 136 | 1 | O | bond | 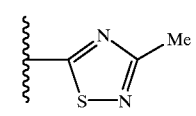 | 1,1-dimethylpropyl |
| 137 | 1 | O | bond | COOH | 1,1-dimethylpropyl |
| 138 | 2 | O | bond | COOH | 1,1-dimethylpropyl |
Specific embodiments of the present invention may be found in TABLE IV below:
TABLE IV
| Compound No. | Compound Structure |
|---|---|
| 28 | 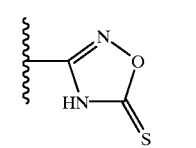 |
| 139 | 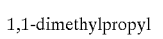 |
| 140 | 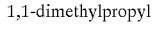 |
| 141 | 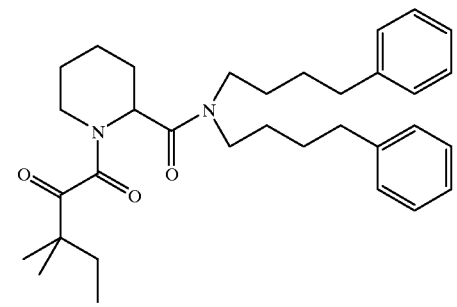 |
| 142 | 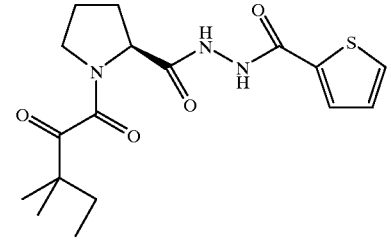 |
| 143 | 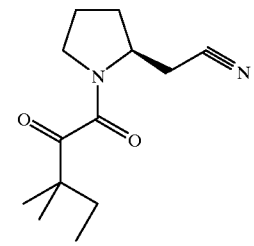 |

TABLE IV-continued

| Compound No. | Compound Structure |
|---|---|
| 144 | 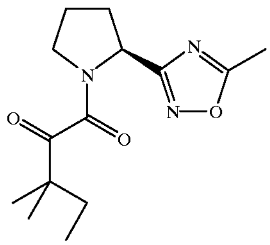 |
| 145 | 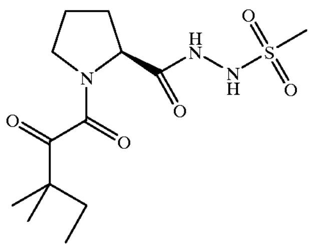 |
| 146 | 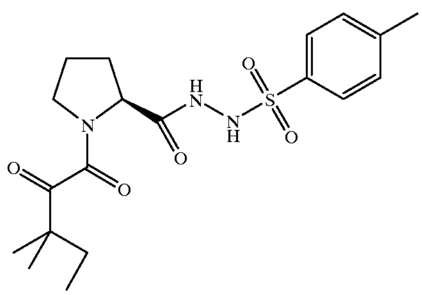 |
| 147 | 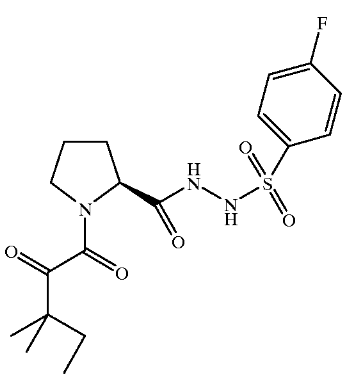 |
| 148 | 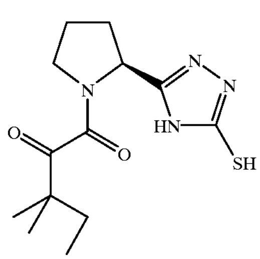 |
| 149 | |
| 150 | |
| 151 | |
| 152 | |
| 153 | |

TABLE IV-continued

| Compound No. | Compound Structure |
|---|---|
| 154 | (structure) |
| 155 | (structure) |

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

Other compounds which are carboxylic acids and isosteres of N-heterocyclic compounds within the scope of the present invention are those compounds which may possess immunosuppressive, non-immunosuppressive, or other activities as long as they also are useful in preventing and/or treating neurological disorders, including physically damaged nerves and neurodegenerative diseases; in treating alopecia and promoting hair growth; in treating vision disorders and/or improving vision; and in treating memory impairment and/or enhancing memory performance.

MPTP Model of Parkinson's Disease in Mice

YPTP lesioning of dopaminorgic neurons in mice was used as an animal model of Parkinson's Disease. Four week old male CD1 white mice were dosed i.p. with 30 mg/kg of MPTP for 5 days. The inventive compounds (4 mg/kg), or vehicle, were administered s.c. along with the MPTP for 5 days, as well as for an additional 5 days following cessation of YiPTP treatment. At 18 days following MPTP treatment, the animals were sacrificed and the striata were dissected and homogenized. Immunostaining was performed on sagital and coronal brain sections using anti-tyrosine hydroxylase Ig to quantitate survival and recovery of dopaminergic neurons. In animals treated with MPTP and vehicle, a substantial loss of functional dopaminergic terminals was observed as compared to non-lesioned animals. In another protocol, test compounds were administered only subsequent to MPTP-induced lesioning. Thus, after animals were treated with MPTP for 5 days, an additional 3 days passed before beginning oral drug treatment on day 8. Animals were treated with the inventive compounds (0.4 mg/kg), administered orally, once a day for 5 days total. On day 18, the animals were sacrificed and analyzed as described above.

Table V presents the percent recovery of dopaminergic neurons in the first (concurrent dosing) paradigm in animals receiving carboxylic acid or carboxylic acid isostere compounds of the present invention.

Table V, below, shows the remarkable neuroregenerative effects of the inventive carboxylic acid or carboxylic acid isostere related compounds illustrating the neurotrophic capability of carboxylic acid isosteres as a class showing that lesioned animals receiving the carboxylic acid or carboxylic acid isostere compounds provide a remarkable recovery of TH-stained dopaminergic neurons.

Additional claimed or comparative carboxylic acids and isosteres of N-heterocyclic compounds which also show the remarkable neurotrophic and hair growth effects of the present invention are shown below in Table V:

TABLE V

MPTP Neurodegenerative Model

| COMPOUND | Post-MPTP % TH RECOVERY 10 mg/kg p.o. |
|---|---|
| Compound 26 | 23.2 |
| Compound 28 | 15.7 |
| Compound 29 | 34.1 |
| Compound 30 | 19.6 |
| Compound 35 | 46.5 |
| Compound 137 | 26.7 |
| Compound 140 | 10.4 |
| Compound 141 | 26.3 |
| Compound 143 | 29.2 |
| Compound 144 | 41.7 |
| Compound 146 | 40.6 |
| Compound 147 | n/a |
| Compound 148 | 21.4 |

Percent striatal innervation density was quantitated in brain sections with an anti-tyrosine hydroxylase immunoglobulin, which is indicative of functional dopaminergic neurons. The striatal innervation density of 23% for animals pretreated with only a vehicle and administered a vehicle orally during treatment, is indicative of normal non-lesioned striatal tissue. Striatal innervation density is reduced to 5% for animals pretreated with MPTP and administered a vehicle orally during treatment, and is indicative of MPTP-induced lesioning. Surprisingly, striatal innervation density is increased 8–13% for animals pretreated with MPTP and administered 0.4 mg/kg of an inventive compound orally during treatment, indicating substantial neuronal regeneration after induction of MPTP-derived lesions.

In Vivo Hair Generation Test with C57 Black 6 Mice

Figure 2:
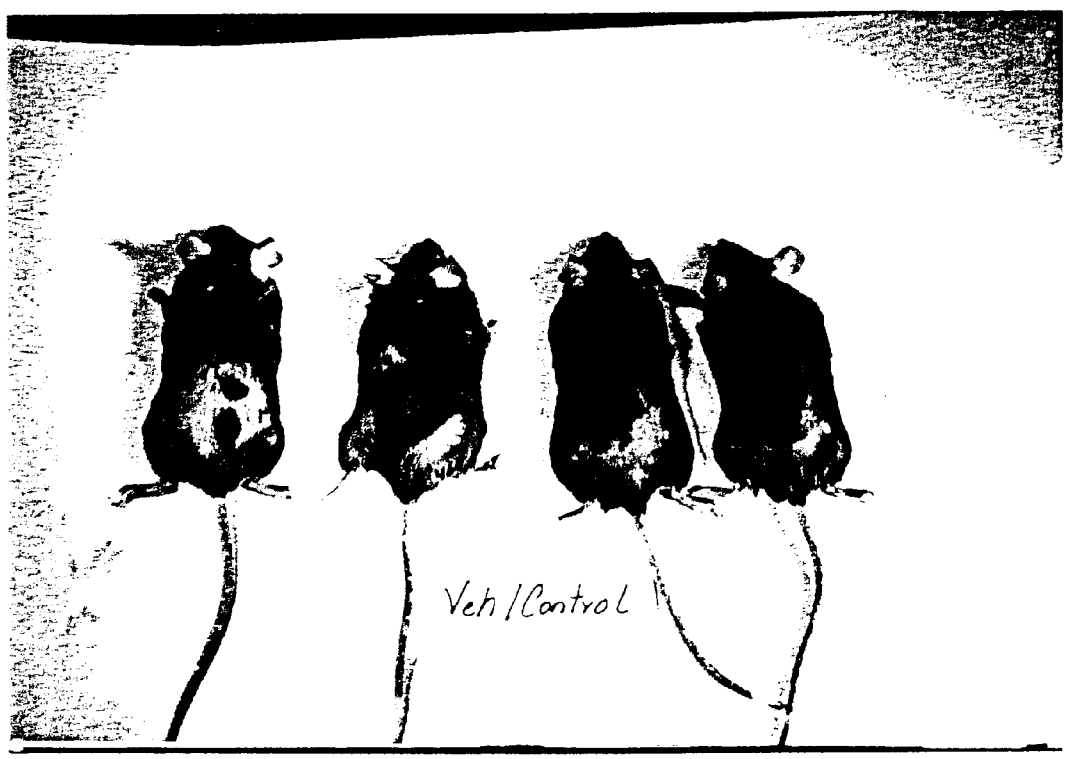
FIG. 2 is a photograph of mice treated with a vehicle after six weeks.

C57 black 6 mice were used to demonstrate the hair revitalizing properties of the N-heterocyclic carboxylic acids or carboxylic acid isosteres. Referring now to FIGS. 1 and 2 of the drawings, C57 black 6 mice, approximately 7 weeks old, had an area of about 2 inches by 2 inches on their hindquarters shaved to remove all existing hair. Care was taken not to nick or cause abrasion to the underlaying dermal layers. The animals were in anagen growth phase, as indicated by the pinkish color of the skin. Referring now to FIG. 2, four animals per group were treated by topical administration with 20% propylene glycol vehicle (FIG. 2), or neuroimmunophilin FKBP ligands dissolved in the vehicle. The animals were treated with vehicle or neuroimmunophilin ligands every 48 hours (3 applications total over the course of 5 days) and the hair growth was allowed to proceed for 6 weeks. Hair growth was quantitated by the percent of shaved area covered by new hair growth during this time period.

FIG. 2 shows that animals treated with vehicle exhibited only a small amount of hair growth in patches or tufts, with less than 3% of the shaved area covered with new growth.

Figure 3:
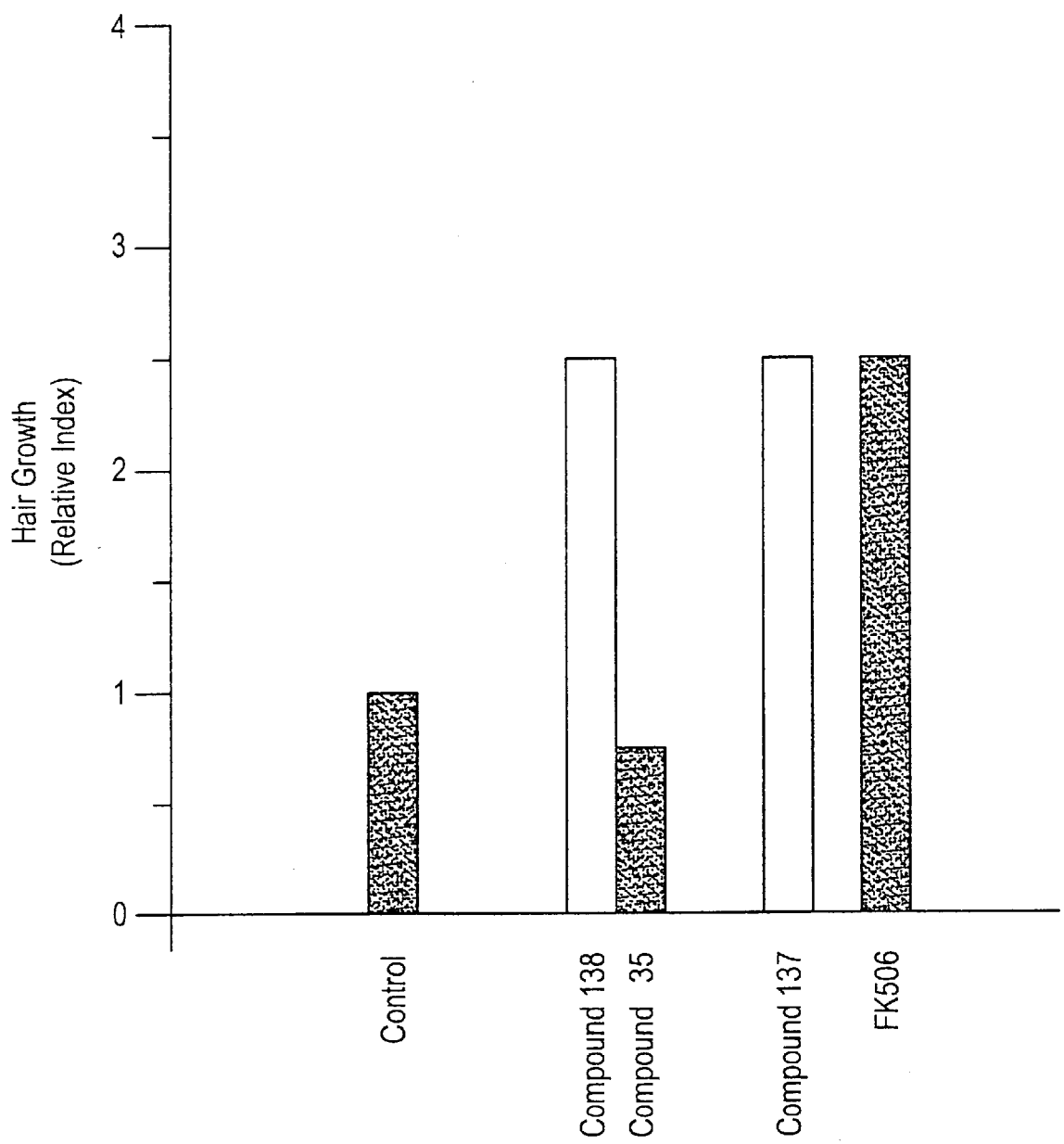
FIG. 3 is a bar graph illustrating relative hair growth on shaved mice treated with N-heterocyclic carboxylic acids or carboxylic acid isosteres at 1umole per milliliter three times per week. Hair growth was evaluated after 14 days of treatment.

In contrast, FIG. 3 shows that animals treated for 2 weeks with the N-heterocyclic carboxylic acid compounds i.e. compound A (137), compound B (138), and compound G (35) exhibited dramatic hair growth, covering greater than 25% of the shaved area in all animals for two of the compounds.

FIG. 3 shows the relative hair growth on shaven C57 black 6 mice 14 days after being treated with one of three N-heterocyclic carboxylic acids or carboxylic acid isosteres. The mice had a 2×2 inch region on their backside shaved to remove all hair. Care was taken not to nick or cause abrasion to the underlying dermal layers. Compounds at a concentration of 1 µmole per milliliter were carefully applied to the shaved area of the mice (5 mice per group) three times per week. Hair growth was evaluated 14 days after initiation of drug treatment. The relative scale for assessing hair growth is as follows:

0=no growth;
1=beginning of growth in small tufts;
2=hair growth covering over <25% of shaved area;
3=hair growth covering over >25% of shaved area, but less than 50% of shaved area;
4=hair growth covering over >50% of shaved area, but less than 75% of shaved area;
5=complete hair growth of shaved area.

Retinal Ganglion Cell Survival and Arrest of Axonal Dying Back Following Optic Nerve Transection Transection of the mammalian optic nerve results in a brief period of abortive regeneration, but the majority of axotomized neurons die and the axons from many persisting ganglion cells die back beyond the optic nerve head. The present Example was designed to examine the neuroprotective effects of GPI-1046 following optic nerve transection.

Retinal ganglion cells in adult male Sprague Dawley rats were retrogradely labeled by fluorogold injection in the LGNd and four days later the optic nerves were transected 5 mm behind the globe. Groups of animals received either GPI-1046 10 mg/kg/day s.c. or vehicle for 28 days. All experimental animals and controls were sacrificed 90 days after transection.

By 90 days only—10% of the FG labeled ganglion cell population survived but less than half of these neurons maintained axons that extended past the optic nerve head, as detected with RT97 neurofilament immunohistochemisty. GPI-1046 treatment produced a moderate degree of perikaryal neuroprotection, sparing 25% of the ganglion cell population, and preserved the axons of virtually all protected neurons in the proximal stump of the transected nerve. These results indicate that treatment with the FKBP neuroimmunophilin ligand GPI-1046 produces a fundamental alteration in the pathological process following injury to CNS tracts.

These results also demonstrate that the small molecule FKBP neuroimmunophilin ligand GPI 1046 enhances neurite outgrowth in culture, enhance peripheral nerve regeneration, and stimulate sprouting within the CNS following partial deafferentation.

In Vivo Retinal Ganglion Cell and Optic Nerve Axon Tests

The extent of degeneration reduction or prevention in retinal ganglion cells and optic nerve axons was determined in a vision loss model utilizing surgical optic nerve transection to simulate mechanical damage to the optic nerve. The effects of several N-heterocyclic derivative neuroimmunophilin FKBP ligands on retinal ganglion cells neuroprotection and optic nerve axon density was determined experimentally, comparing 14 day and 28 day N-heterocyclic derivative neuroimmunophilin FKBP ligand treatments. The effects of treatment with N-heterocyclic derivative neuroimmunophilin FKBP ligands on retinal ganglion cells and optic nerve axons was correlated.

Surgical Procedures

Adult male Sprague Dawley rats (3 months old, 225–250 grams) were anesthetized with a ketamine (87 mg/kg) and xylazine (13 mg/kg) mixture. Retinal ganglion cells were pre-labeled by bilateral stereotaxic injection of the fluorescent retrogradely transported marker fluoro-gold (FG, 0.5 microliters of 2.5% solution in saline) at the coordinates of the LGNd (4.5 millimeters post β, 3.5 millimeters lateral, 4.6 millimeters below dura). Four days later, FC labeled rats underwent a second surgery for microsurgical bilateral intraorbital optic nerve transection 4–5 millimeters behind the orbit.

Experimental animals were divided into six experimental groups of six rats (12 eyes) per group. One group received an N-heterocyclic derivative neuroimmunophilin FKBP ligand (10 milligrams per kg per day so in PEG vehicle (20 percent propylene glycol, 20 percent ethanol, and 60 percent saline)) for 14 days. A second group received the same N-heterocyclic derivative neuroimmunophilin FKBP ligand dose for 28 days. Each treated group had a corresponding sham/surgery and transection control group which received corresponding 14 or 28 day dosing with the vehicle only.

All animals were sacrificed 90 days after optic nerve transection and perfused pericardially with formalin. All eyes and optic nerves stumps were removed. Cases were excluded from the study if the optic nerve vasculature was damaged or if FG labeling was absent in the retina.

Retinal Ganglion Cell Counts

Retinas were removed from eyes and prepared for whole-mount analysis. For each group, five eyes with dense and intense FG labeling were selected for quantitative analysis using a 20 power objective. Digital images were obtained from five fields in the central retina (3–4 millimeters radial to optic nerve head). FG labeled Large (>18 µm), medium (12–16 µm), and small (<10 µm) ganglion cells and microglia were counted in five 400 µm by 400 µm fields per case, 5 cases per group.

Examination of Optic Nerves

Proximal and distal optic nerve stumps were identified, measured, and transferred to 30% sucrose saline. The proximal stumps of five nerves were blocked and affixed to a chuck, and 10 micron cross sections were cut on a cryostat; one in ten sections were saved per set. Sections including the region 1–2 mm behind the orbit were reacted for RT97 neurofilament immunohistochemistry. Analysis of optic nerve axon density was performed using a 63 power oil immersion lens, a Dage 81 camera, and the Simple Image Analysis program. RT97 positive optic nerve axons were counted in three 200 µm by 200 µm fields per nerve. The area of the nerve was also determined for each case at 10 power.

The 14 day course of treatment with an N-heterocyclic derivative neuroimmunophilin FKBP ligand provided moderate neuroprotection of retinal ganglion cells observed 28 days after optic nerve transection. However, by 90 days after transection, only 5% of the ganglion cell population remained viable. 90 days after optic nerve transection the number of axons persisting in the proximal stump of the optic nerve represented approximately one half of the number of surviving ganglion cells in groups of animals that received vehicle alone or the 14 day course of treatment with an N-heterocyclic derivative neuroimmunophilin FKBP ligand. These results indicate that over half of the transected ganglion cell axons retract beyond the optic nerve head, and that treatment with an N-heterocyclic derivative neuroimmunophilin FKBP ligand during the first 14 days after optic nerve transection is not sufficient to arrest this retraction.

More prolonged treatment with an N-heterocyclic derivative neuroimmunophilin FKBP ligand during the 28 day course of treatment produced a moderate increase in retinal ganglion cell neuroprotection. Approximately 12% of the vulnerable retinal ganglion cell population was protected. A similar proportion (~50%) of optic nerve axon density sparing was also observed. These results demonstate the startling result that extending the duration of treatment with an N-heterocyclic derivative neuroimmunophilin FKBP ligand to 28 days after transection completely arrests the regression of damaged axons for essentially the entire surviving population of retinal ganglion cells.

Figure 4A:
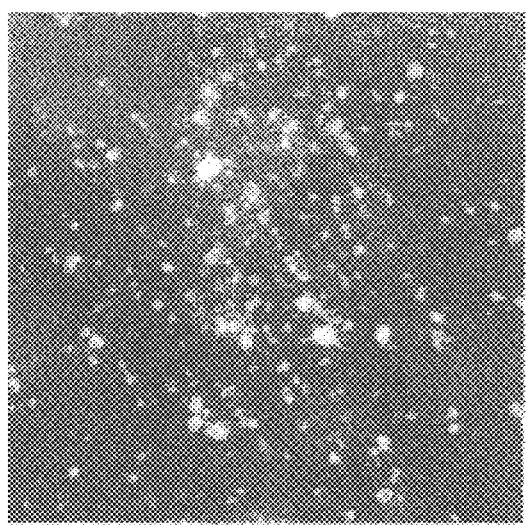
FIGS. 4A, B, and C show that GPI 1046 protects ganglion cells against degeneration following retinal ischemia.
Figure 4B:
Figure 4C:
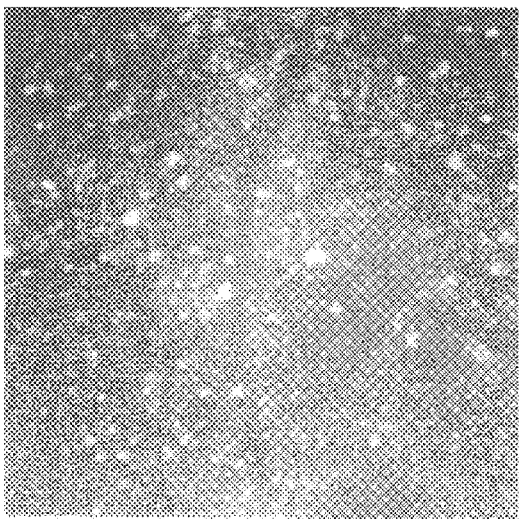

FIG. 4. GPI 1046 Protects Retinal Ganglion Cells Against Degeneration Following Retinal Ischemia Retinal ganglion cells were retrogradely labeled in adult rats by bilateral injection of fluorogold in their lateral geniculate nuclei. Labeled ganglion cells in the normal rat retina appear as white profiles against the dark background (FIG. 4A). Complete retinal ischemia was produced by infusing normal saline solution into the retinal vitreous cavity of each eye until the intraocular pressure exceeded arterial blood pressure. 28 days after the ischemic episode extensive degeneration of retinal ganglion cell was evidenced by massive reduction in the density of fluorogold labeled cells (FIG. 4B). Administration of GPI 1046 (10 mg/kg, s.c.) 1 hour prior to the ischemic episode and at 10 mg/kg/day for the next four days produced noticeable protection of a large proportion of the vulnerable ganglion cell population (FIG. 4C).

Figure 5A:
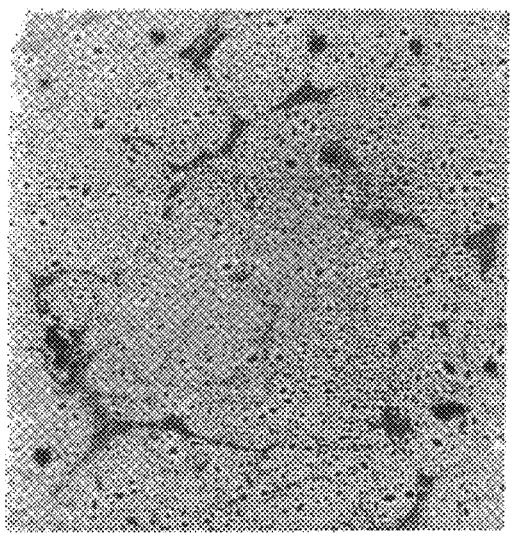
FIG. 5 shows that GPI 1046 prevents degeneration of optic nerve axons and myelin following retinal ischemia.
Figure 5B:
Figure 5C:
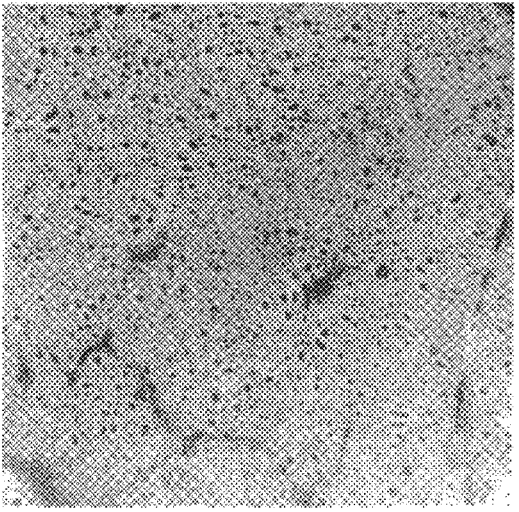

FIG. 5. GPI 1046 Prevents Degeneration of Optic Nerve Axons and Myelin Following Retinal Ischemia Examination of the optic nerves from the same retinal ischemia cases reveals that GPI 1046 produces dramatic protection of optic nerve element from ischemic degeneration. Toluidine blue staining of epon embedded optic nerve cross sections revealed the detail of myelin sheaths (white circles) and optic nerve axons (black centers) in the normal rat optic nerve. Optic nerves from vehicle treated cases examined 28 days after a 1 hour retinal ischemic episode are characterized by a decreased density of optic nerve axons and the appearance of numerous degenerating myelin figures (bright white filled circles). Treatment with GPI 1046 protected the majority of optic nerve axons from degeneration and also dramatically decreased the density of degenerating myelin figures.

Figure 6A:
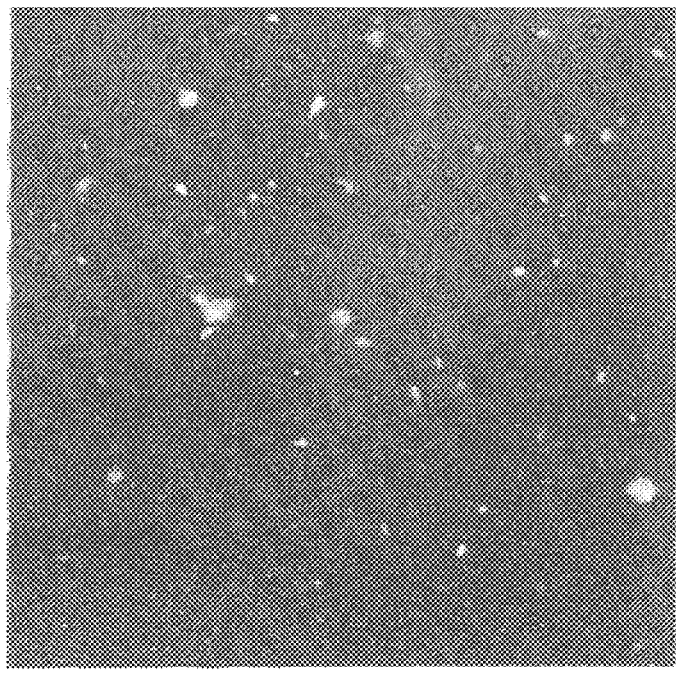
FIG. 6 shows that GPI 1046 provides moderate protection against retinal ganglion cell death after optic nerve transection.
Figure 6B:
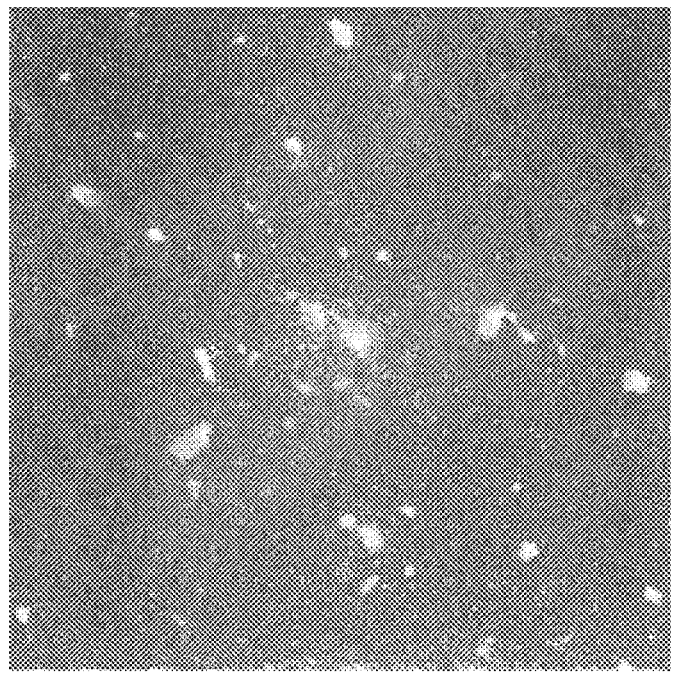
Figure 7A:
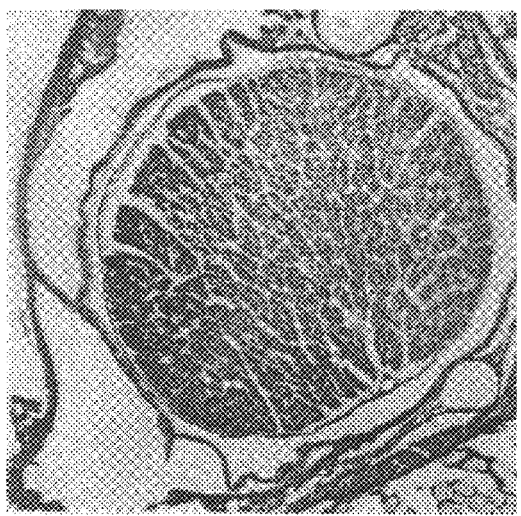
FIG. 7 shows that GPI 1046 treatment duration significantly affects the process of optic nerve axonal degeneration after transection.
Figure 7B:
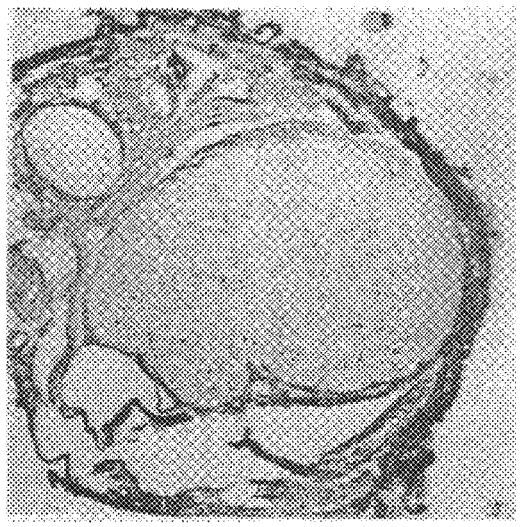
Figure 7C:
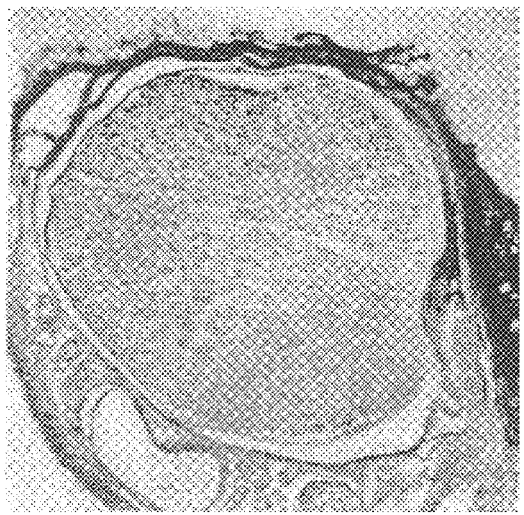
Figure 7D:
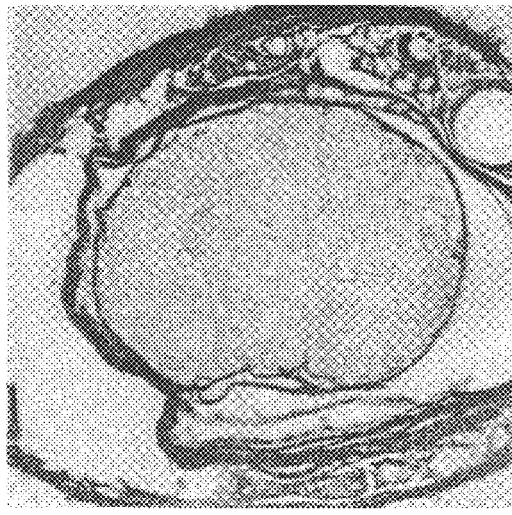
Figure 8A:
FIG. 8 shows that GPI 1046 treatment produces a greater effect on optic nerve axons than ganglion cell bodies.
Figure 8B:
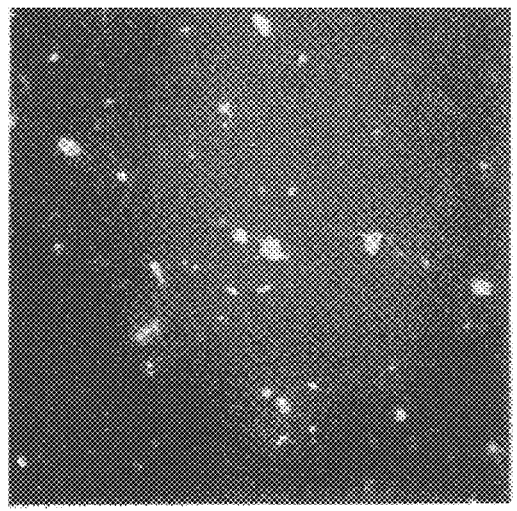
Figure 8C:
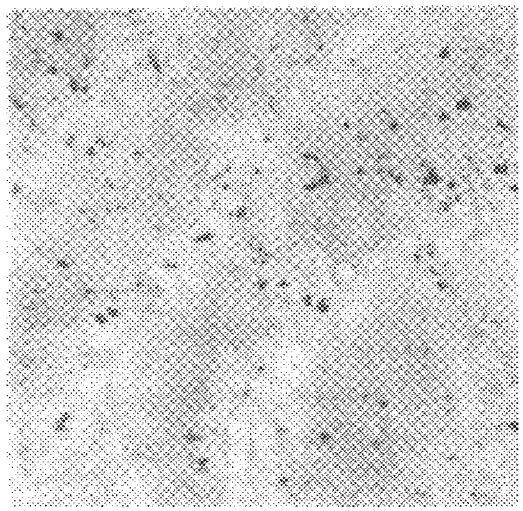
Figure 8D:
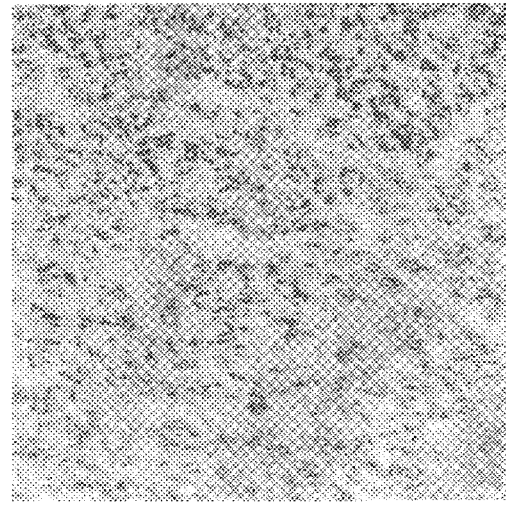
Figure 9A:
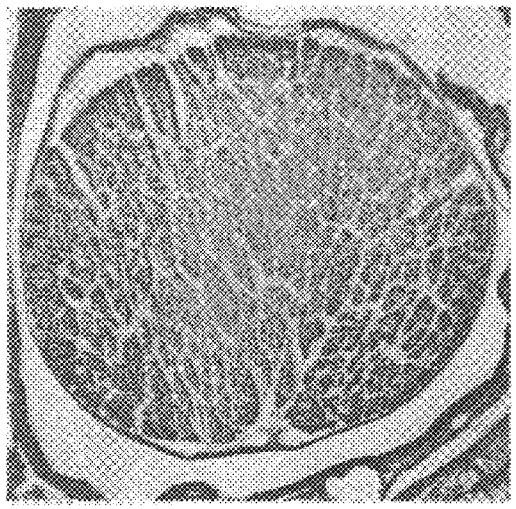
FIG. 9 shows that GPI 1046 treatment for 28 days after optic nerve transection prevents myelin degeneration in the proximal stump.
Figure 9B:
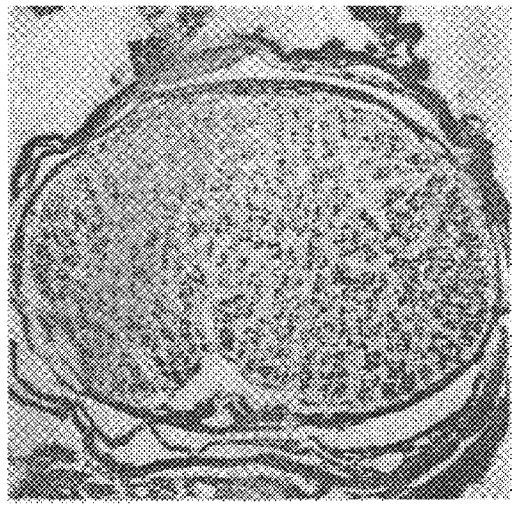
Figure 9C:
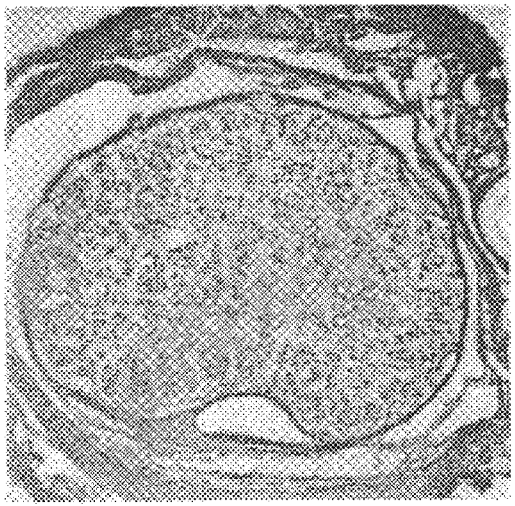
Figure 9D:
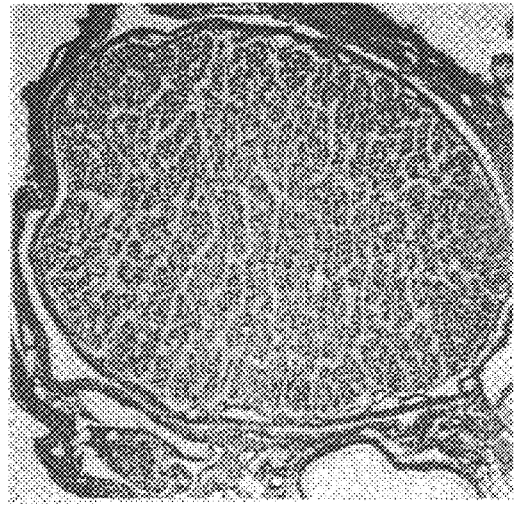

FIG. 6. GPI 1046 Provides Moderate Protection Against Retinal Ganglion Cell Death After Optic Nerve Transection Complete transection of the optic nerve 5 mm from the eyeball produces massive degeneration of retinal ganglion cells, representing loss of >87% of the normal ganglion cell population 90 days after the injury. Few spared fluorogold pre labeled ganglion cells are present in vehicle treated cases (large white figures) among a population of small microglia that digest the debris of the degenerating cells and take up the fluorogold label (FIG. 6A). Treatment with GPI 1046 for 14 days resulted in a small but not significant increase in the density of retinal ganglion cells that survived 90 days after transection but treatment with GPI 1046 for the first 28 days after transection produced moderate but significant protection of 12.6% of the vulnerable ganglion cell population (FIG. 6B).

FIG. 7. GPI 1046 Treatment Duration Significantly Affects the Process of Optic Nerve Axonal degeneration After Transection Examination of optic nerve axon density in the proximal stump of the optic nerve from the same cases revealed a more dramatic protection afforded by GPI 1046 treatment. 90 days after transection few ganglion cell axons remain within the optic nerve (FIG. 7B), representing only 5.6% of the normal population. The loss of axons reflects both the death of retinal ganglion cells and the regression or "dying back" of the axons of ~70% of the small surviving ganglion cell population into the retina itself (Table 1). Treatment with GPI 1046 for the first 14 days after optic nerve transection produced a small but significant 5.3% protection of optic nerve axons (FIG. 7D, Table 1), but treatment with the same dose of GPI 1046 for 28 days resulted in the protection of optic nerve axons for the vast majority (81.4%) of spared retinal ganglion cells (FIG. 7C, Table 1).

FIG. 8. GPI 1046 Treatment Produces a Greater Effect on Optic Nerve Axons than Ganglion Cell Bodies This summary figure shows data from FIG. 6 ganglion cell protection and higher power photomicrographs of optic nerve axon protection (FIGS. 8A&B, upper panels). 28 day treatment with GPI 1046 produced a significant increase in the density of large, and particularly medium and small caliber optic nerve axons (FIG. 8C&D, lower panels).

FIG. 9. GPI 1046 Treatment for 28 Days After Optic Nerve Transection Prevents Myelin Degeneration in the Proximal Stump Myelin basic protein immunohistochemistry labels fascicles (darker labeled 'islands') of myelinated axons in the normal optic nerve (FIG. 9A, upper left). 90 days after transection extensive degeneration of myelin is evident in vehicle treated cases, characterized by the loss of fascicular organization and the appearance of numerous large dense degenerating myelin figures (FIG. 9B, upper right). Treatment with GPI 1046 for the first 14 days after optic nerve transection did not alter the pattern of myelin degeneration (FIG. 9C, lower left panel), and yielded an insignificant 1.6% quantitative recovery in myelin density (Table 1). Extending the GPI 1046 treatment course through the first 28 days after optic nerve transaction produced a dramatic preservation of the fascicular staining pattern for myelin basic protein in the proximal stump of the optic nerve and decreased the density of degenerating myelin figures (FIG. 9D, lower right panel), representing a '70% recovery of myelin density (Table 1).

Figure 10:
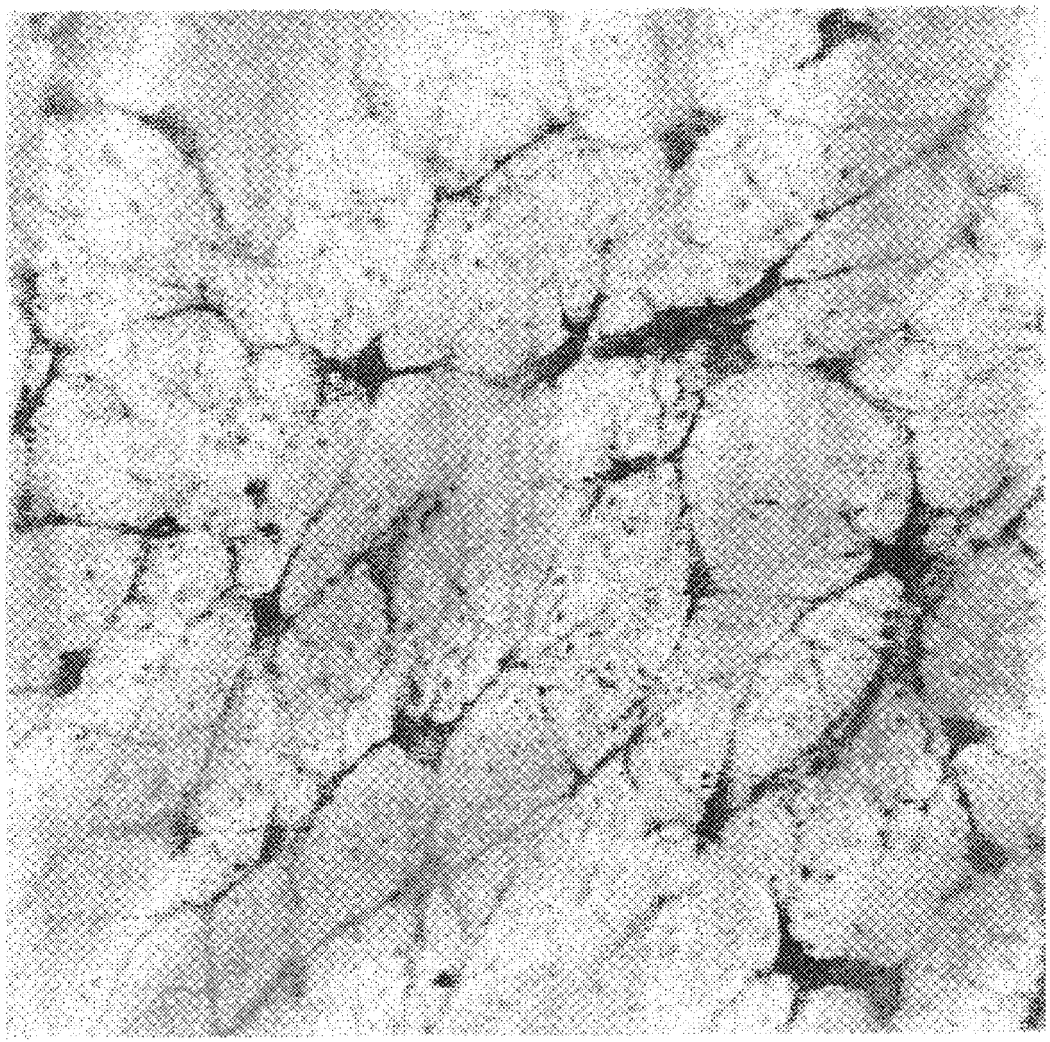
FIG. 10 shows that FKBP-12 immunohistochemistry labels oligodendroglia (large dark cells with fibrous processes), the cells which produce myelin, located between the fascicles of optic nerve fibers, and also some optic nerve axons.
Figure 11A:
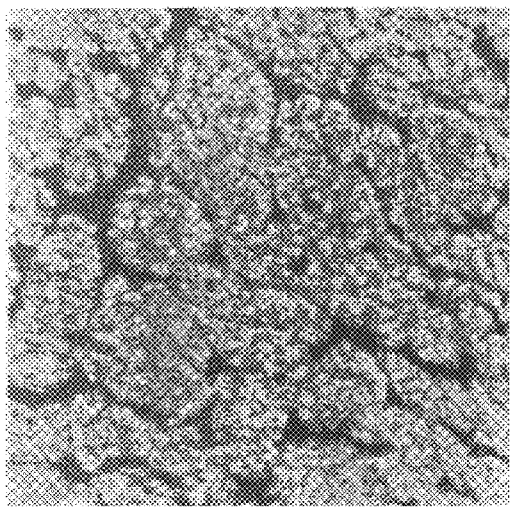
FIG. 11 shows GPI 1046 treatment for 28 days after optic nerve transection prevents myelin degeneration in the distal stump.
Figure 11B:
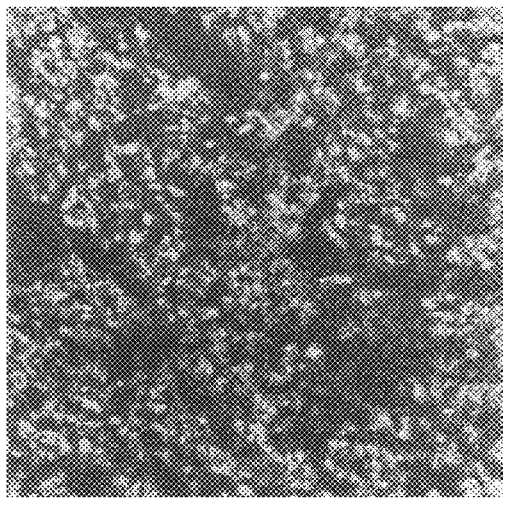
Figure 11C:
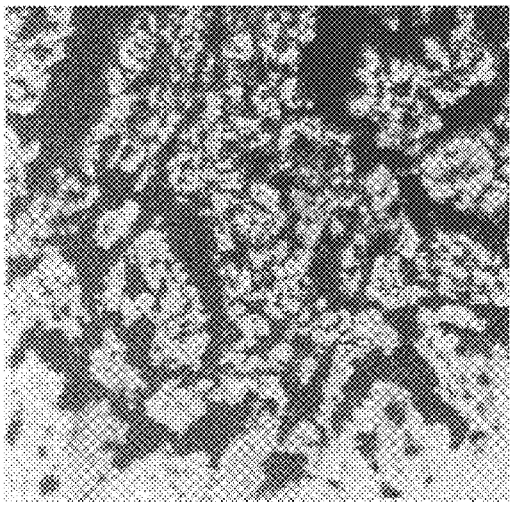
Figure 11D:
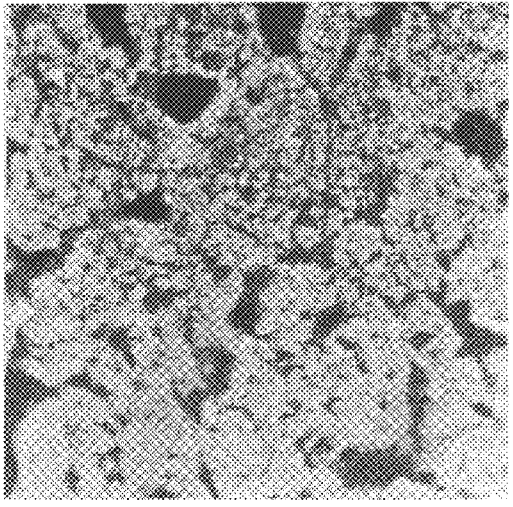

FIG. 10. FKBP-12 Immunohistochemistry Labels Oligodendroglia (Large Dark Cells with Fibrous Processes), the Cells which Produce Myelin, Located Between the Fascicles of Optic Nerve Fibers, and Also Some Optic Nerve Axons FIG. 11. GPI 1046 Treatment for 28 Days After Optic Nerve Transection Prevents Myelin Degeneration in the Distal Stump Complete transaction of the optic nerve leads to degeneration of the distal segments (axon fragments disconnected from the ganglion cell bodies), and the degeneration of their myelin sheaths. 90 days after transection (FIG. 11B) myelin basic protein immunohistochemistry reveals the near total loss of fascicular organization (present in the normal optic nerve, FIG. 11A) and the presence of numerous dense degenerating myelin figures. Quantitation reveals that the cross sectional area of the transected dismal stump shrinks by 31% and loses approximately ½ of its myelin (Table 1). Treatment with GPI 1046 for the first 14 days after transection did not protect against shrinkage of the distal stump but did slightly increase the density of myelin, though the density of degenerating myelin figures remained high (FIG. 11C, Table 1). GPI 1046 treatment through the first 28 days produced dramatic protection of the fascicular pattern of myelin labeling, decreased the density of degenerating myelin figures, prevented cross sectional shrinkage of the distal stump of the transected nerve and maintained the myelin levels at ~99% of normal levels (FIG 11D, Table 1).

Figure 12A:
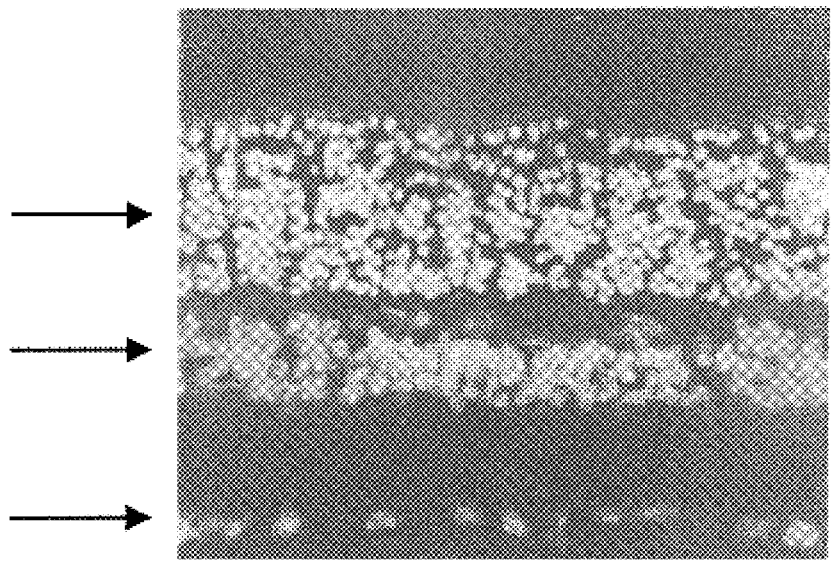
FIG. 12 shows that 28 day treatment with GPI 1046 treatment beginning 8 weeks after onset of streptozotocin induced diabetes decreases the extent of neovascularization in the inner and outer retina and protects neurons in the inner nuclear layer (INL) and ganglion cell layer (GCL) from degeneration.
Figure 12B:
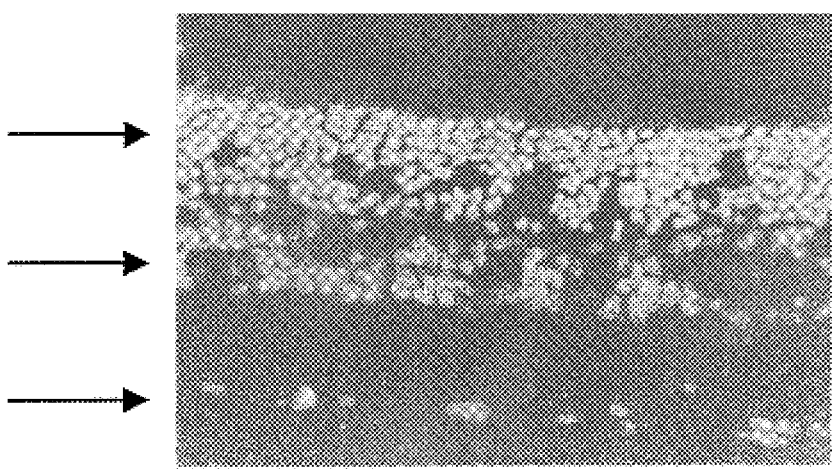
Figure 12C:

FIG. 12. 28 Day Treatment with GPI 1046 Treatment Beginning 8 Weeks After Onset of Streptozotocin Induced Diabetes Decreases the Extent of Neovascularization in the Inner and Outer Retina and Protects Neurons in the Inner Nuclear Layer (INL) and Ganglion Cell Layer (GCL) from Degeneration Negative images of cresyl violet stained tangential retinal sections reveals perikarya in the three cellular layers (FIG. 12A). The retinae of streptozotocin treated animals administered only vehicle (FIG. 12B) exhibited loss of cells from the ONL and INL, decreased thickness of the Outer plexiform layer (the dark area between ONL and INL) and a dramatic increase in the size and density of retinal blood vessels (large black circular outlines) in the INL, OPL, ONL and the photoreceptor layer (PR, the gray fuzzy area above the ONL). GPI 1046 treatment reduced neovascularization (i.e. prevented the proliferation of blood vessels) in the PR, ONL, OPL and INL. Although GPI 1046 did not appear to protect against neuronal loss in the ONL, it appeared to decrease the loss of neurons in both the INL and GCL compared to streptozotocin/vehicle treated controls.

Protection of Retinal Ganglion Cell Axons from Degeneration Following Optic Nerve Transection Efficacy of representative compounds from different immunophilin ligand series in protecting retinal ganglion cell axons from degeneration following optic nerve transection is set forth in Table VI.

TABLE VI

Efficacy of Representative Compounds from Different Immunophilin Ligand Series in Protecting Retinal Ganglion Cell Axons from Degeneration Following Optic Nerve Transection

| Compound | Structure | Comments | RT97 + RG C axon density 14 days after ON transection (% ON axons rescued) |
|---|---|---|---|
| B | 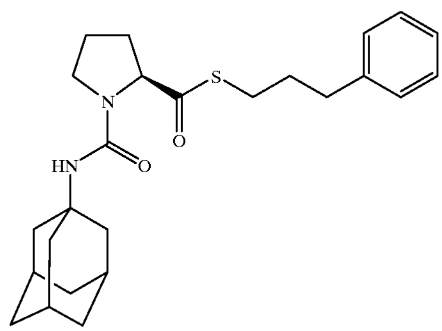 | Adamantyl Thioester of Urea $K_i$ Rotamase = 149 nM Clearance = ? μl/min. | 100% ±5.2% SEM |
| A (GPI 1046) | | Ester $K_i$ Rotamase = 7.5 nM Clearance = 63.8 μl/min. | 60.5% ±3.9% SEM |
| C | 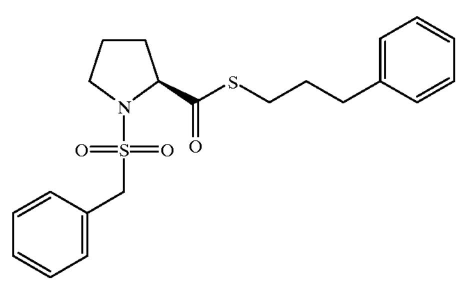 | Sulfonamide $K_i$ Rotamase = 107 nM Clearance = 31.1 μl/min. | 60.4% ±3.1% SEM |

TABLE VI-continued

Efficacy of Representative Compounds from Different Immunophilin Ligand Series in Protecting Retinal Ganglion Cell Axons from Degeneration Following Optic Nerve Transection

| Compound | Structure | Comments | RT97 + RG C axon density 14 days after ON transection (% ON axons rescued) |
|---|---|---|---|
| D | 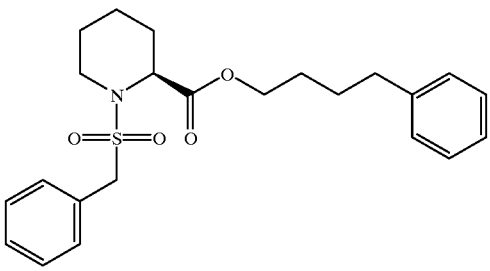 | Pipecolic Sulfonamide<br>$K_i$ Rotamase = ? nM<br>Clearance = ? μl/min. | 58.4%<br>±6.4%<br>SEM |
| E | 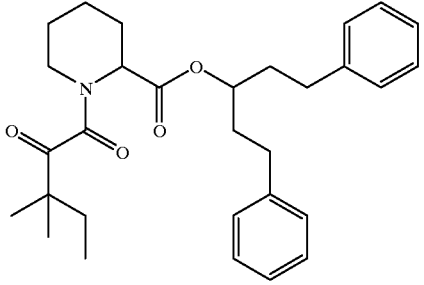 | Ester of Pipecolic Acid<br>$K_i$ Rotamase = 20 nM<br>Clearance = 41.8 μl/min. | 56.6%<br>±9.4%<br>SEM |
| F | 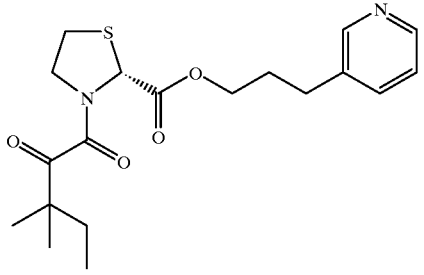 | Proline heterocycle<br>$K_i$ Rotamase = 272 nM<br>Clearance =? μl/min. | 55.1%<br>±5.9%<br>SEM |
| G | 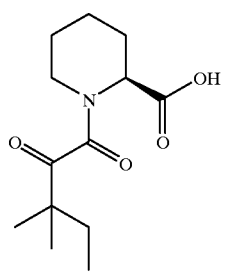 | Pipecolic acid dimethyl ketone<br>$K_i$ Rotamase > 10,000 nM<br>Clearance = ? μl/min. | 34.0%<br>±4.8%<br>SEM |

TABLE VI-continued

Efficacy of Representative Compounds from Different Immunophilin Ligand Series in Protecting Retinal Ganglion Cell Axons from Degeneration Following Optic Nerve Transection

| Compound | Structure | Comments | RT97 + RG C axon density 14 days after ON transection (% ON axons rescued) |
|---|---|---|---|
| H | 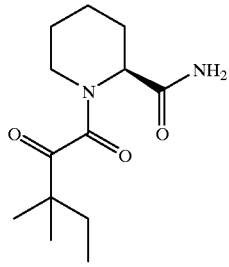 | Pipecolic acid dimethyl amide $K_i$ Rotamase = ? nM Clearance = ? μl/min. | 30.3% ±8.0% SEM |
| I | 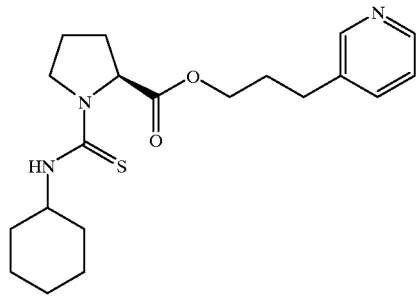 | Ester of thiourea $K_i$ Rotamase = 131 nM Clearance = 8.0 μl/min. | 23.8% ±5.3% SEM |
| J | 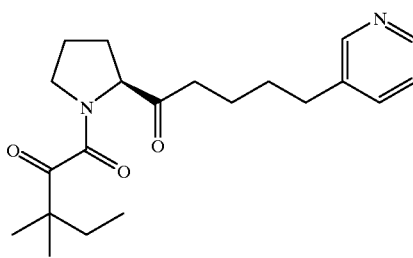 | Ketone analog of GPI 1046 $K_i$ Rotamase = 210 nM Clearance = 1.5 μl/min. | 15.8% ±4.8% SEM |
| K | 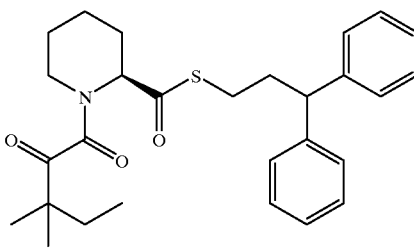 | Pipecolic acid thioester $K_i$ Rotamase = 86 nM Clearance = 4.5 μl/min. | 13.0% ±4.2% SEM |
| L | 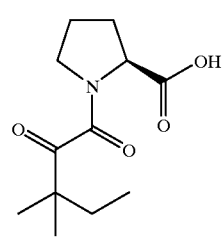 | Prolyl acid $K_i$ Rotamase >7743 nM Clearance = 5.2 μl/min. | 7.8% ±3.0% SEM |

TABLE VI-continued

Efficacy of Representative Compounds from Different Immunophilin Ligand Series in Protecting Retinal Ganglion Cell Axons from Degeneration Following Optic Nerve Transection

| Compound | Structure | Comments | RT97 + RG C axon density 14 days after ON transection (% ON axons rescued) |
|---|---|---|---|
| M | 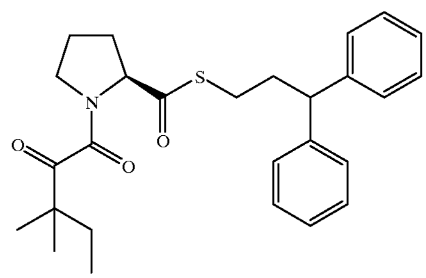 | Thioester<br>$K_i$ Rotamase = 7 nM<br>Clearance = 12.5 μl/min. | −6.3%<br>±3.9%<br>SEM |
| N | 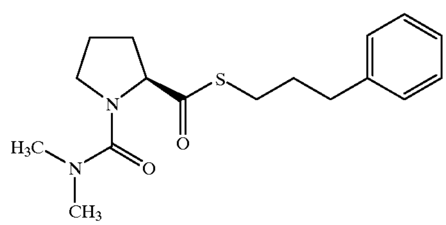 | $K_i$ Rotamase = 722 nM<br>Clearance = 21.9 μl/min. | ND |

Morris Watermaze/Aging and Memory Testing

Aged rodents exhibit marked individual differences in performance on a variety of behavioral tasks, including two-choice spatial discrimination in a modified T-maze, spatial discrimination in a circular platform task, passive avoidance, radial maze tasks, and spatial navigation in a water pool.

In all of these tasks, a proportion of aged rats or mice perform as well as the vast majority of young control animals, while other animals display severe impairments in memory function compared to young animals. For example, Fischer and colleagues showed that the proportion of rats displaying significant impairments in spatial navigation increases with age, (Fischer et al. 1991b) with 8% of all 12 month old, 45% of 18 month old, 53% of 24 month old, and 90% of all 30 month old rats displaying impairments in spatial acquisition of the Morris watermaze task relative to young controls.

Specifically, rodent spatial learning and memory decline during aging has been accepted by many investigators as an intriguing correlative animal model of human senile dementia. Cholinergic function in the hippocampus has been extensively studied as a component of spatial learning in rodents, and declining hippocampal cholinergic function has been noted in parallel with the development of learning and memory impairments. In addition, other neurotransmitter systems have been shown to contribute to spatial learning, and to decline with age, such as the dopaminergic and noradrenergic, serotonergic, and glutamatergic systems.

Also, reports on age-related deficits of hippocampal long-term potentiation (LTP)-induction, a reduction in theta rhythm frequency, a loss of experience-dependent plasticity of hippocampal place-units, and reductions in hippocampal protein kinase C are in keeping with the concept that no single underlying pathology can be identified as the cause of age-related behavioral impairment in rodents. However, the various experimental therapeutic approaches that have been undertaken to improve memory function in aged rodents have been somewhat slanted towards the cholinergic hypothesis.

The Morris watermaze is widely used for assessing spatial memory formation and retention in experimental animals. The test depends on the animal's ability to utilize spatial visual information in order to locate a submerged escape platform in a water tank. It is important that the tank itself be as devoid of specific visual features as possible—thus, it is always circular in shape, the sides are kept smooth and in uniform dull colors, and the water is rendered opaque with nontoxic watercolour pigment or powdered milk. This is to ensure that the animal navigates only by the use of more distant visual cues, or by the use of intra-maze cues specifically provided by the experimenter.

The tank is filled to a level which forces the animal to swim actively. Normal mice and rats react aversively to the swimming part of the test and will climb onto, and remain on, an escape platform from which they are removed to a heated resting cage.

If the platform is visible (i.e. above the surface), animals placed in the tank will quickly learn to home in on the platform and climb out onto it. Testing with a visible platform will also ensure that the experimental animals are not blind and show sufficient motivation and stamina to perform the task, which can be important in experiments involving aged rodents. If the platform is invisible (i.e. submerged just below the surface), normal animals learn to use distant visual cues in the test room for orientation in the test tank, and, when placed in the tank, will quickly home in on the approximate location of the platform and circle in that area until the platform is found.

The animals' path, speed, and swim time are tracked with a ceiling camera for later computerized analysis. Over the course of several successive trials, spatial learning can therefore be defined as a drop of distance swum, or time elapsed, from placement in the tank until escape onto the invisible platform.

The test can be adapted to assess several aspects of spatial memory: a) acquisition of a cued task, where the animal's ability to link one visual cue directly with the escape platform depends on cortical function (i.e. a ball is suspended over the escape platform and the animal learns to follow this cue to find the platform); b) acquisition of a spatial task, where the animal's ability to learn the location of a submerged escape platform based on a combination of distant visual cues is dependent upon hippocampal function (i.e. the animal learns to triangulate its position in the tank by visually aligning the paper-tower dispenser with the door and ceiling lamp); c) retention of a successfully acquired spatial task, which is predominantly dependent on cortical function (i.e. the animal must remember the spatial location of the platform over several weeks); d) a hippocampus-dependant reversal task where the animals must reacquire a new spatial platform location (i.e. the platform is moved to a new location between swim trials and the animal must abandon its previous search strategy and acquire a new one).

These different modifications of the Morris watermaze procedure can be applied in sequence to the same set of experimental animals and allow for a thorough characterization of their spatial memory performance and its decline with normal ageing. Moreover, such a series of sequential memory tests sheds some light on the functional integrity of the specific brain systems involved in the acquisition and retention of spatial memory (e.g. rats with cholinergic lesions of the hippocampus may remember a platform location acquired weeks before, but persevere over the old platform location after the platform is moved).

Effects of Chronic GPI-1046 Administration on Spatial Learning and Memory in Aged Rodents This Example shows the effects of chronic treatment with the systemically available FKBP-ligand GPI-1046 on spatial learning and memory in aged rodents.

The procedure involved using three-month old (young) and 18–19 month old male C57BL/6N-Nia (aged) mice which habituated to the well known and conventional Morris watermaze during a 4 trials/day, 3–4 day visible platform training phase. Subsequent spatial acquisition testing was conducting as follows: All mice were given 4 trials/day (block), for 5 days. Maximum swim time was 90 seconds. Aged mice were allocated to an "aged impaired" group if their performance during blocks 4 or 5 of the acquisition phase was >1 S.D. above the mean of "young" mice, and to an "aged non-impaired" group if their performance was <0.5 S.D. above the mean of "young" mice. Aged groups were then split into statistically similar "GPI-1046" and "vehicle" groups.

Daily treatment with 10 mg/kg GPI-1046 was initiated 3 days after the end of acquisition training, and continued through retention testing. Retention testing began after 3 weeks of dosing using the same methods as the acquisition phase. Swim Distances (cm) were analyzed in a 7×5 ANOVA including Groups and Blocks (1–5) as factors in the analysis, treating Blocks as a repeated measure.

The results showed that planned contrasts revealed that there were significant differences between the "young", and "aged impaired-vehicle and GPI-1046" treated groups at the end of the acquisition phase, $F_{1.58}=26.75$, $P=0.0001$, and $F_{1.58}=17.70$, $P=0.0001$ respectively. While there were no significant differences between the two "aged impaired" groups, $F_{1.58}=0.67$, $P=0.42$. During retention testing, however, "aged impaired-vehicle" treated animals performed significantly poorer than "aged impaired—GPI-1046", and "young" animals, $F_{1.69}=8.11$, $P=0.006$, and $F_{1.69}=25.45$, $P=0.0001$ respectively. There was no longer any statistically significant difference between the "young" and "aged impaired"—GPI-1046" treated groups during the retention phase, $F_{1.69}=3.09$, $P=0.08$. In summary, systemic treatment with GPI-1046 significantly enhanced spatial memory performance of mice with age-related spatial memory impairments.

EXAMPLES

The inventive compounds may be prepared by a variety of synthetic sequences that utilize established chemical transformations. A pathway to the compounds of Examples 1 through 4 is described in Scheme I. N-glyoxylproline derivatives may be prepared by reacting L-proline methyl ester with methyl oxalyl chloride as shown in Scheme I. The resulting oxamates may be reacted with a variety of carbon nucleophiles to obtain compounds used in the present invention.

Scheme I

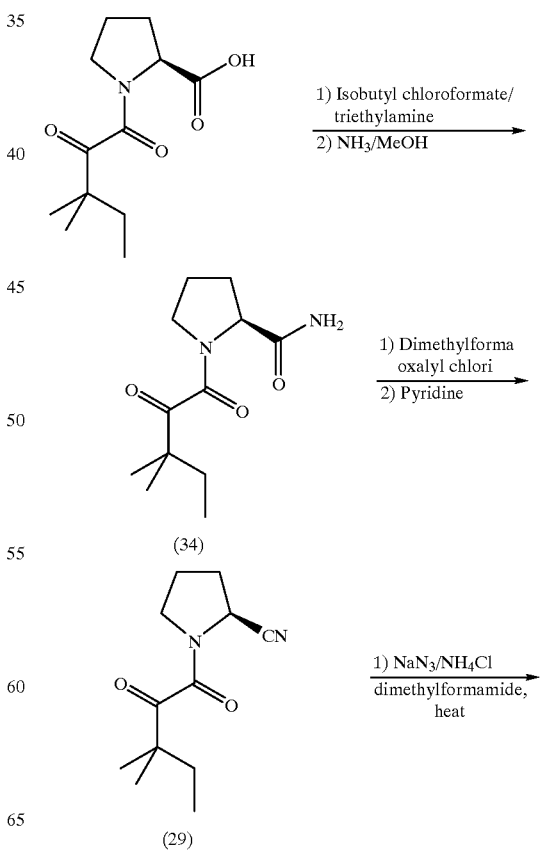

-continued

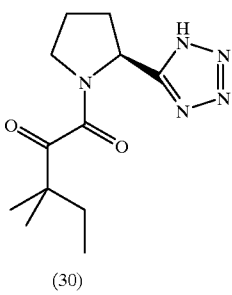

(30)

Example 1

Synthesis of (2S)-1-(3,3-dimethyl-1,2-dioxopentyl)-2-pyrrolidinecarboxylate(Compound 137)

a. Synthesis of (2S)-1-(1,2-dioxo-2-methoxyethyl)-2-pyrrolidinecarboxylate

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 mL) was added dropwise. The resulting mixture was stirred at 0° C. for 1.5 hr. After filtering to remove solids, the organic phase was washed with water, dried over MgSO₄ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR (CDCl₃): δ1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

b. Synthesis of methyl (2S)-1-(1,2-dioxo-3,3-dimethylpentyl)-2-pyrrolidinecarboxylate A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR (CDCl₃): δ0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

c. Synthesis of (2S)-1-(1,2-dioxo-3,3-dimethylpentyl)-2-pyrrolidinecarboxylic acid (Compound 137)

A mixture of methyl (2S)-1-(1,2-dioxo-3,3-dimethylpentyl)-2-pyrrolidinecarboxylate (2.10 g; 8.23 mmol), 1 N LiOH (15 ml), and methanol (50 mL) was stirred at 0° C. for 30 min and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification. $^1$H NMR (CDCl₃): δ0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

Inventive compounds containing bridged rings may be synthesized using the above synthetic schemes by substituting the substrates containing the N-heterocyclic ring structures with comparable substrates containing bridged ring structures.

Example 2

Synthesis of (2S)-1-(1,2-dioxo-3,3-dimethyloentyl)-2-pyrrolidinecarboxamide (Compound 34)

This example was prepared according to the process of Scheme II as follows.

Isobutyl chloroformate (20 mmol, 2.7 mL) was added to a solution containing (2S)-1-(1,2-dioxo-3,3-dimethylpentyl)-2-pyrrolidinecarboxylic acid (4.89 g, 20 mmol) (from Example 1) in 50 mL methylene chloride at −10° C. with stirring. After 5 minutes, ammonia was added dropwise (20 mmol, 10 mL of 2 M ethyl alcohol solution). The reaction was warmed up to room temperature after stirring at −10° C. for 30 minutes. The mixture was diluted with water, and extracted into 200 mL melhylene chloride. The organic extract was concentrated and further purified by silica gel to give 4.0 g of product as a white solid (81.8% yield). $^1$H NMR (CDCl₃): δ0.91 (t, 3H, J=7.5); 1.28 (s, 6H, each); 1.63–1.84 (m, 2H); 1.95–2.22 (m, 3H); 2.46 (m, 1H); 3.55–3.67 (m, 2H); 4.67 (t, 1H, J=7.8); 5.51–5.53 (br, 1H, NH); 6.80 (br, 1H, NH).

Example 3

Synthesis of (2S)-1-(1,2-dioxo-3,3-dimethylpentyl)-2-pyrrolidinecarbonitrile (Compound 29)

This example was prepared according to the process of Scheme III as follows.

To a solution of 0.465 mL DMF (6 mmol) in 10 mL acetonitrile at 0° C. was added 0.48 mL (5.5 mmol) of oxalyl chloride. A white precipitate formed immediately and was accompanied by gas evolution. When complete, a solution of 1.2 g (5 mmol) of (2S)-1-(1,2-dioxo-3,3-dimethylpentyl)-2-pyrrolidinecarboxamide (from Example 2) in 2.5 mL acetonitrile was added. When the mixture became homogeneous, 0.9 mL (11 mmol) pyridine was added. After 5 min., the mixture was diluted into water and extracted by 200 mL ethyl acetate. The organic layer was concentrated and further purified by silica gel to give 0.8 g product as a white solid (72% yield). $^1$H NMR (CDCl₃): δ0.87 (t, 3H, J=7.5); 1.22 (s, 3H); 1.24 (s, 3H); 1.80 (m, 2H); 2.03–2.23 (m, 4H); 3.55 (m, 2H); 4.73 (m, 1H).

Example 4

Synthesis of (2S)-1-(1,2-dioxo-3,3-dimethylpentyl)-2-pyrrolidinetetrazole (Compound 30)

This example was prepared according to the process of Scheme IV as follows.

A mixture of (2S)-1-(1,2-dioxo-3,3-dimethylpentyl)-2-pyrrolidinecarbonitrile (222 mg, 1 mmol) (from Example 3), NaN₃ (81 mg, 1.3 mmol) and NH₄Cl (70 mg, 1.3 mmol) in 3 mL DMF was stirred at 130° C. for 16 hours. The mixture was concentrated and purified by silica gel to afford 200 mg product as white solid (75.5% yield). $^1$H NMR (CDCl₃):

δ 0.88 (t, 3H, J=7.5); 1.22 (s, 6H); 1.68 (m, 2H); 2.05–2.36 (m, 3H); 2.85 (m, 1H); 3.54 (m, 1H); 3.75 (m, 1H); 5.40 (m, 1H).

Example 5

[1-(3,3-Dimethyl-2-oxopentanoyl)pyrrolidin-2-yl]-N-(2-thienylcarbonylamino)-formamide; molecular formula: $C_{17}H_{23}N_3O_4S$; molecular weight: 365.45 (Compound 140)

This example was prepared according to the process of Scheme V as follows.

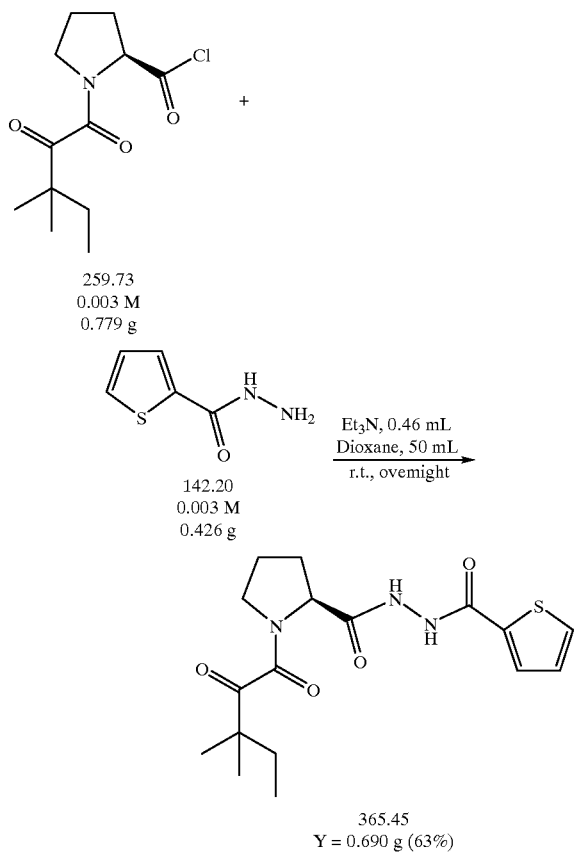

To a solution of thiophene carbonyl hydrazide (0.426 g, 3 mmol) and triethylamine (0.460 mL, 3.3 mmol) in dioxane (40 mL) was added dropwise a solution of acid chloride (0.779 g, 3 mmol) in dioxane (10 mT,) under stirring at room temperature within 5–7 min (immediate precipitation of triethylamine hydrochloride was observed as soon as first few drops were added). After addition is completed, the whole was stirred overnight at room temperature. The suspension formed was poured onto ice-water (100 g), and stirred for 15 min. Dichloromethane (50 mL) was added, and the reaction product was extracted (separating funnel) into organic layer. It was separated, dried over $Na_2SO_4$ (anhyd), filtered, and organic solvents were evaporated in vacuo. The oily solid obtained (0.690 g, 63%) was subjected to the column chromatography (silica gel, eluent—EtOAc:hexanes, 2:1). Fractlons with $R_f$ ca. 0.35 were collected. Evaporation of solvents gave 0.130 g of white microcrystals with m.p. 72–74° C. $^1H$ NMR (CDCl$_3$, 400 MHz): d 9.51 (br s, 1H); 9.31 (br s, 1H); 7.66–7.63 (m, 1H); 7.50–7.46 (m, 1H); 7.02–6.98 (m, 1H); 4.68–4.63 (m, 1H); 3.53–3.48 (m, 2H); 2.33–1.60 (m, 6H); 1.26 (s, 3H); 1.21 (s, 3H); 0.86 (t, J=7.5, 3H) Calcd for $C_{17}H_{23}N_3O_4S$: C, 55.87; H, 6.34; N, 11.50; S, 8.77. Found: C, 55.79; H, 6.57; N, 11.20; S, 8.52.

Example 6

3,3-Dimethyl-1-{2-[(4-nitrophenoxy)methyl]pyrrolidinyl}pentane-1,2-dione; molecular formula: $C_{18}H_{24}N^2O_5$; molecular weight: 348.40 (Compound 141)

This example was prepared according to the process of Scheme VI as follows.

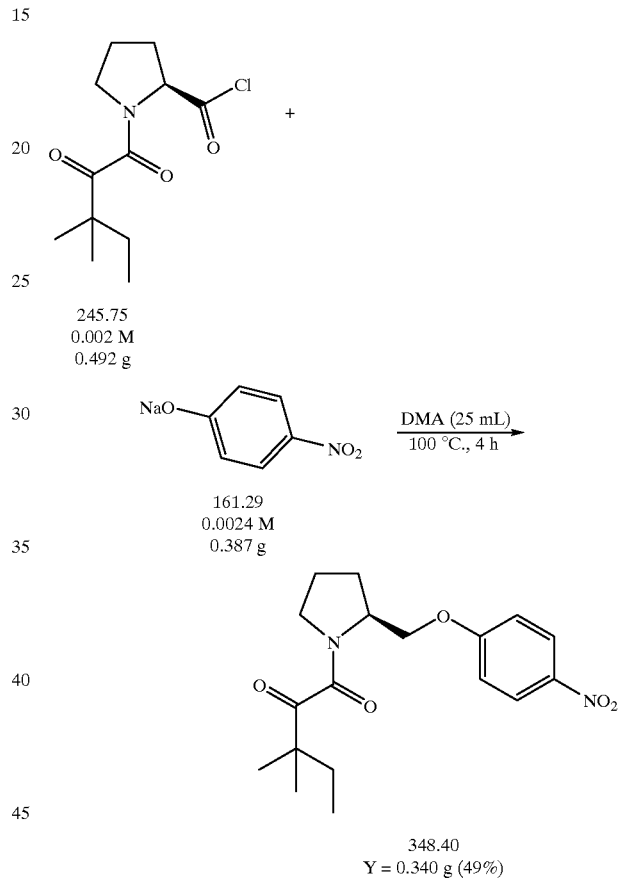

A solution of sodium 4-nitrophenolate (0.387 g, 2.4 mmol; prepared from NaOH and 4-nitrophenol in refluxing ethanol) and chloride (0.492 g, 2 mmol) in DMA (25 mL) were heated and stirred for 4 h. The mixture was poured onto ice-water (100 g), and organic products were extracted by dichloromethane (2×50 mL). Organic layer was separated, excessively washed with water (6×30 mL), separated, dried over over Na SO; (anhyd), filtered, and organic solvents were evaporated in vacuo. The brown oil obtained (0.340 g, 49%) was twice subjected to the column chromatography (silica gel, eluent—EtOAc:hexanes, 1:1). Fractions with $R_f$ ca. 0.45 were collected. Evaporation of solvents gave 0.145 g of yellow oil. $^1H$ NMR (CDCl$_3$, 400 MHz): d 8.19 (d, J=7.1, 2H); 7.03–6.92 (m, 2H); 4.51–4.42 (m, 1H); 4.35–4.22 (m, 2H); 3.50–3.42 (m, 2H); 2.18–1.64 (m, 6H); 1.20 (s, 3H); 1.19 (s, 3H); 0.86 (t, J=7.5, 3H). Calcd for $C_{18}H_{24}N_2O_5$: C, 62.05; H, 6.94; N, 8.04. Found: C, 61.91; H, 7.02; N, 7.80.

Example 7

2-[1-(3,3-Dimethyl-2-oxopentanoyl)pyrrolidin-2-yl]ethanenitrile; molecular formula: $C_{13}H_{20}N_2O_2$; molecular weight: 236.31 (Compound 28)

This example was prepared according to the process of Scheme VII as follows.

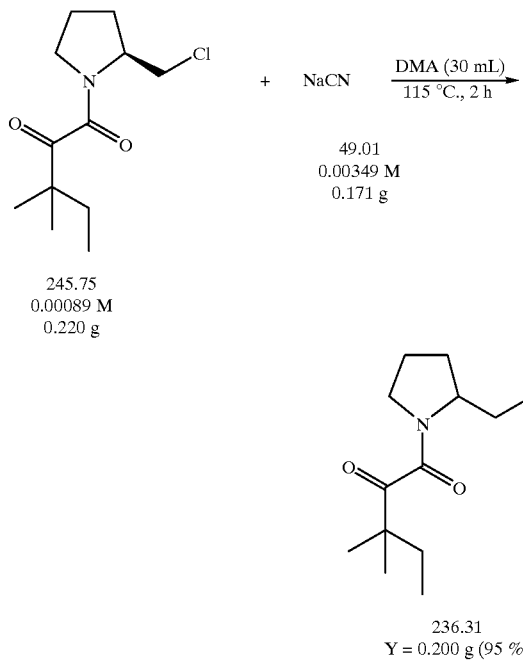

A mixture of chloride (0.220 g, 0.89 mmol) and sodium cyanide (0.171 g, 3.49 mmol) in DMA (30 mL) was stirred upon heating at 115° C. After cooling to a room temperature, water (50 mL) was added to the mixture, and the whole was stirred for 30 min. Diethyl ether (50 mL) was added, and the organic products were extracted (separating funnel) into organic layer, which was separated and dried over $MgSO_4$ (unhyd). Evaporation of solvents gave light yellow oil, which still contained DMA (NMR). Extraction was repeated using mixture of dlchloromethane (50 mL) and water (30 mL). Separation of organic layer, drying over $Na_2SO_4$ (anhyd), evaporation of the solvent, and pumping of the product on the vacuum line (5 mm Hg, 2 days) gave white solid, which was subjected to the column chromatography (silica gel, elueno—EtOAc:hexanes, 1:2). Fractions with $R_f$ ca. 0.65 were collected. Evaporation of solvents gave 0.115 g of white waxy solid with m.p. 91–93° C. $^1$H NMR (CDCl$_3$, 400 MHz): d 4.21 (dd, J=3.6, 11.6 Hz, 1H); 3.77–3.63 (m, 2H); 3.58– 3.41 (m, 2H); 2.13–2.03 (m, 2H); 1.95–1.78 (m, 1H); 1.74–1.66 (m, 1H); 1.53–1.41 (m, 2H); 1.46 and 1.14 (two s, 3+3H); 0.90 (t, J=7.5 Hz, 3H). Calcd for $C_{13}H_{20}N_2O_2$: C, 66.07; H, 8.53; N, 11.85. Found: C, 66.24; H, 8.51; N, 11.93.

Example 8

1-[2-(3-Ethyl(1,2,4-oxadtazol-5-yl))pyrrolidinyl]-3,3-dimethylpentane-1,2-dione; molecular formula: $C_{15}H_{23}N_3O_3$; molecular weight: 293.36 (Compound 142)

This example was prepared according to the process of Scheme VIII as follows.

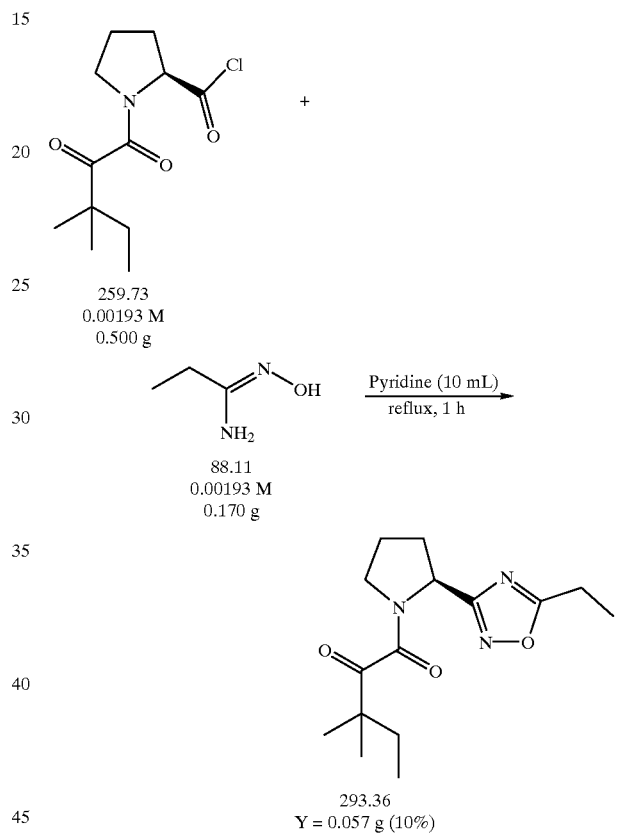

To a stirred suspension of amidoxime (0.170 g, 1.93 mmol) in dry pyridine was added an acid chloride (0.500 g, 1.93 mmol) under nitrogen at room temperature. The whole was brought to reflux; stirring and refluxing was continued for 1 h. The brownish-colored solution was cooled down to room temperature, diluted with water (30 mL), and extracted with EtOAc (3×30 mL). Combined organic layers were washed with water (50 mL), HCl (1N in water, 150 mL), separated, and dried over $MgSO_4$. Filtration and evaporation of the solvents in vacuo gave yellowish oil. It was purified by column chromatography (silica gel, eluent—EtOAc:hexanes, 1:1) to give a clear oil (0.057 g, 10%). $^1$H NMR (CDCl$_3$, 400 MHz): δ5.31 (d, 1H); 3.62–3.65 (m, 2H); 2.71–2.76 (m, 2H); 2.06–2.15 (m, 4H); 1.64–1.85 (m, 2H); 1.32 (t, J=7.2 Hz, 3H); 1.24(s, 3H); 1.22 (s, 3H); 0.88 (t, J=7.5 Hz, 3H). Calcd for $C_{15}H_{23}N_3O_3$: C, 61.41; H, 7.90; N, 14.32. Found: C, 61.22; H, 7.87; N, 13.76.

Example 9

1-{2-[3-(4-Fluorophenyl) (1,2,4-oxadiazol-5-yl)]pyrrolidinyl}-3,3-dimethylpent-ane-1,2-dione; molecular formula: $C_{19}H_{22}FN_3O_3$; molecular weight: 359.40 (Compound 143)

This example was prepared according to the process of Scheme IX as follows.

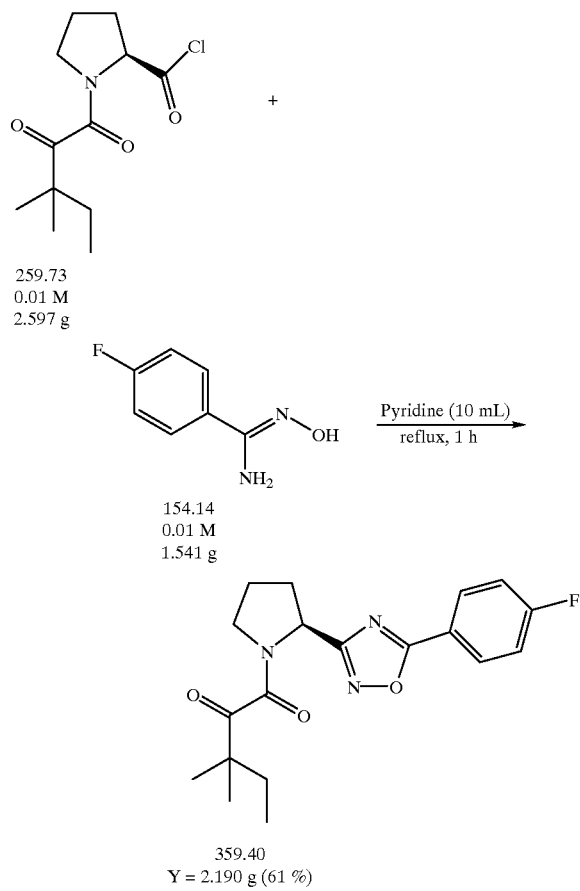

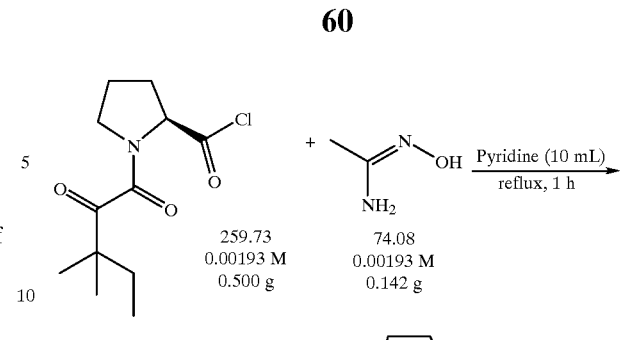

The procedure is identical to that used in the previous case. Crude product was isolated as a yellow oil (2.190 g, 61%) and was purified by column chromatography (silica gel; eluent—EtOAc:hexanes 1:1). Fractions with $R_f$ ca. 0.65 were collected. Evaporation of solvents gave 1.150 g of light-yellow oil. $^1$H NMR (CDCl$_3$, 400 MHz): δ8.08–8.04 (m, 2H); 7.19–7.14 (m, 2H); 5.56–5.51 and 5.42–5.37 (2m—2 rotamers, 1H); 3.91–3.84 and 3.75–3.65 (2m-2 rotamers, 2H); 2.50–2.05 (m, 4H); 1.85–1.60 (m, 2H); 1.27, 1.24, 1.19, and 1.09 (4s—2 rotamers, 3H); 0.88 (t, J=7.5, 3H). Calcd for $C_{19}H_{22}FN_3O_3$: C, 63.50; H, 6.17; N, 11.69. Found: C, 63.58; H, 6.16; N, 11.70.

Example 10

3,3-Dimethyl-1-[2-(3-methyl(1,2,4-oxadiazol-5-yl))pyrrolidinyl]pentane-1,2-di-one; molecular formula: $C_{14}H_{21}N_3O_3$; molecular weight: 279.33 (Compound 144)

This example was prepared according to the process of Scheme X as follows.

The procedure is identical to that used in the previous case. Crude product was isolated as a yellow oil and was purified by column chromatography (silica gel; eluent—EtOAc:hexanes 1:1). Fractions with $R_f$ ca. 0.75 were collected. Evaporation of solvents gave 0.141 g of light-yellow oil. $^1$H NMR (CDCl$_3$, 400 MHz): δ; 5.35 (m, 1H); 3.64 (m, 2H); 2.38 (s, 3H); 2.07–2.10 (m, 4H); 1.68–1.76 (m, 2H); 1.21 (s, 3H); 1.19 (s, 3 H); 0.86 (t, J=7.5 Hz, 3H). Calcd for $C_{14}H_{21}N_3O_3$: C, 60.20; H, 7.58; N, 15.04; found: C, 60.05; H: 7.72; N: 14.91.

Example 11

[1-(3,3-Dimethyl-2-oxopentanoyl)pyrrolidin-2-yl]-N-[(methylsulfonyl)amino]-formamide; molecular formula: $C_{13}H_{23}N_3O_3S$; molecular weight: 333.40 (Compound 145)

This example was prepared according to the process of Scheme XI as follows.

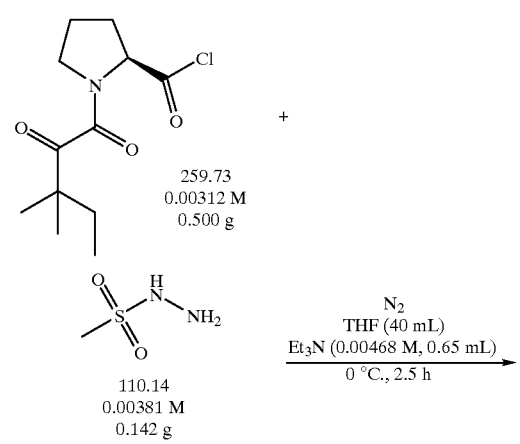

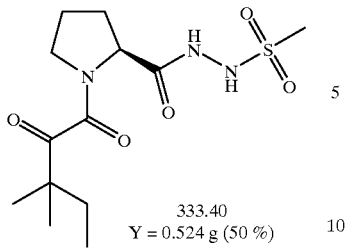

333.40
Y = 0.524 g (50 %)

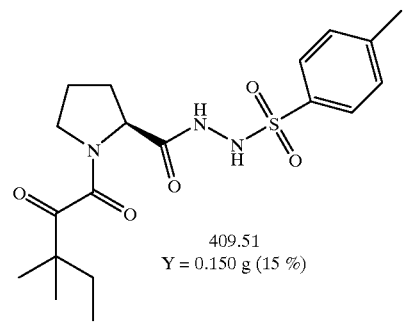

409.51
Y = 0.150 g (15 %)

Sulfonyl hydrazide (0.142 g, 3.81 mmol) and triethylamnine (0.65 mL, 4.68 mmol) were dissolved in dry THF (30 mL) under stirring at 0° C. A solution of acid chloride (0.500 g, 3.12 mmol) in dry THF (10 mL) was added dropwise within 10 min, and stirring was continued for another 2 h 20 min at 0° C. A mixture was diluted with dichloromethane (50 mL), washed with water (2×50 mL), and aqueous NaHCO$_3$ (10% w/w, 50 mL). Organic layer was separated, dried over MgSO$_4$ (anhyd), filtered. Removal of the solvents in vacuo gave crude product as a pink oil, which was purified by column chromatography (silica gel, eluent—EtOAc:hexanes 3:1). Fractions with $R_f$ ca. 0.50 were collected; evaporation of the solvents gave 0.524 g of puffy white solid. $^1$H NMR (CDCl$_3$, 400 MHz): δ8.90 (br s, 1H); 6.80 (br s, 1H); 4.50 (m, 1H); 3.52 (m, 2H); 3.01 (s, 3H); 2.07–2.10 (m, 4H); 1.68–1.76 (m, 2H); 1.21 (s, 3H); 1.19 (s, 3 H); 0.86 (t, J=7.5 Hz, 3H). Calcd for C$_{13}$H$_{23}$N$_3$O$_5$S: C, 46.83; H, 6.95; N, 12.60, S: 9.62. Found: C, 47.16; H, 7.26; N, 12.29; S, 9.39.

To a stirred solution of the acid (0.579 g, 2.4 mmol) and sulfonyl hydrazide (0.372 g, 2.0 mmol) in dry 1,2-dichloroethane was added carbonyl-bis-imidazole (0.389 g, 2.4 mmol) in portions over 10 min period at room temperature. Stirring at room temperature was continued until the gas evolution was ceased. The mixture was then refluxed for 20 h, and solvent was evaporated in vacuo. The oil formed was dissolved in chloroform (50 mL), and washed with Na$_2$CO$_3$ (sat., 20 mL) and water (20 mL). Organic layer was separated, dried over Na$_2$SO$_4$ (anhyd), filtered, and the solvent was evaporated in vacuo to give crude product in the form of heavy oil. It was purified by column chromatography (silica gel, eluent: EtOAc:hexanes, 1:1). Fractions with $R_f$ ca. 0. 30 were collected; evaporation of the solvents gave 0.150 g of white solid, which was triturated with a mixture of ether:hexanes (1:5 v/v, 15 mL). Filtration of the suspension afforded 0.100 g of analytically pure product as white microcrystals with m.p. 59–61° C. $^1$H NMR (CDCl$_3$, 400 MHz): d 9.08 (br s, 1H); 7.78 (d, J=7.5, 2H); 7.29 (d, J=7.5, 2H); 4.44–4.39 (m, 1H); 3.39–3.35 (m, 2H); 2.42 (s, 3H); 1.93–1.68 (m, 6H); 1.24–1.13 (m, 6H); 0.86 (t, J=5.3, 3H). Calcd for C$_{19}$H$_{27}$N$_3$O$_5$S: C, 55.73; H, 6.65; N, 10.26; S, 7.83. Found: C, 55.49; H, 6.63; N, 10.14; S, 7.85.

Example 12

[1-(3,3-Dimethyl-2-oxopentanoyl)pyrrolidin-2-yl]-N-{[(4-methylphenyl)sulfonyl]-amino}formamide; molecular formula: C$_{19}$H$_{27}$N$_3$O$_5$S; molecular weight: 409.51 (Compound 146)

This example was prepared according to the process of Scheme XII as follows.

Example 13

[1-(3,3-Dimethyl-2-oxopentanoyl)pyrrolidin-2-yl]-N-([(4-fluorophenyl)sulfonyl]-aminoiformamide; molecular formula C$_{18}$H$_{24}$FN$_3$O$_5$S; molecular weight 413.47 (Compound 147)

This example was prepared according to the process of Scheme XIII as follows.

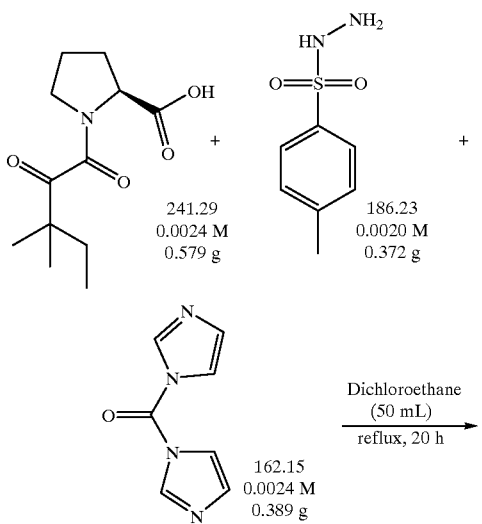

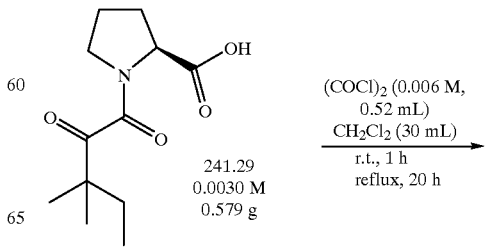

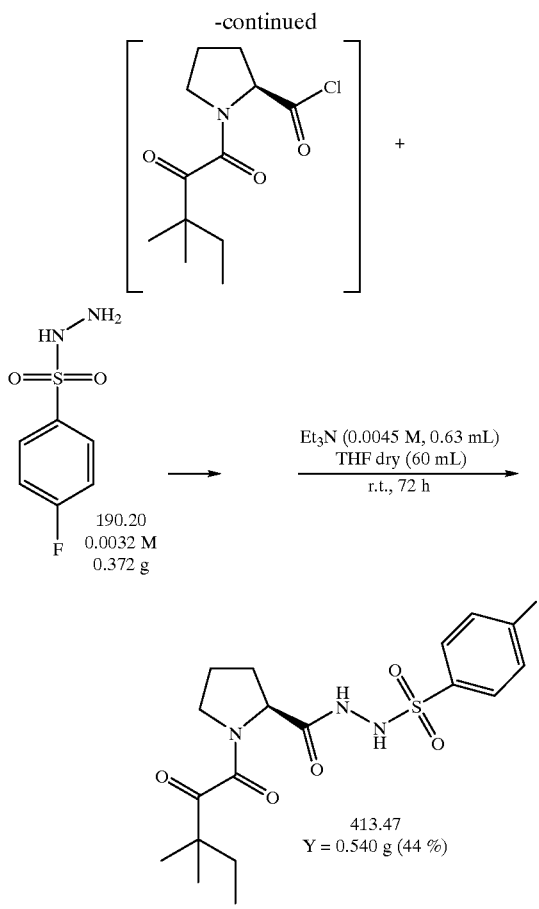

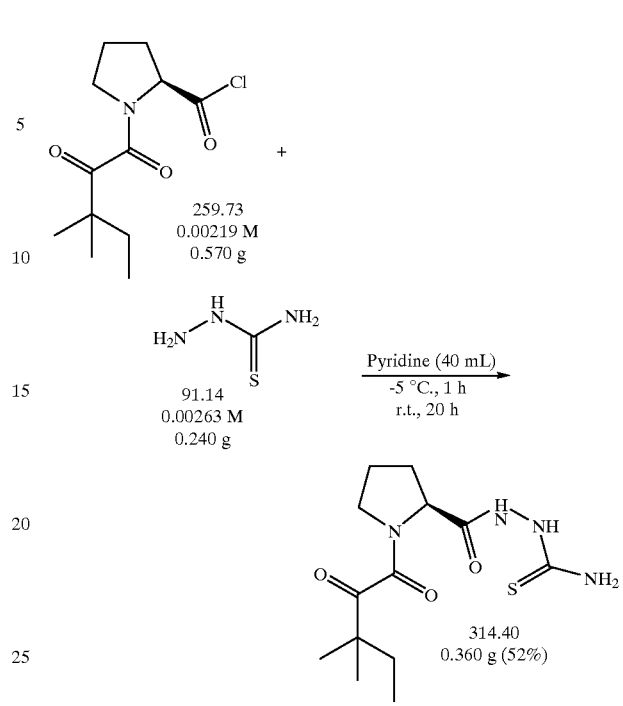

A solution of acid (0.724 g, 3.0 mmol) and oxalyl chloride (0.52 mL, 6.0 mmol) in dichloromethane (30 mL) was stirred at room temperature for 1 h. Within this time the gas evolution became steady, then the mixture was brought to reflux, and refluxing and stirring were continued overnight. The solvent was removed in vacuo, resulting yellow oil was dissolved in dry THF (10 mL) and was added dropwise to a stirred solution of hydrazide (0.372 g, 3.2 10 mmol) and triethylamine (0.63 mL, 4.5 mmol) in dry THF (50 mL) at room temperature. The formed white suspension was stirred for 72 h, then transferred into separating funnel.

Dichloromethane (30 mL) and HCl (1N, 30 mL) were added, and the whole was shaken for 5 min. Organic layer was separated, washed with aq. $Na_2CO_3$ (30% w/w, 75 mL), then with water (50 mL), separated, dried over $Na_2SO_4$ (anhyd), filtered, and the solvent was evaporated in vacuc to give 0.540 g of heavy oil. Crude product was purified by column chromatography (silica gel, eluent: EtOAc:hexanes, 2:1). Fractions with $R_f$ ca. 0.65 were collected; evaporation of the solvents gave 0.100 g of colorless oil, which solidified upon standing; m.p. 57–60° C. $^1$H NMR (CDCl$_3$, 400 MHz): d 9.22 (br s, 1H); 7.98–7.92 (m, 2H); 7.70 (br s, 1H); 7.22–7.16 (m, 2H); 4.42–4.38 (m, 1H); 3.42–3.43 (m, 2H); 2.02–1.62 (m, 6H); 1.19 and 1.18 (2 s, 6H); 0.86 (t, J=7.5 Hz, 3H). Calcd for $C_{18}H_{24}FN_3O_5S$. 0.17 $H_2O$: C, 51.90; H, 5.89; N, 10.09; S, 7.70. Found: C, 52.29; H, 6.17; N, 9.62; S, 7.31.

Example 14
(2S)-3,3-Dimethyl-1-[2-(5-sulfanyl(4H-1,2,4-triazol-3-yl))pyrrolidinyl]-pentane-1,2-dione; molecular formula: $CH_{13}H_{20}N_4O_2S$; molecular weight: 296.393 (Compound 148)

This example was prepared according to the process of Scheme XIV as follows.

A solution of acid (0.598 g, 2.48 mmol) and oxalyl chloride (0.22 mL, 2.48 mmol) in dichloromethane (30 mL) was stirred at room temperature for 1 h. Within this time the gas evolution became steady, then the mixture was brought to reflux, and refluxing and stirring were continued overnight. Phe solvent was removed in vacuo. Resulting oil was treated with a solution of thiosemicarbazide (0.294 g, 3.22 mmol) and triethylamine (0.45 mL, 3.22 mmol) in DMA (15 mL) upon stirring at room temperature for 20 h. A solution obtained was poured into water (150 mL) and extracted with dichloromethane (3×30 mL). Combined organ Lc extracts were dried over $Na_2SO_4$ (anhyd), and the solvent was evaporated in vacuo. The crude intermediate was kept in vacuo for 6 h, and then dissolved in NaOH (1N, 10 mL). The solution was stirred and heated at 60° C. for 3 h, and then at room temperature—for 2 h. It was then acidified with HCl (1N, to pH ca. 1), and extracted with dichloromethane (2×30 mL). Combined organic layers were washed with water (2×30 mL), separated, dried over $Na_2SO_4$ (anhyd), and the solvent was evaporated in vacuo to give 0.060 g of amber oil. It was kept in vacuo for 60 h to form solid, which was purified by column chromatography (silica gel, eluent: EtOAc:hexanes, 2:1). Fractions with $R_f$ ca. 0.30 were collected; evaporation of solvents gave 0.025 g of white foamy solid. $^1$H NMR (CDCl$_3$, 400 MHz): d 12.2 (br s, 1H); 11.6 (br s, 1H); 5.19 (dd, J=3.6, 5.1 Hz, 1H); 3.58–3.45 (m, 2H); 2.58–2.50 (m, 1H); 2.29–2.11 (m, 2H); 2.07–2.00 (m, 1H); 1.72 (q, J=1.4, 6.2, 2H); 1.22–1.17 (m, 6H); 0.87 (t, J=4.4 Hz, 3H). $^{13}$C NMR (CDCl$_3$, 125 MHz) d 206.2, 166.6, 166.5, 151.9, 52.3, 47.7, 47.0, 32.3, 27.8, 24.9, 23.6, 23.4, 8.9. Calcd for $C_{13}H_{20}N_4O_2S$: C, 52.68; H, 6.80; N, 18.90; S, 10.82. Found: C, 52.70; H, 6.81; N, 18.66; S, 10.94.

Example 15
(2S)-3,3-Dimethyl-1-[2-(pyrrolidinylmethyl) pyrrolidinyl]pentane-1,2-dione; molecular formula: $C_{16}H_{28}N_2O_2$; molecular weight: 280.409 (Compound 149)

This example was prepared according to the process of Scheme XV as follows.

65

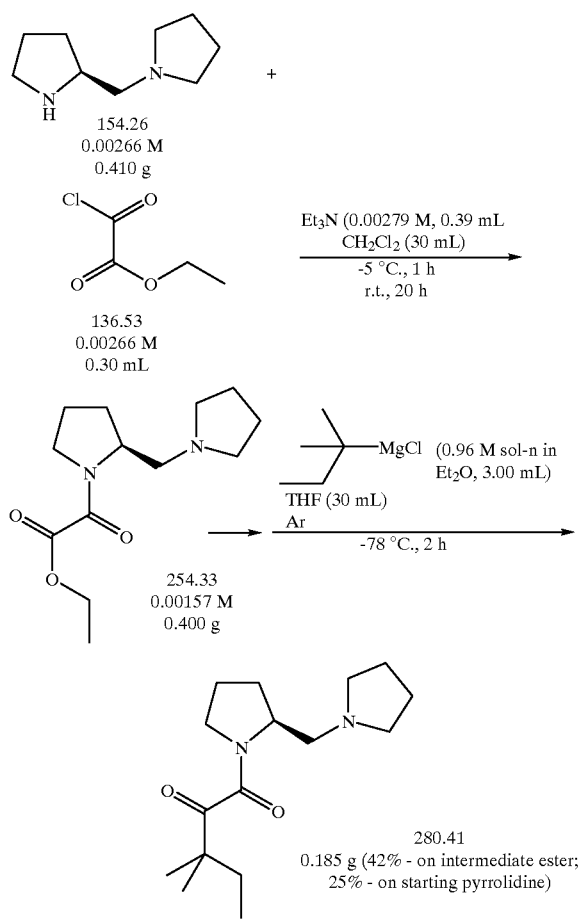

A solution of ethyl chlorooxoacetate (0.30 mL, 2.66 mmol) in dichloromethane (10 mL) was added dropwise within 5 min to a stirred and chilled solution of 2-(pyrrolidinylmethyl)pyrrolidine (0.410 g, 2.66 mmol) and triethylamine (0.39 mL, 2.79 mmol) in dichloromethane (20 mL). After addition was completed, the stirring was continued at −5° C. for another 50–55 min, and at room temperature for 20 h. Water (50 mL.) and dichloromethane (30 mL) were added, and the mixture was transferred into separating funnel. After extraction, organic layer was separated and dried over $Na_2SO_4$ (anhyd). Evaporation of the solvent in vacuo gave 0.400 g of heavy yellow oil. It was kept in vacuo for 20 h, then dissolved in dry THF (30 mL) and chilled to −78° C. upon stirring. An ethereal solution of Grignard reagent (0.96 M, 3.00 mL) was added dropwise to the latter solution within 15–20 min, and the whole was stirred for another 1 h 45 min. A mixture was quenched by addition of $NH_4Cl$ (sat., 20 mL) and water (50 mL), stirred for 10 min, and extracted with dichloromethane (2×50 mL). Combined organic layers were washed with water (50 mL) and dried over $Na_2SO_4$ (anhyd). Evaporation of the solvent in vacuo gave 0.370 g of yellow oil. Crude product was purified by column chromatography (silica gel, eluent: $CHCl_3$:MeOH, 10:1). Fractions with $R_f$ ca. 0.10 (in EtOAc:hexanes, 2:1) were collected; evaporation of solvents gave 0.185 g of heavy yellow oil. $^1H$ NMR ($CDCl_3$, 400 MHz): d 4.29–4.22 and 3.99–3.92 (two rotamers, m, 1H); 3.61–3.52 and 3.47–3.39 (two rotamers, m, 2H); 2.73–2.43 (complex m, 6H); 2.14–1.68 (complex m, 10H); 1.23–1.20 (two rotamers, set of singlets, 6H); 0.87 (t, J=7.5 Hz, 3H). Calcd for

66

$C_{16}H_{28}N_2O_2$: C, 68.53; H, 10.06; N, 9.99. Found: C, 68.78; H, 9.87; N, 9.77.

Example 16

(2S)-N-[(Aminothioxomethyl)amino][1-(3,3-dimethyl-2-oxopentanoyl)pyrrolid-in-2-yl] formamide; molecular formula: $C_{13}H_{22}N_4SO_3$; molecular weight: 314.41 (Compound 150)

This example was prepared according to the process of Scheme XVI as follows.

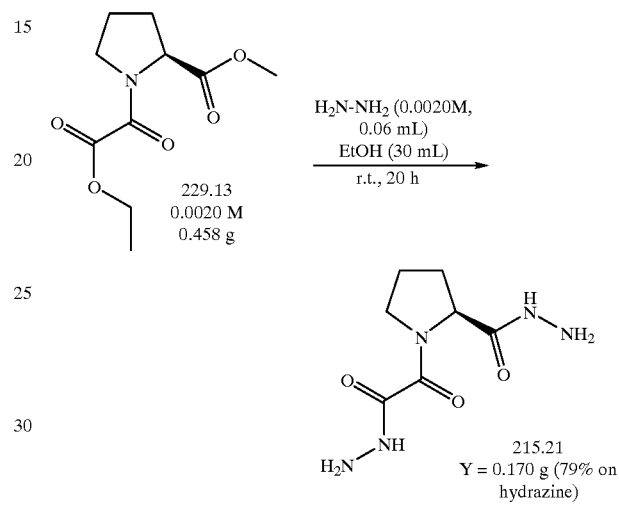

A solution of acid chloride (0.570 g, 2.19 mmol) in dry pyridine (10 mL) was added to a stirred and chilled suspension of thiosemicarbazide (0.240 g, 2.63 mmol) in dry pyridine (30 mL). The mixture was allowed to warm up to room temperature, and stirring was continued for 20 h. Solvent was evaporated in vacuo, hot water (50 mL) was added to the residue, and the whole was stirred for 5 min at room temperature. $NH_4Cl$ (sat., 20 mL) was added Lo the mixture, followed by extraction with dichloromethane (2×50 mL). After separation, combined organic layers were dried over $Na_2SO_4$ (anhyd). Evaporation of the solvent in vacuo gave 0.360 g of oily yellowish solid. Crude product was purified by column chromatography (silica gel, eluent: EtOAc:hexanes, 3:1 to 5:1). Fractions with $R_f$ ca. 0.20 were collected; evaporation of solvents gave 0.077 g of white puffy solid. $^1H$ NMR ($CDCl_3$, 400 MHz): d 9.60 (br s, 1H); 8.40 (br s, 1H); 7.20–7.30(m, 2H); 4.53–4.56 (m, 1H); 3.54–3.55 (m, 2H); 2.18–2.19 (m, 2H); 2.00–2.10 (m 2H); 1.60–1.68 (m, 2H); 1.18 (s, 3H); 1.16 (s, 3 H); 0.83 (m, 3H). Calcd for $C_{13}H_{24}N_4SO_3$: C, 49.66; H, 7.05; N, 17.82; S, 10.20. Found: C, 49.73; H, 7.15; N, 17.65; S, 10.22.

Example 17

(2S)-1-[2-(Benzotriazol-1-ylcarbonyl)pyrrolidinyl]-3,3-dimethylpentane-1,2-dione; molecular formula: $C_{18}H_{22}N_4O_3$; molecular weight: 342.39 (Compound 151)

This example was prepared according to the process of Scheme XVII as follows.

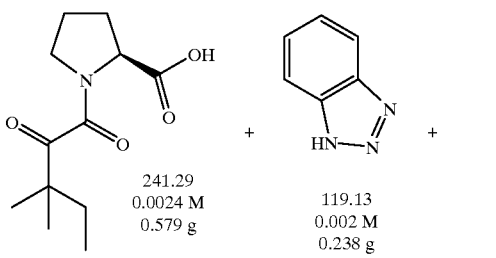

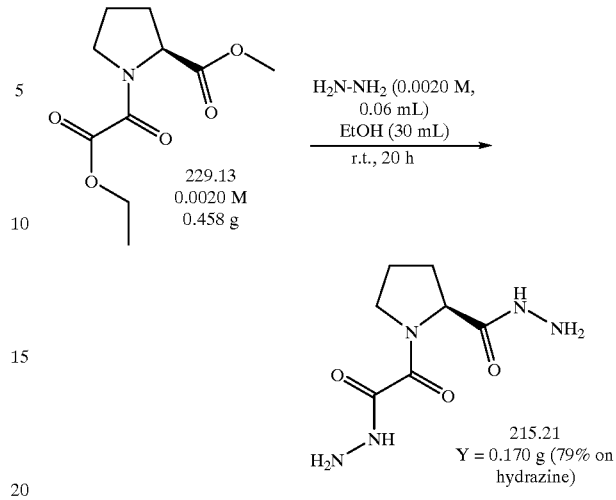

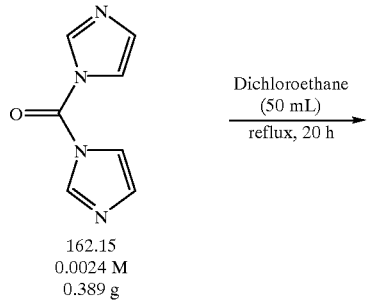

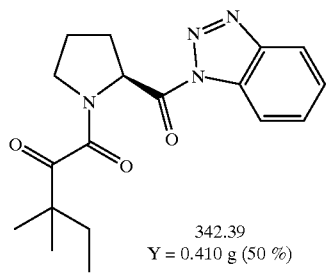

The procedure is identical to that used in the preparation of compound #8. Crude product was purified by column chromatography (silica gel; eluent—EtOAc:hexanes 1:2). Fractions with $R_f$ ca. 0.50 (in EtOAc:hexanes 1:1) were collected. Evaporation of solvents gave 0.410 g of clear oil (slowly solidifies upon standing). $^1$H NMR (CDCl$_3$, 400 MHz): δ8.29–8.27 (m, 1H); 8.15–8.13 (m, $^1$H); 7.70–7.65 (m, 1H); 7.56–7.50 (m, 1H); 6.00–5.95 (m, 1H); 3.75–2.65 (m, 2H); 2.67–2.60 (m, 1H); 2.23–2.09 (m, 3H); 1.85–1.70 (m, 2H); 1.30/1.26/1.23/1.16 (s—all 4 peaks belong to 2 rotamers, 6H); 0.89/0.76 (2 t—both belong to 2 rotamers, J=7.5 Hz, 3H). Calcd for C$_{18}$H$_{22}$N$_4$O$_3$: C, 63.14; H, 6.48; N, 16.36. Found: C, 62.91; H, 6.44; N, 16.22.

Example 18

N-Amino-2-[2-(N-aminocarbamoyl)pyrrolidinyl]-2-oxoethanamide; molecular formula: C$_7$H$_{13}$N$_5$O$_3$; molecular weight: 215.21 (Compound 152)

This example was prepared according to the process of Scheme XVIII as follows.

Anhydrous hydrazine (0.06 mL, 2 mmol) was added at room temperature to a stirred solution of diester (0.458 g, 2 mmol) in ethanol (30 mL,). Stirring was continued for 20 h, precipitate formed was filtered, washed with diethyl ether, and air-dried. White solid (0.170 g) with m.p. >200° C. $^1$H NMR (CDCl$_3$, 400 MHz): δ9.77 (br s, 1H); 9.10/9.02 (s, 1H); 4.93–4.90/4.28–4.23 (m, 1H); 4.44/4.37 (br s, 2H); 4.17 (br s, 2H); 3.75–3.70 (m, 1H); 3.69–3.78 (m, 1H); 2.19–1.98 (m, 1H); 1.97–1.66 (m, 3H). Calcd for C$_7$H$_{13}$N$_5$O$_3$: C, 39.07; H, 6.09; N, 32.54. Found: C, 38.97; H, 6.10; N, 32.36.

Example 19

2-[1-(3,3-Dimethyl-2-oxopentanoyl)-2-piperidyl] acetic acid; molecular formula: C$_{14}$H$_{23}$NO$_4$; molecular weight: 269.34 (Compound 153)

This example was prepared according to the process of Scheme XIX as follows.

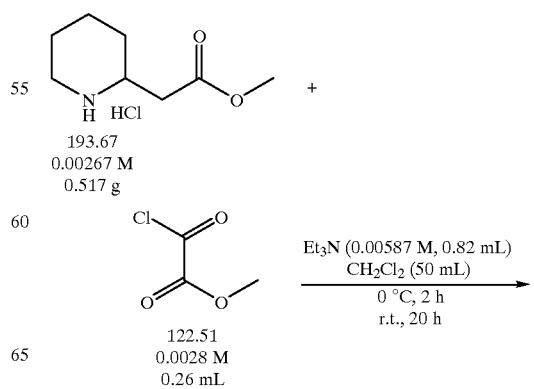

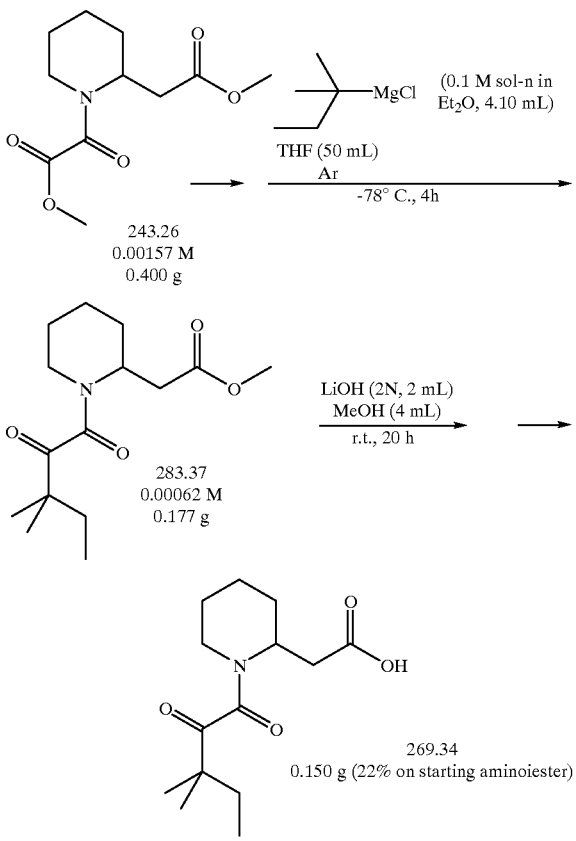

A solution of methyl chlorooxoacetate (0.26 mL, 2.80 mmol) in dichloromethane (10 mL) was added dropwise within 10 min to a stirred and chilled mixture of amino ester hydrochloride (0.517 g, 2.67 mmol) and triethylamine (0.82 mL, 5.87 mmol) in dichloromethane (40 mL). After addition was completed, the stirring was continued at 0° C. for a total of 2 h, and at room temperature for 20 h. Water (50 mL) was added, and the mixture was transferred into separating funnel. After extraction, organic layer was separated, washed with $Na_2CO_3$ (sat., 15 mL), water (50 mL), and HCl (1N, 30 mL). Organic layer was separated and dried over NaSOC (anhyd). Evaporation of the solvent in vacuo gave 0.405 g of light yellow oil. It was then dissolved in dry THF (50 mL) and chilled to −78° C. upon stirring. An ethereal solution of Grignard reagent (1 M, 4.10 mL) was added dropwise to the latter solution within 15–20 min, and the whole was stirred for another 3 h 45 min. A mixture was quenched by addition of $NH_4Cl$ (sat., 25 mL) and ice-water (100 g+50 mL), stirred for 5 min, and extracted with diethyl ether (3×40 mL). Combined organic layers were separated and dried over $MgSO_4$ (anhyd). Evaporation of the solvent in vacuo gave 0.200 g of light oil. Crude product was purified by column chromatography (silica gel, eluent: EtOAc:hexanes, 1:1). Fractions with $R_f$ ca. 0.55 were collected; evaporation of solvents gave 0.177 g of colorless oil. (Analyzed: Calcd for $C_{15}H_{25}NO_4$: C, 63.58; H, 8.89; N, 4.94. Found: C, 63.79; H, 9.00; N. 4.94). The preceding oil was dissolved in MeOH (4 mL), and solution of LiOH (2N, 2 mL) was added upon stirring at room temperature. Stirring was continued for 20 h. Dichloromethane (50 mL) and water (30 mL) were added, and the whole was shaken in separating funnel for 5 min. Aqueous layer was separated; organic layer was additionally washed with NaOH (1N, 25 mL), and the combined aqueous layers were acidified with HCl (1N, until pH ca. 2). Dichloromethane (50 mL) was added, and the whole was shaken in separating funnel for 3 min. Organic layer was separated and dried over $Na_2SO_4$ (anhyd) Evaporation of the solvent in vacuo gave 0.150 g of clear oil with $R_f$ ca. 0.05 (EtOAc:hexanes, 4:1). $^1H$ NMR (CDCl$_3$, 400 MHz): d 5.16–5.07 and 4.41–4.46 (2m, $^1H$); 3.93–4.01 and 3.33–3.26 (2m, 1H); 3.17–3.08 and 2.94–2.87 (2m, 1H); 2.73–2.60 (m, 2H); 1.82–1.40 (m, 8H); 1.24, 1.21, and 1.18 (3s, 6H); 0.92–0.84 (m, 3l). Calcd for: $C_{14}H_{23}NO_4$: C, 62.43; H, 8.61; N, 5.20. Found: C, 62.43; H, 8.64; N, 5.06.

Example 20

1-(2-{[4-(2H-Benzo[3,4-d]1,3-dioxolen-5-ylmethyl) piperazinyl]carbonyl}pyrrol-idinyl)-3,3-dimethylpentane-1,2-dione; molecular formula: $C_{24}H_{33}N_3O_5$; molecular weight: 443.54 (Compound 154)

This example was prepared according to the process of Scheme XX as follows.

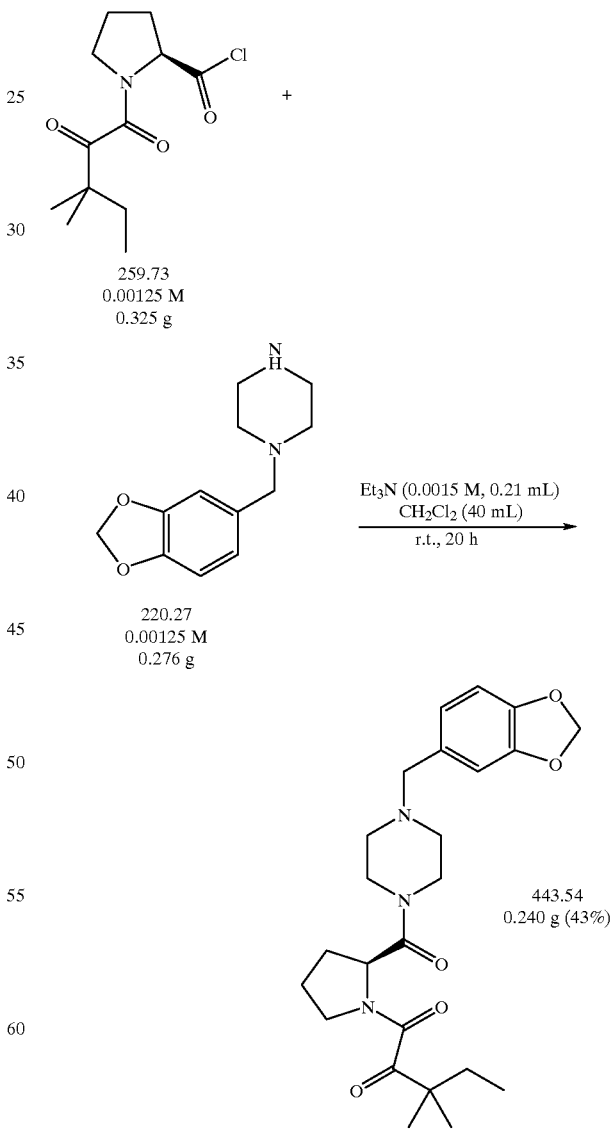

A solution of acid chloride (0.325 g, 1.25 mmol) in dichloromethane (10 mL) was added within 5 min to a stirred solution of piperazine derivative (0.276 g, 1.25 mmol) and triethylamine (0.21 mL, 1.50 mmol) in dichloromethane (30 mL) at room temperature. Stirring was continued for another 20 h. Water (50 mL) was added, and the whole was transferred into separating funnel. After extraction, organic layer was separated and washed subsequently with HCl (1N, 30 mL), NAOH 91N, 30 mL), and water (50 mL), separated again, and dried over $Na_2SO_4$ (anhyd). Evaporation of the solvent in vacuo gave 0.450 g of yellow oil. Crude product was purified by column chromatography (silica gel, eluent: EtOAc:hexanes, 3:1, then 4:1). Fractions with $R_f$ ca. 0.15 (in EtOAc:hexanes, 3:1) were collected; evaporation of solvents gave 0.240 g of clear yellow oil. $^1$H NMR (CDCl$_3$, 400 MHz): d 6.87 and 6.85 (2s, 1H); 6.76–6.71 (m, 2H); 5.94 (s, 2H); [4.99 (dd, J=4.6 and 8.4) and 4.86 (dd, J=3.9 and 8.4)—total for 1H]; 3.76–3.35 (m, 8H); 2.72–1.52 (m, 10H); [1.30, 1.28, 1.22, 1.12-4s, total for 6H]; [0.87 (t, J=7.6) and 0.80 (t, J=7.6)—total for 3H]. Calcd for $C_{24}H_{33}N_3O_5 \cdot 0.4H_2O$: C, 5 63.95; H, 7.56; N, 9.32. Found: C, 64.07; H, 7.48; N, 9.02.

Example 21

1-[2-({4-[Bis(4-fluorophenyl)methyl]piperazinyl}carbonyl)pyrrolidinyl]-3,3-dimethylpentane-1,2-dione; molecular formula: $C_{29}H_{35}F_2N_3O_3$; molecular weight: 511.61 (Compound 155)

This example was prepared according to the process of Scheme XXI as follows.

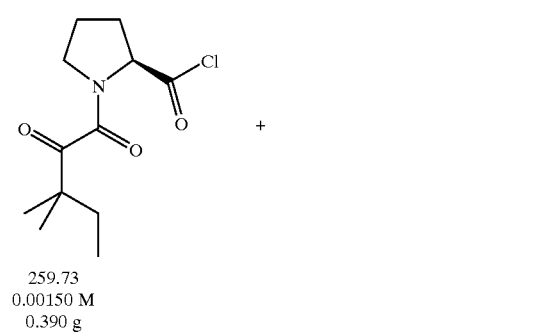

259.73
0.00150 M
0.390 g

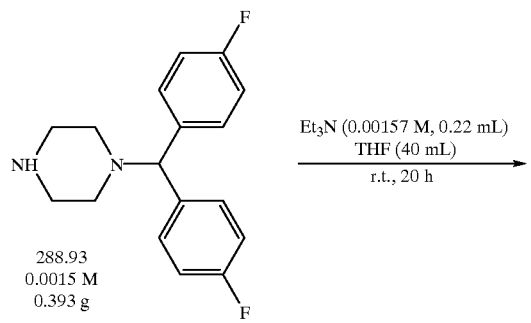

288.93
0.0015 M
0.393 g

Et$_3$N (0.00157 M, 0.22 mL)
THF (40 mL)
r.t., 20 h

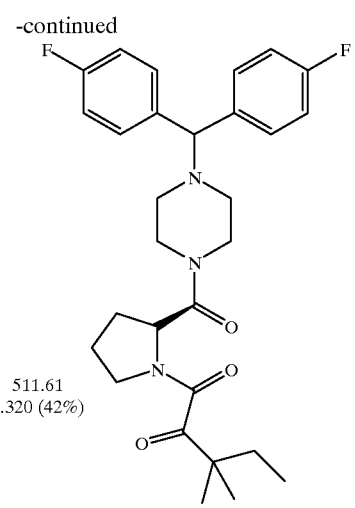

511.61
0.320 (42%)

The procedure is identical to that used in the previous case, except the solvent (THF instead of dichloromethane). Crude product was isolated as a pink-yellow wax, which was triturated with a mixture of EtOAc:hexanes 3:2 and kept in freezer overnight. Filtration of precipitate gave off-white microcrystals (0.320 g, 42%), which were additionally purified by column chromatography (silica gel; eluent—CHC$_3$:MeOH, 25:1). Fractions with $R_f$ ca. 0.40 were collected. Evaporation of solvents gave 0.205 g of white waxy solid with m.p. 58–62° C. $^1$H NMR (CDCl$_3$, 400 MHz): δ8.00–7.80 (m, 4H); 7.15–7.11 (m, 4H); 4.81–4.40 (m, 4H); 4.11–4.00 (m, 1H); 3.91–3.80 (m, 1H); 3.74–3.34 (m, 4H); 3.28–3.14 (m, 1H); 2.83–2.69 (m, 1H); 2.21–2.10 (m, 2H); 2.00–1.88 (m, 2H); 1.85–1.60 (m, 4H); 1.26 and 1.22 (2s, 6H); 0.91 (t, J=7.5 Hz, 3H). Calcd for $C_{24}H_{33}N_3O_5 \cdot 1.25 H_2O$: C, 65.21; H, 7.08; N, 7.87. Found: C, 65.27; H, 6.71; N, 7.13.

Example 22

A lotion comprising the following composition may be prepared.

|  | (%) |
|---|---|
| 95% Ethanol | 80.0 |
| an N-heterocyclic carboxylic acid or carboxylic acid isostere | 10.0 |
| α-Tocopherol acetate | 0.01 |
| Ethylene oxide (40 mole) adducts of hardened castor oil | 0.5 |
| purified water | 9.0 |
| perfume and dye | q.s. |

Into 95% ethanol are added an N-heterocyclic carboxylic acid or carboxylic acid isostere, α-tocopherol acetate, ethylene oxide (40 mole) adducts of hardened castor oil, perfume and a dye. The resulting mixture is stirred and dissolved, and purified water is added to the mixture to obtain a transparent liquid lotion.

5 mL of the lotion may be applied once or twice per day to a site having marked baldness or alopecia.

Example 23

A lotion comprising the following composition shown may be prepared.

|  | (%) |
|---|---|
| 95% Ethanol | 80.0 |
| an N-heterocyclic carboxylic acid or carboxylic acid isostere | 0.005 |
| Hinokitol | 0.01 |
| Ethylene oxide (40 mole) adducts of hardened castor oil | 0.5 |
| Purified water | 19.0 |
| Perfume and dye | q.s. |

Into 95% ethanol are added an N-heterocyclic carboxylic acid or carboxylic acid isostere, hinokitol, ethylene oxide (40 mole) adducts of hardened castor oil, perfume, and a dye. The resulting mixture is stirred, and purified water is added to the mixture to obtain a transparent liquid lotion.

The lotion may be applied by spraying once to 4 times per day to a site having marked baldness or alopecia.

Example 24

An emulsion may be prepared from A phase and B phase having the following compositions.

|  | (%) |
|---|---|
| (A phase) |  |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitan monooleate | 1.0 |
| an N-heterocyclic carboxylic acid or carboxylic acid isostere | 0.01 |
| (B phase) |  |
| Glycerine | 10.0 |
| Purified water | 69.0 |
| Perfume, dye, and preservative | q.s. |

The A phase and the B phase are respectively heated and melted and maintained at 80° C. Both phases are then mixed and cooled under stirring to normal temperature to obtain an emulsion.

The emulsion may be applied by spraying once to four times per day to a site having marked baldness or alopecia.

Example 25

A cream may be prepared from A phase and B phase having the following compositions.

|  | (%) |
|---|---|
| (A Phase) |  |
| Fluid paraffin | 5.0 |
| Cetostearyl alcohol | 5.5 |
| Petrolatum | 5.5 |
| Glycerine monostearate | 33.0 |
| Polyoxyethylene (20 mole) 2-octyldodecyl ether | 3.0 |
| Propylparaben | 0.3 |

-continued

|  | (%) |
|---|---|
| (B Phase) |  |
| an N-heterocyciic carboxylic acid or carboxylic acid isostere | 0.8 |
| Glycerine | 7.0 |
| Dipropylene glycol | 20.0 |
| Polyethylene glycol 4000 | 5.0 |
| Sodium Hexametaphosphate | 0.005 |
| Purified water | 44.895 |

The A phase is heated and melted, and maintained at 70° C. The B phase is added into the A phase and the mixture is stirred to obtain an emulsion. The emulsion is then cooled to obtain a cream.

The cream may be applied once to 4 times per day to a site having marked baldness or alopecia.

Example 26

A liquid comprising the following composition may be

|  | (%) |
|---|---|
| Polyoxyethylene butyl ether | 20.0 |
| Ethanol | 50.0 |
| an N-heterocyclic carboxylic acid or carboxylic acid isostere | 0.001 |
| Propylene glycol | 5.0 |
| Polyoxyethylene hardened castor oil derivative (ethylene oxide 80 mole adducts) | 0.4 |
| Perfume | q.s. |
| Purified water | q.s. |

Into ethanol are added polyoxypropylene butyl ether, propylene glycol, polyoxyethylene hardened castor oil, an N-heterocyclic carboxylic acid or carboxylic acid isostere, and perfume. The resulting mixture is stirred, and purified water is added to the mixture to obtain a liquid.

The liquid may be applied once to 4 times per day to a site having marked baldness or alopecia.

Example 27

A shampoo comprising the following composition may be prepared.

|  | (%) |
|---|---|
| Sodium laurylsulfate | 5.0 |
| Triethanolainine laurylsulfate | 5.0 |
| Betaine lauryldimethylaminoacetate | 6.0 |
| Ethylene glycol distearate | 2.0 |
| Polyethylene glycol | 5.0 |
| an N-heterocyclic carboxylic acid or carboxylic acid isostere | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethyl-aminoacetate. Then a mixture obtained by adding 5.0 g of an N-heterocyclic carboxylic acid or carboxylic acid isoslere, 5.0 g of polyethylene glycol, and 2.0 g of ethylene glycol distearate to 2.0 g of ethanol, followed by stirring, and 0.3 g of perfume are successively added. The resulting mixture is heated and subsequently cooled to obtain a shampoo.

The shampoo may be used on the scalp once or twice per day.

Example 28

A patient is suffering from alopecia senilis. An N-heterocyclic carboxylic acid or carboxylic acid isostere, or a pharmaceutical composition comprising the same, may be administered to the patient. Increased hair growth is expected to occur following treatment.

Example 29

A patient is suffering from male pattern alopecia. An N-heterocyclic carboxylic acid or carboxylic acid isostere, or a pharmaceutical composition comprising the same may be administered to the patient. Increased hair growth is expected to occur following treatment.

Example 30

A patient is suffering from alopecia areata. An N-heterocyclic carboxylic acid or carboxylic acid isostere, or a pharmaceutical composition comprising the same, may be administered to the patient. Increased hair growth is expected to occur following treatment.

Example 31

A patient is suffering from hair loss caused by skin lesions. An N-heterocyclic carboxylic acid or carboxylic acid isostere, or a pharmaceutical composition comprising the same, may be administered to the patient. Increased hair growth is expected to occur following treatment.

Example 32

A patient is suffering from hair loss caused by tumors. An N-heterocyclic carboxylic acid or carboxylic acid isostere, or a pharmaceutical composition comprising the same, may be administered to the patient. Increased hair growth is expected to occur following treatment.

Example 33

A patient is suffering from hair loss caused by a systematic disorder, such as a nutritional disorder or an internal secretion disorder. An N-heterocyclic carboxylic acid or carboxylic acid isostere, or a pharmaceutical composition comprising the same, may be administered to the patient. Increased hair growth is expected to occur following treatment.

Example 34

A patient is suffering from hair loss caused by chemotherapy. An N-heterocyclic carboxylic acid or carboxylic acid isostere, or a pharmaceutical composition comprising the same, may be administered to the patient. Increased hair growth is expected to occur following treatment.

Example 35

A patient is suffering from hair loss caused by radiation. An N-heterocyclic carboxylic acid or carboxylic acid isostere, or a pharmaceutical composition comprising the same may, be administered to the patient. Increased hair growth is expected to occur following treatment.

Example 36

A patient is suffering from a neurodegenerative disease. A carboxylic acid or carboxylic acid isostere of an N-heterocyclic ring or a pharmaceutical composition comprising the same is administered. It would be expected that the patient would improve their condition or recover.

Example 37

A patient is suffering from a neurological disorder. A carboxylic acid or carboxylic acid isostere of an N-heterocyclic ring or pharmaceutical compositions comprising same is administered. It would be expected that the patient would improve their condition or recover.

Example 38

A patient is suffering from stroke. A carboxylic acid or carboxylic acid isostere of an N-heterocyclic ring or pharmaceutical compositions comprising same is administered. It would be expected that the patient would improve their condition or recover.

Example 39

A patient is suffering from Parkinson's Disease. A carboxylic acid or carboxylic acid isostere of an N-heterocyclic ring or pharmaceutical compositions comprising same is administered. It would be expected that the patient would improve their condition or recover.

Example 40

A patient is suffering from Alzheimer's Disease. A carboxylic acid or carboxylic acid isostere of an N-heterocyclic ring or pharmaceutical compositions comprising same is administered. It would be expected that the patient would improve their condition or recover.

Example 41

A patient is suffering from Huntington's Disease. A carboxylic acid or carboxylic acid isostere of an N-heterocyclic ring or pharmaceutical compositions comprising same is administered. It would be expected that the patient would improve their condition or recover.

Example 42

A patient is suffering from a peripheral neuropathy. A carboxylic acid or carboxylic acid isostere of an N-heterocyclic ring or pharmaceutical compositions comprising same is administered. It would be expected that the patient would improve their condition or recover.

Example 43

A patient is suffering from amyotrophic lateral sclerosis. A carboxylic acid or carboxylic acid isostere of an N-heterocyclic ring or pharmaceutical compositions comprising same is administered. It would be expected that the patient would improve their condition or recover.

Example 44

A patient is suffering from a spinal injury. A carboxylic acid or carboxylic acid isostere of an N-heterocyclic ring or pharmaceutical compositions comprising same is administered. It would be expected that the patient would improve their condition or recover.

Example 45

A patient is at risk of suffering from a neurodegenerative disease or neurological disorder. A carboxylic acid or carboxylic acid isostere of an N-heterocyclic ring or a pharmaceutical composition comprising the same is prophelactically administered. It would be expected that the patient would be prevented from some or all of the effects of the disease or disorder, or would significantly improve the condition or recover over patients who were not pre-treated.

Example 46

A patient is suffering from macular degeneration. A carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 47

A patient is suffering from glaucoma, resulting in cupping of the optic nerve disc and damage to nerve fibers. A carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 48

A patient is suffering from cataracts requiring surgery. Following surgery, a carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 49

A patient is suffering from an impairment or blockage of retinal blood supply relating to diabetic retinopathy, ischemic optic neuropathy, or retinal artery or vein blockage. A carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 50

A patient is suffering from a detached retina. A carboxylic acid or carboxylic acid isostere of an N- heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 51

A patient is suffering from tissue damage caused by inflammation associated with uveitis or conjunctivitis. A carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 52

A patient is suffering from photoreceptor damage caused by chronic or acute exposure to ultraviolet light. A carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 53

A patient is suffering from optic neuritis. A carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 54

A patient is suffering from tissue damage associated with a "dry eye" disorder. A carboxylic acid or carboxylic acid isostere of an N-heterocyclic ring as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 55

A patient is suffering from sensorineural hearing loss. A carboxylic acid or carboxylic acid isostere of an N-heterocyclic ring as identified above, alone or in combination with one or more other factors, or a pharmaceutical composition comprising the same, may be administered to the patient. A reduction in hearing loss is expected to occur following treatment.

The invention being thus described, it will be obvious that the same may be varied in many ways. Such variations are not to be regarded as a departure from the spirit and scope of the invention and all such modification are intended to be included within the scope of the following claims.

What is claimed is:

1. A compound having the formula (I):

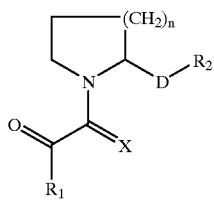

where n is 3;

X is either O or S;

$R_1$ is selected from the group consisting of $C_1$–$C_9$ straight or branched chain alkyl, $C_2$–$C_9$ straight or branched chain alkenyl, aryl, heteroaryl, carbocycle, or heterocycle;

D is a bond, or a $C_1$–$C_{10}$ straight or branched chain alkyl, $C_2$–$C_{10}$ alkenyl or $C_2$–$C_{10}$ alkynyl;

$R_2$ is selected from the group consisting of —COOH; —SO$_3$H; —SO$_2$HNR$^3$; —PO$_2$(R$^3$)$_2$; —CN; —PO$_3$(R$^3$)$_2$; —OR$^3$; —SR$^3$; —NHCOR$^3$; —N(R$^3$)$_2$; —CONZ(R$^3$); —CONH(O)R$^3$; —CONHNHSO$_2$R$^3$; —COHNSO$_2$R$^3$; —CONR$^3$CN;

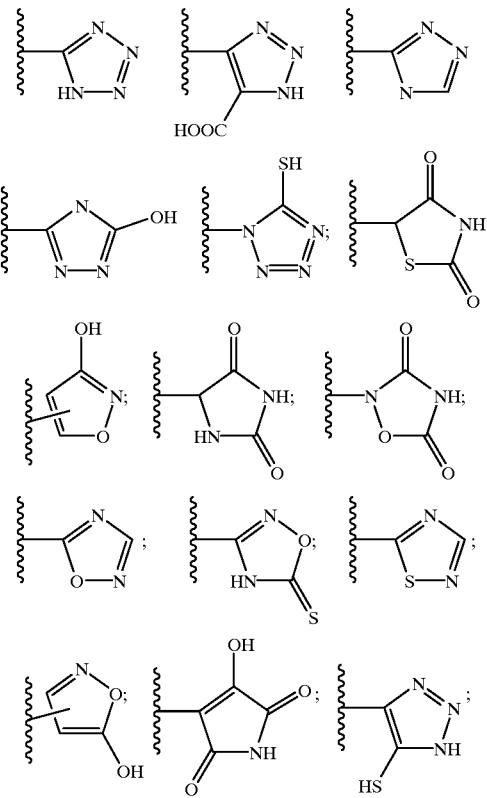

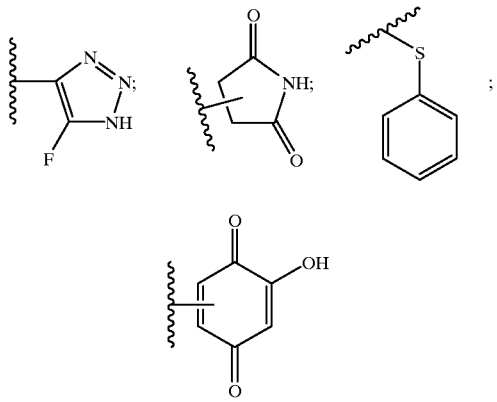

wherein any of the atoms of said ring structure are optionally substituted in one or more positions with R$^3$; and wherein said alkyl, alkenyl, alkynyl, aryl, heteroaryl, carbocycle, or heterocycle is optionally substituted with one or more substituents selected from R$^3$ and Z, where R$^3$ and Z are independently hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, aralkyl, heteroaryl, carbocycle, heterocycle, or CO$_2$R$^7$ where R$^7$ is hydrogen or $C_1$–$C_9$ straight or branched chain alkyl or $C_2$–$C_9$ straight or branched chain alkenyl;

or a pharmaceutically acceptable salt, ester, or solvate thereof.

2. The compounds,

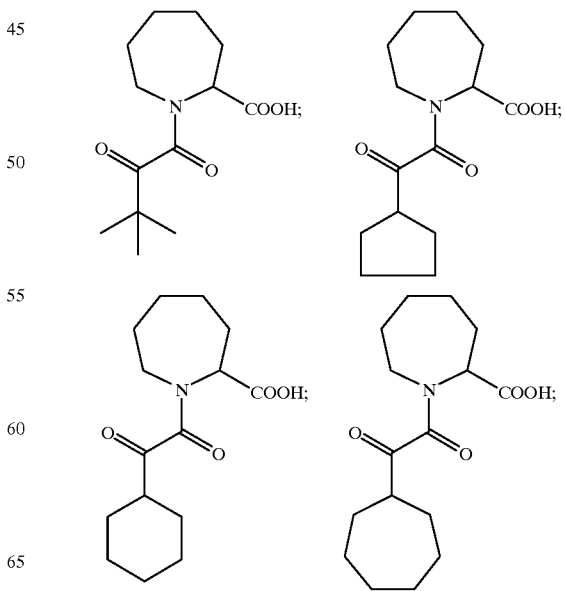

-continued

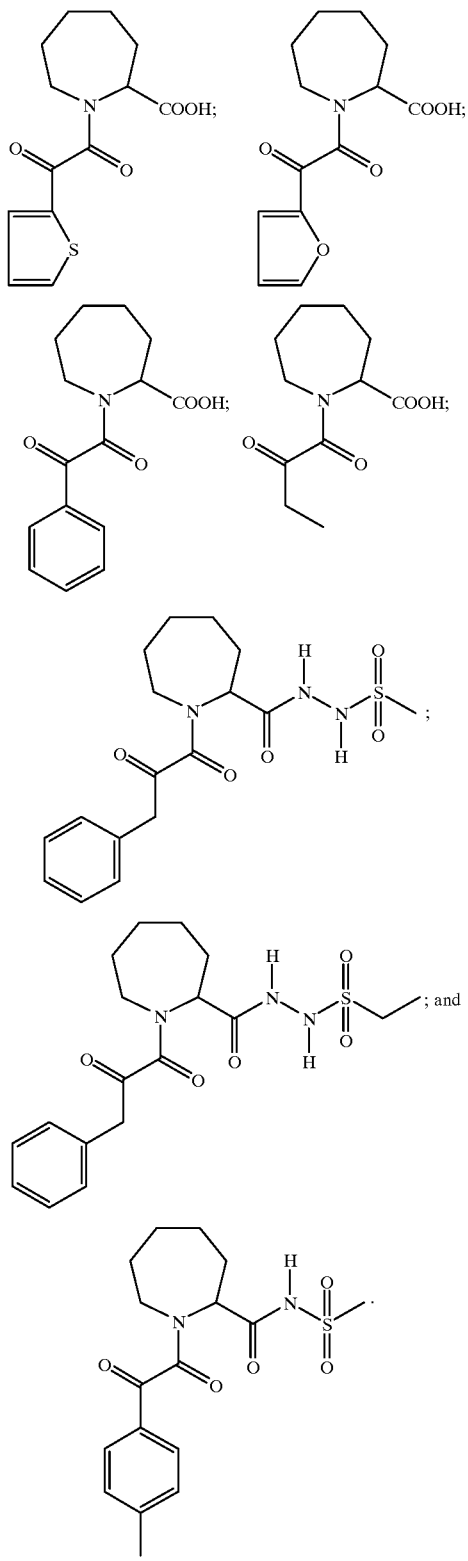

3. A pharmaceutical composition, comprising:
 a) an effective amount of the compound of claim 1; and
 b) a pharmaceutically acceptable carrier.

4. The pharmaceutical composition of claim 3, wherein $R_2$ is a carbocycle or heterocycle containing any combination of $CH_2$, O, S, or N in any chemically stable oxidation state, wherein any of the atoms of said ring structure are optionally substituted in one or more positions with $R^3$.

5. The pharmaceutical composition of claim 3, wherein $R_2$ is selected from the following group:

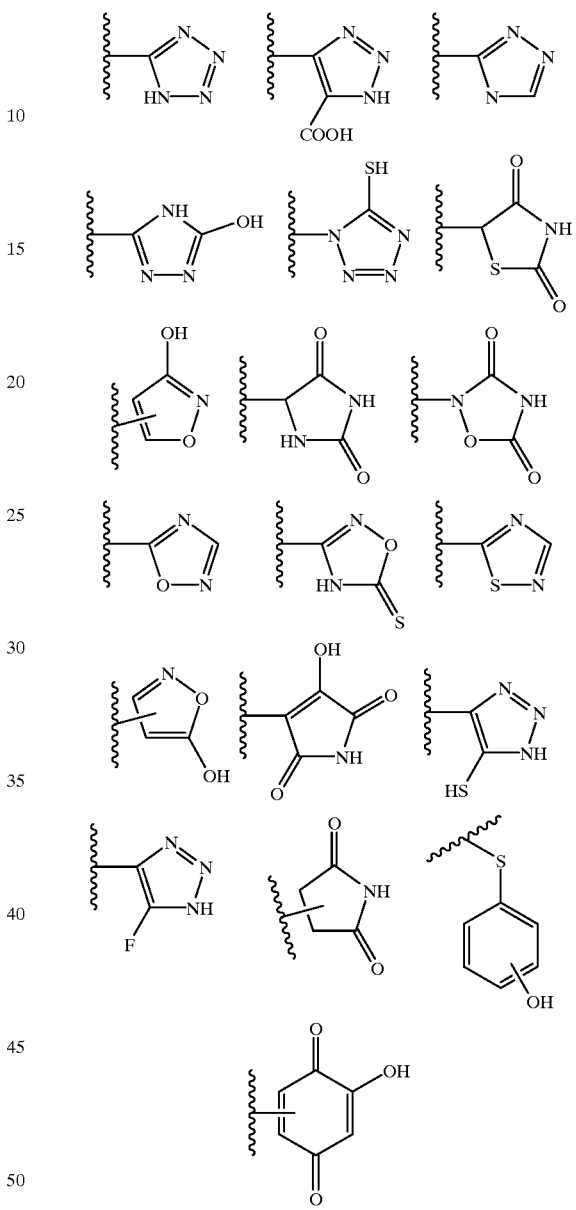

where the atoms of said ring structure may be optionally substituted at one or more positions with $R^3$.

6. The pharmaceutical composition of claim 3, wherein $R_2$ is selected from the group consisting of: —COOH; —SO$_3$H; —SO$_2$HNR$^3$; —PO$_2$(R$^3$)$_2$; —CN; —PO$_3$(R$^3$)$_2$; —OR$^3$; —SR$^3$; —NHCOR$^3$; —N(R$^3$)$_2$; —CON(R$^3$)$_2$; —CONH(O)R$^3$; —CONHNHSO$_2$R$^3$; —COHNSO$_2$R$^3$; and —CONR$^3$CN.

7. The pharmaceutical composition of claim 3, wherein the compound is selected from the group consisting of compounds having the formulae:

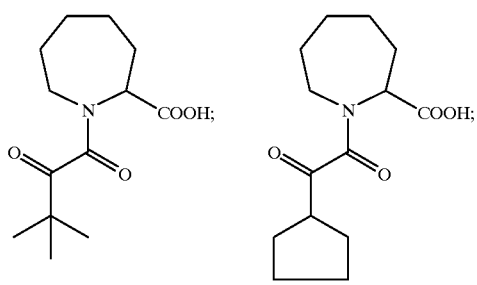

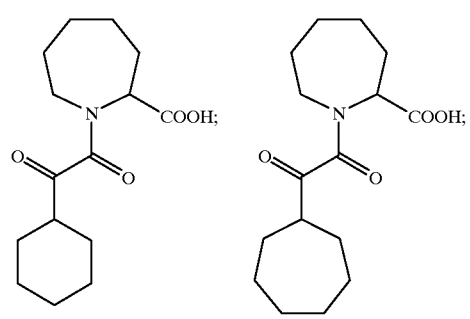

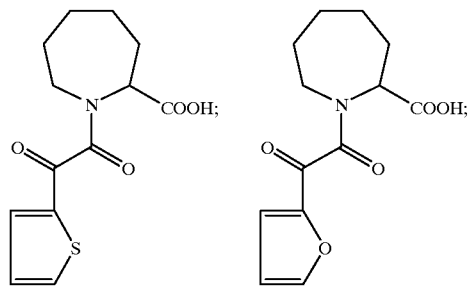

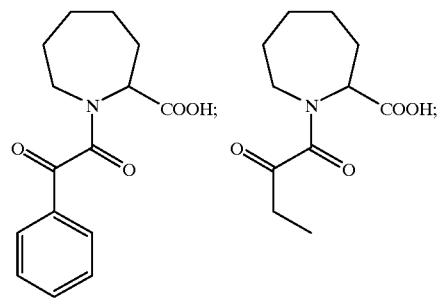

-continued

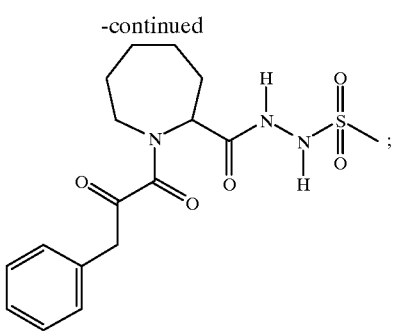

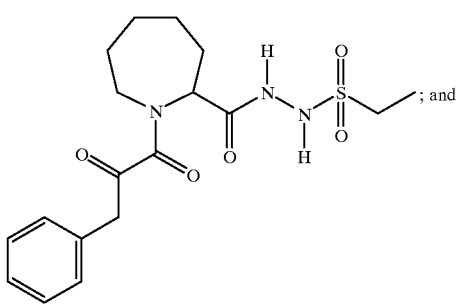

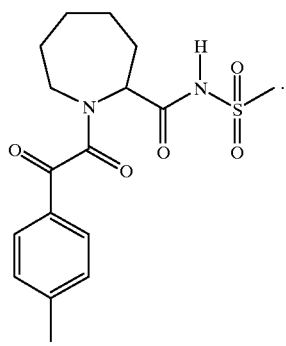

8. A method of treating a neurological disorder in an animal, comprising:
   administering to the animal an effective amount of the compound of claim 1 to stimulate growth of damaged peripheral nerves or to promote neuronal regeneration.

9. The method of claim 8, wherein the neurological disorder is selected from the group consisting of peripheral neuropathies cause by physical injury or disease state, physical damage to the brain, physical damage to the spinal cord, stroke associated with brain damage, and neurological disorders relating to neurodegeneration.

10. The method of claim 8, wherein the neurological disorder is selected from the group consisting of Alzheimer's Disease, Parkinson's Disease, amyotrophic lateral sclerosis, and Huntington's Disease.

11. The method of claim 8, wherein the neurological disorder is Alzheimer's disease.

12. The method of claim 8, wherein the neurological disorder is Parkinson's disease.

13. The method of claim 8, wherein the neurological disorder is amyotrophic lateral sclerosis.

14. The method of claim 8, wherein the neurological disorder is Alzheimer's disease.

15. The method of claim 8, wherein the compound is non-immunosuppressive.

16. The method of claim 8, wherein $R_2$ is selected from the following group:

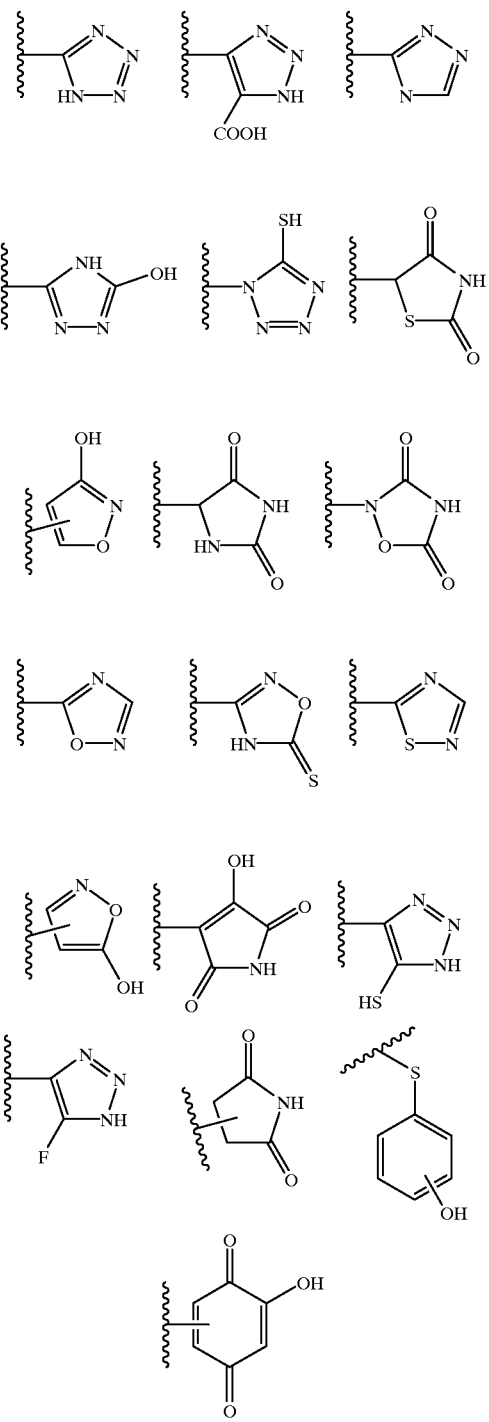

where the atoms of said ring structure may be optionally substituted at one or more positions with $R^3$.

17. The method of claim 8, wherein $R_2$ is selected from the group consisting of: —COOH; —SO$_3$H; —SO$_2$HNR$^3$; —PO$_2$(R$^3$)$_2$; —CN; —PO$_3$(R$^3$)$_2$; —OR$^3$; —SR$^3$; —NHCOR$^3$; —N(R$^3$)$_2$; —CON(R$^3$)$_2$; —CONH(O)R$^3$; —CONHNHSO$_2$R$^3$; —COHNSO$_2$R$^3$; and —CONR$^3$CN.

18. The method of claim 8, wherein the compound is selected from the group consisting of:

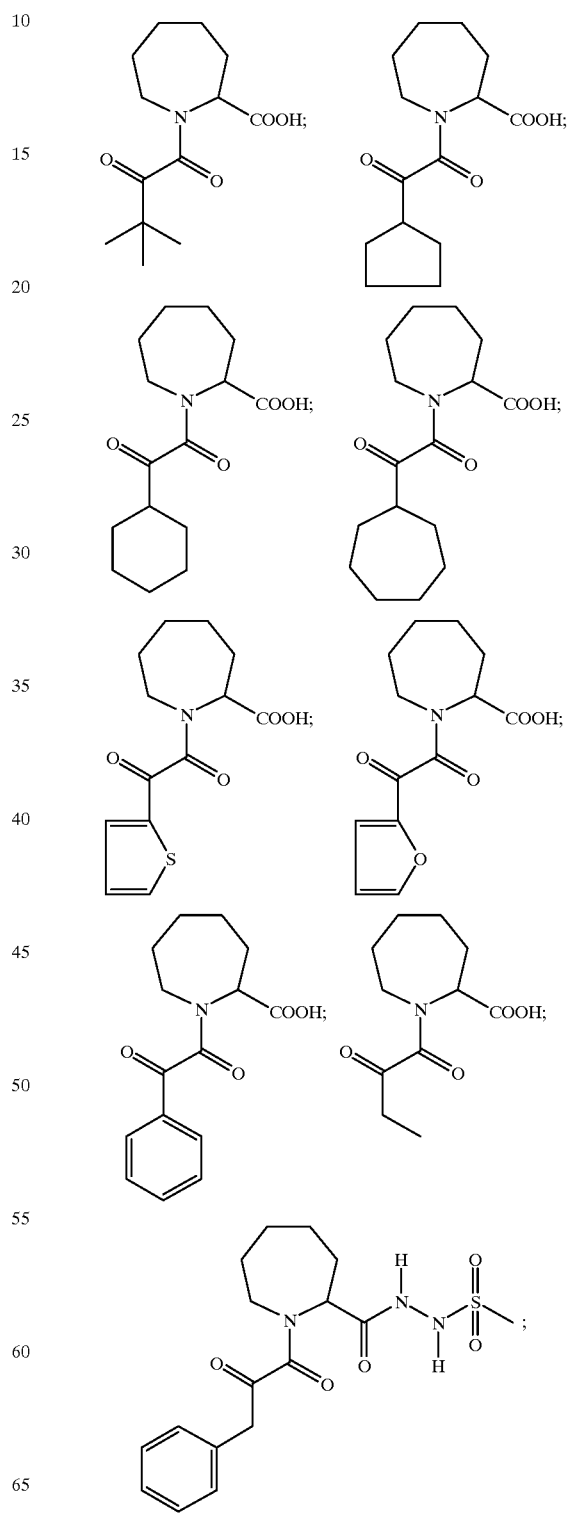

87
-continued
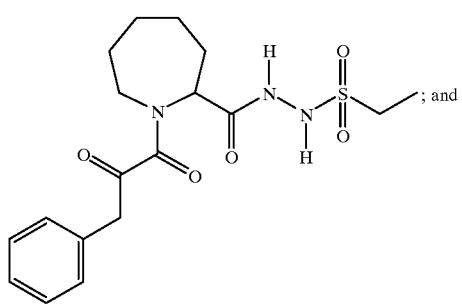
; and
88
-continued
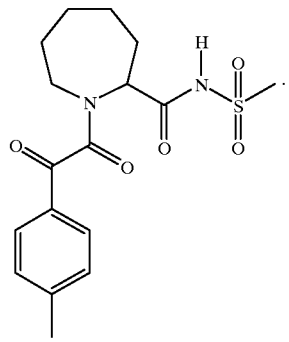
* * * * *